US009512187B2

(12) United States Patent
Je et al.

(10) Patent No.: US 9,512,187 B2
(45) Date of Patent: Dec. 6, 2016

(54) **MUTANT *BACILLUS THURINGIENSIS* PROTEINS AND GENES ENCODING THE SAME WITH IMPROVED INSECTICIDAL ACTIVITY AND USE THEREOF**

(71) Applicant: SNU R&DB FOUNDATION, Seoul (KR)

(72) Inventors: Yeon Ho Je, Gyeonggi-do (KR); Jae Young Choi, Gyeonggi-do (KR); Song Eun Kim, Chungcheongbuk-do (KR); Jae Su Kim, Jeollabuk-do (KR)

(73) Assignee: SNU R&DB FOUNDATION, Seoul (KR)

( * ) Notice: Subject to any disclaimer, the term of this patent is extended or adjusted under 35 U.S.C. 154(b) by 0 days.

(21) Appl. No.: 14/857,257

(22) Filed: Sep. 17, 2015

(65) Prior Publication Data

US 2016/0002301 A1    Jan. 7, 2016

Related U.S. Application Data

(63) Continuation-in-part of application No. PCT/KR2014/000657, filed on Jan. 23, 2014.

(30) Foreign Application Priority Data

Mar. 26, 2013 (KR) .................. 10-2013-0032329
Jan. 15, 2014 (KR) .................. 10-2014-0004841

(51) Int. Cl.
*A01N 63/02* (2006.01)
*C07K 14/325* (2006.01)
*C12N 15/82* (2006.01)

(52) U.S. Cl.
CPC ............. *C07K 14/325* (2013.01); *A01N 63/02* (2013.01); *C12N 15/8286* (2013.01)

(58) Field of Classification Search
CPC . A01N 63/02; C07K 14/325; C12N 15/8286
USPC .............. 435/418; 536/23.71; 800/302
See application file for complete search history.

(56) References Cited

U.S. PATENT DOCUMENTS

2004/0053783 A1* 3/2004 Kern ............... A01N 63/00 504/101
2006/0014936 A1* 1/2006 Malvar ............ C07K 14/325 530/387.1

FOREIGN PATENT DOCUMENTS

| KR | 10-0280380 B1 | | 3/2001 |
|----|---------------|---|--------|
| KR | 10-0375675 B1 | | 3/2003 |
| KR | 10-0432140 B1 | | 5/2004 |
| KR | 10-0436026 B1 | | 6/2004 |
| KR | 10-0599414 B1 | | 7/2006 |
| KR | 10-0723070 B1 | | 5/2007 |
| KR | 2009-005632 | * | 7/2009 |
| WO | WO 2011/031006 | * | 3/2011 |

OTHER PUBLICATIONS

Guang et al, Int. J. Indust. Entomol. 19(1):199-204, 2009.*
Kim et al, Biological Control 47:222-227, 2008.*
Fujimoto et al., "Insect Resistant Rice Generated by Introduction of a Modified δ-endotoxin Gene of Bacillus thuringiensis", Bio/Technology, vol. 11, pp. 1151-1155, (1993).
Kim et al., "Mutagenesis of Bacillus thuringiensis cry1Ac gene and its insecticidal activity against Plutella xylostella and Ostrinia furnacalis", Biological Control, vol. 47, pp. 222-227, (2008).
Perlak et al., "Modification of the coding sequence enhances plant expression of insect control protein genes", Proc. Natl. Acad. Sci. USA, vol. 88, pp. 3324-3328, (1991).
Steward, Jr. et al., "Genetic Transformation, Recovery, and Characterization of Fertile Soybean Transgenic for a Synthetic Bacillus thuringiensis cry1Ac Gene", Plant Physiol., vol. 112, pp. 121-129, (1996).
Strizhov et al., "A synthetic cry1C gene, encoding a Bacillus thuringiensis δ-endotoxin, confers Spodoptera resistance in alfalfa and tobacco", Proc. Natl. Acad. Sci. USA, vol. 93 pp. 15012-15017, (1996).
Xu et al., "Construction of Modified Bacillus thuringiensis cry1Ac Genes for Transgenic Crop Through Multi Site-directed Mutagenesis", Int. J. indust. Entomol., vol. 19, No. 1, pp. 199-204, (2009).
Yang et al., "Development and characterisation of transgenic rice expressing two Bacillus thuringiensis genes", Pest Manag Sci, vol. 67, pp. 414-422, (2011).

* cited by examiner

*Primary Examiner* — Kevin Hill
(74) *Attorney, Agent, or Firm* — Vorys, Sater, Seymour & Pease LLP; Mih Suhn Koh

(57) ABSTRACT

The present disclosure discloses novel Cry1Ac mutants with improved insecticidal activity and/or spectrum against pests belong to Order lepidoptera. Also provided are transgenic plants expressing the present protein and methods for controlling Lepidopteran pest using the present mutants.

7 Claims, 8 Drawing Sheets

FIG. 1B

SEQUENCE LISTING

<160> NUMBER OF SEQ ID NOS: 98

<210> SEQ ID NO 1
<211> LENGTH: 618
<212> TYPE: PRT
<213> ORGANISM: Bacillus thuringiensis -continued

<400> SEQUENCE: 1

```
Met Asp Asn Asn Pro Asn Ile Asn Glu Cys Ile Pro Tyr Asn Cys Leu
 1               5                  10                  15

Ser Asn Pro Glu Val Glu Val Leu Gly Gly Glu Arg Ile Glu Thr Gly
             20                  25                  30

Tyr Thr Pro Ile Asp Ile Ser Leu Ser Leu Thr Gln Phe Leu Leu Ser
         35                  40                  45

Glu Phe Val Pro Gly Ala Gly Phe Val Leu Gly Leu Val Asp Ile Ile
     50                  55                  60

Trp Gly Ile Phe Gly Pro Ser Gln Trp Asp Ala Phe Leu Val Gln Ile
 65                  70                  75                  80

Glu Gln Leu Ile Asn Gln Arg Ile Glu Glu Phe Ala Arg Asn Gln Ala
                 85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
        115                 120                 125

Glu Met Arg Ile Gln Phe Asn Asp Met Asn Ser Ala Leu Thr Thr Ala
    130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp Tyr Ala Val
        195                 200                 205

Arg Trp Tyr Asn Thr Gly Leu Glu Arg Val Trp Gly Pro Asp Ser Arg
    210                 215                 220

Asp Trp Val Arg Tyr Asn Gln Phe Arg Arg Glu Leu Thr Leu Thr Val
225                 230                 235                 240

Leu Asp Ile Val Ala Leu Phe Pro Asn Tyr Asp Ser Arg Arg Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Ser Ala Gln Gly Ile Glu
        275                 280                 285

Arg Ser Ile Arg Ser Pro His Leu Met Asp Ile Leu Asn Ser Ile Thr
    290                 295                 300

Ile Tyr Thr Asp Ala His Arg Gly Tyr Tyr Tyr Trp Ser Gly His Gln
305                 310                 315                 320

Ile Met Ala Phe Pro Val Gly Phe Ser Gly Pro Glu Phe Thr Phe Pro
                325                 330                 335

Leu Tyr Gly Thr Met Gly Asn Ala Ala Pro Gln Gln Arg Ile Val Ala
            340                 345                 350

Gln Leu Gly Gln Gly Val Tyr Arg Thr Leu Ser Ser Thr Leu Tyr Arg
        355                 360                 365

Arg Pro Phe Asn Ile Gly Ile Asn Asn Gln Gln Leu Ser Val Leu Asp
    370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Glu Ile Pro Pro Gln
                405                 410                 415
```

```
Asn Asn Asn Val Pro Pro Arg Gln Gly Phe Ser His Arg Leu Ser His
            420                 425                 430

Val Ser Met Phe Arg Ser Gly Phe Ser Asn Ser Ser Val Ser Ile Ile
            435                 440                 445

Arg Ala Pro Met Phe Ser Trp Ile His Arg Ser Ala Glu Phe Asn Asn
            450                 455                 460

Ile Ile Ala Ser Asp Ser Ile Thr Gln Ile Pro Ala Val Lys Gly Asn
465                 470                 475                 480

Phe Leu Phe Asn Gly Ser Val Ile Ser Gly Pro Gly Phe Thr Gly Gly
                485                 490                 495

Asp Leu Val Arg Leu Asn Ser Ser Gly Asn Asn Ile Gln Asn Arg Gly
            500                 505                 510

Tyr Ile Glu Val Pro Ile His Phe Pro Ser Thr Ser Thr Arg Tyr Arg
            515                 520                 525

Val Arg Val Arg Tyr Ala Ser Val Thr Pro Ile His Leu Asn Val Asn
            530                 535                 540

Trp Gly Asn Ser Ser Ile Phe Ser Asn Thr Val Pro Ala Thr Ala Thr
545                 550                 555                 560

Ser Leu Asp Asn Leu Gln Ser Ser Asp Phe Gly Tyr Phe Glu Ser Ala
                565                 570                 575

Asn Ala Phe Thr Ser Ser Leu Gly Asn Ile Val Gly Val Arg Asn Phe
            580                 585                 590

Ser Gly Thr Ala Gly Val Ile Ile Asp Arg Phe Glu Phe Ile Pro Val
            595                 600                 605

Thr Ala Thr Leu Glu Ala Glu Tyr Asn Leu
            610                 615

<210> SEQ ID NO 2
<211> LENGTH: 618
<212> TYPE: PRT
<213> ORGANISM: Artificial Sequence
<220> FEATURE:
<223> OTHER INFORMATION: Mut-N02

<400> SEQUENCE: 2

Met Asp Asn Asn Pro Asn Ile Asn Glu Cys Ile Pro Tyr Asn Cys Leu
  1               5                  10                  15

Ser Asn Pro Glu Val Glu Val Leu Gly Gly Glu Arg Ile Glu Thr Gly
                 20                  25                  30

Tyr Thr Pro Ile Asp Ile Ser Leu Ser Leu Thr Gln Phe Leu Leu Ser
             35                  40                  45

Glu Phe Val Pro Gly Ala Gly Phe Val Leu Gly Leu Val Asp Ile Ile
 50                  55                  60

Trp Gly Ile Phe Gly Pro Ser Gln Trp Asp Ala Phe Leu Val Gln Ile
 65                  70                  75                  80

Glu Gln Leu Ile Asn Gln Arg Ile Glu Glu Phe Ala Arg Asn Gln Ala
                 85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
            115                 120                 125

Glu Met Arg Ile Gln Phe Asn Asp Met Asn Ser Ala Leu Thr Thr Ala
            130                 135                 140

Ile Pro Leu Phe Ala Val Gln Asn Tyr Gln Val Pro Leu Leu Ser Val
145                 150                 155                 160
```

-continued

Tyr Val Gln Ala Ala Asn Leu His Leu Ser Val Leu Arg Asp Val Ser
            165                 170                 175

Val Phe Gly Gln Arg Trp Gly Phe Asp Ala Thr Thr Ile Asn Ser Arg
            180                 185                 190

Tyr Asn Asp Leu Thr Arg Leu Ile Gly Asn Tyr Thr Asp Tyr Ala Val
            195                 200                 205

Arg Trp Tyr Asn Thr Gly Leu Glu Arg Val Trp Gly Pro Asp Ser Arg
            210                 215                 220

Asp Trp Val Arg Tyr Asn Gln Phe Arg Arg Glu Leu Thr Leu Thr Val
225                 230                 235                 240

Leu Asp Ile Val Ser Leu Phe Ser Asn Tyr Asp Ser Arg Arg Tyr Pro
            245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Met Ala Gln Arg Ile Glu
            275                 280                 285

Arg Ser Ile Arg Ser Pro His Leu Met Asp Ile Leu Asn Ser Ile Thr
            290                 295                 300

Ile Tyr Thr Asp Val His Arg Gly Tyr Tyr Trp Ser Gly His Gln
305                 310                 315                 320

Ile Thr Ala Ser Pro Val Gly Phe Ser Gly Pro Glu Phe Ala Phe Pro
            325                 330                 335

Leu Tyr Gly Thr Met Gly Asn Ala Ala Pro Gln Gln Arg Ile Val Ala
            340                 345                 350

Gln Leu Gly Gln Gly Val Tyr Arg Thr Leu Ser Ser Thr Leu Tyr Arg
            355                 360                 365

Arg Pro Phe Asn Ile Gly Pro Asn Asn Gln Gln Leu Ser Val Leu Asp
            370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Val Ile Pro Pro Gln
            405                 410                 415

Asn Asn Asn Val Pro Pro Arg Ala Gly Phe Ser His Arg Leu Ser His
            420                 425                 430

Val Ser Met Phe Arg Ser Gly Phe Ser Asn Ser Ser Val Ser Ile Ile
            435                 440                 445

Arg Ala Pro Met Phe Ser Trp Ile His Arg Ser Ala Glu Phe Asn Asn
            450                 455                 460

Ile Ile Ala Ser Asp Ser Ile Thr Gln Ile Pro Ala Val Lys Gly Asn
465                 470                 475                 480

Phe Leu Phe Asn Gly Ser Val Ile Ser Gly Pro Gly Phe Thr Gly Gly
            485                 490                 495

Asp Leu Val Arg Leu Asn Ser Ser Gly Asn Asn Ile Gln Asn Arg Gly
            500                 505                 510

Tyr Ile Glu Val Pro Ile His Phe Pro Ser Thr Ser Thr Arg Tyr Arg
            515                 520                 525

Val Arg Val Arg Tyr Ala Ser Val Thr Pro Ile His Leu Asn Val Asn
            530                 535                 540

Trp Gly Asn Ser Ser Ile Phe Ser Asn Thr Val Pro Ala Thr Ala Thr
545                 550                 555                 560

Ser Leu Asp Asn Leu Gln Ser Ser Asp Phe Gly Tyr Phe Glu Ser Ala
            565                 570                 575

```
Asn Ala Phe Thr Ser Ser Leu Gly Asn Ile Val Gly Val Arg Asn Phe
            580                 585                 590

Ser Gly Thr Ala Gly Val Ile Ile Asp Arg Phe Glu Phe Ile Pro Val
        595                 600                 605

Thr Ala Thr Leu Glu Ala Glu Tyr Asn Leu
        610                 615

<210> SEQ ID NO 3
<211> LENGTH: 618
<212> TYPE: PRT
<213> ORGANISM: Artificial Sequence
<220> FEATURE:
<223> OTHER INFORMATION: Mut-N04

<400> SEQUENCE: 3

Met Asp Asn Asn Pro Asn Ile Asn Glu Cys Ile Pro Tyr Asn Cys Leu
  1               5                  10                  15

Ser Asn Pro Glu Val Glu Val Leu Gly Gly Glu Arg Ile Glu Thr Gly
             20                  25                  30

Tyr Thr Pro Ile Asp Ile Ser Leu Ser Leu Thr Gln Phe Leu Leu Ser
         35                  40                  45

Glu Phe Val Pro Gly Ala Gly Phe Val Leu Gly Leu Val Asp Ile Ile
     50                  55                  60

Trp Gly Ile Phe Gly Pro Ser Gln Trp Asp Ala Phe Leu Val Gln Ile
 65                  70                  75                  80

Glu Gln Leu Ile Asn Gln Arg Ile Glu Glu Phe Ala Arg Asn Gln Ala
                 85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
        115                 120                 125

Glu Met Arg Ile Gln Phe Asn Asp Met Asn Ser Ala Leu Thr Thr Ala
    130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Thr Thr Ile Asn Ser Arg
            180                 185                 190

Tyr Asn Asp Leu Thr Arg Leu Ile Gly Asn Tyr Thr Asp Tyr Ala Val
        195                 200                 205

Arg Trp Tyr Asn Thr Gly Leu Glu Arg Val Trp Gly Pro Asp Ser Arg
    210                 215                 220

Asp Trp Val Arg Tyr Asn Gln Phe Arg Arg Glu Leu Thr Leu Thr Val
225                 230                 235                 240

Leu Asp Ile Val Ala Leu Phe Ser Asn Tyr Asp Ser Arg Arg Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Met Ala Gln Arg Ile Glu
        275                 280                 285

Arg Ser Ile Arg Ser Pro His Leu Met Asp Ile Leu Asn Ser Ile Thr
    290                 295                 300

Ile Tyr Thr Asp Val His Arg Gly Tyr Tyr Tyr Trp Ser Gly His Gln
305                 310                 315                 320
```

```
Ile Thr Ala Ser Pro Val Gly Phe Ser Gly Pro Glu Phe Ala Phe Pro
            325                 330                 335

Leu Tyr Gly Thr Met Gly Asn Ala Ala Pro Gln Gln Arg Ile Val Ala
        340                 345                 350

Gln Leu Gly Gln Gly Val Tyr Arg Thr Leu Ser Ser Thr Leu Tyr Arg
    355                 360                 365

Arg Pro Phe Asn Ile Gly Pro Asn Asn Gln Gln Leu Ser Val Leu Asp
370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Val Ile Pro Pro Gln
                405                 410                 415

Asn Asn Asn Val Pro Pro Arg Ala Gly Phe Ser His Arg Leu Ser His
            420                 425                 430

Val Ser Met Phe Arg Ser Gly Phe Ser Asn Ser Ser Val Ser Ile Ile
        435                 440                 445

Arg Ala Pro Met Phe Ser Trp Ile His Arg Ser Ala Glu Phe Asn Asn
    450                 455                 460

Ile Ile Ala Ser Asp Ser Ile Thr Gln Ile Pro Ala Val Lys Gly Asn
465                 470                 475                 480

Phe Leu Phe Asn Gly Ser Val Ile Ser Gly Pro Gly Phe Thr Gly Gly
                485                 490                 495

Asp Leu Val Arg Leu Asn Ser Ser Gly Asn Asn Ile Gln Asn Arg Gly
            500                 505                 510

Tyr Ile Glu Val Pro Ile His Phe Pro Ser Thr Ser Thr Arg Tyr Arg
        515                 520                 525

Val Arg Val Arg Tyr Ala Ser Val Thr Pro Ile His Leu Asn Val Asn
    530                 535                 540

Trp Gly Asn Ser Ser Ile Phe Ser Asn Thr Val Pro Ala Thr Ala Thr
545                 550                 555                 560

Ser Leu Asp Asn Leu Gln Ser Ser Asp Phe Gly Tyr Phe Glu Ser Ala
                565                 570                 575

Asn Ala Phe Thr Ser Ser Leu Gly Asn Ile Val Gly Val Arg Asn Phe
            580                 585                 590

Ser Gly Thr Ala Gly Val Ile Ile Asp Arg Phe Glu Phe Ile Pro Val
        595                 600                 605

Thr Ala Thr Leu Glu Ala Glu Tyr Asn Leu
    610                 615

<210> SEQ ID NO 4
<211> LENGTH: 618
<212> TYPE: PRT
<213> ORGANISM: Artificial Sequence
<220> FEATURE:
<223> OTHER INFORMATION: Mut-N05

<400> SEQUENCE: 4

Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
            20                  25                  30

Tyr Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Val Asp Ile Ile
    50                  55                  60
```

-continued

```
Trp Gly Ile Phe Gly Pro Ser Gln Trp Asp Ala Phe Leu Val Gln Ile
 65                  70                  75                  80

Glu Gln Leu Ile Asn Gln Arg Ile Glu Phe Ala Arg Asn Gln Ala
             85                  90                  95

Ile Ser Arg Leu Glu Gly Leu Ser Asn Leu Tyr Gln Ile Tyr Ala Glu
            100                 105                 110

Ser Phe Arg Ala Trp Glu Ala Asp Pro Thr Asn Pro Ala Leu Arg Glu
            115                 120                 125

Glu Met Arg Ile Gln Phe Asn Asp Met Asn Ser Ala Leu Thr Thr Ala
        130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Thr Thr Ile Asn Ser Arg
            180                 185                 190

Tyr Asn Asp Leu Thr Arg Leu Ile Gly Asn Tyr Thr Asp Tyr Ala Val
            195                 200                 205

Arg Trp Tyr Asn Thr Gly Leu Glu Arg Val Trp Gly Pro Asp Ser Arg
        210                 215                 220

Asp Trp Val Arg Tyr Asn Gln Phe Arg Arg Glu Leu Thr Leu Thr Val
225                 230                 235                 240

Leu Asp Ile Val Ser Leu Phe Ser Asn Tyr Asp Ser Arg Arg Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Met Ala Gln Arg Ile Glu
            275                 280                 285

Arg Ser Ile Arg Ser Pro His Leu Met Asp Ile Leu Asn Ser Ile Thr
        290                 295                 300

Ile Tyr Thr Asp Val His Arg Gly Tyr Tyr Tyr Trp Ser Gly His Gln
305                 310                 315                 320

Ile Thr Ala Ser Pro Val Gly Phe Ser Gly Pro Glu Phe Ala Phe Pro
                325                 330                 335

Leu Tyr Gly Thr Met Gly Asn Ala Ala Pro Gln Gln Arg Ile Val Ala
            340                 345                 350

Gln Leu Gly Gln Gly Val Tyr Arg Thr Leu Ser Ser Thr Leu Tyr Arg
            355                 360                 365

Arg Pro Phe Asn Ile Gly Pro Asn Asn Gln Gln Leu Ser Val Leu Asp
        370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Val Ile Pro Pro Gln
                405                 410                 415

Asn Asn Asn Val Pro Pro Arg Ala Gly Phe Ser His Arg Leu Ser His
            420                 425                 430

Val Ser Met Phe Arg Ser Gly Phe Ser Asn Ser Ser Val Ser Ile Ile
            435                 440                 445

Arg Ala Pro Met Phe Ser Trp Ile His Arg Ser Ala Glu Phe Asn Asn
        450                 455                 460

Ile Ile Ala Ser Asp Ser Ile Thr Gln Ile Pro Ala Val Lys Gly Asn
465                 470                 475                 480

Phe Leu Phe Asn Gly Ser Val Ile Ser Gly Pro Gly Phe Thr Gly Gly
```

```
            485                 490                 495
Asp Leu Val Arg Leu Asn Ser Ser Gly Asn Asn Ile Gln Asn Arg Gly
            500                 505                 510

Tyr Ile Glu Val Pro Ile His Phe Pro Ser Thr Ser Thr Arg Tyr Arg
            515                 520                 525

Val Arg Val Arg Tyr Ala Ser Val Thr Pro Ile His Leu Asn Val Asn
            530                 535                 540

Trp Gly Asn Ser Ser Ile Phe Ser Asn Thr Val Pro Ala Thr Ala Thr
545                 550                 555                 560

Ser Leu Asp Asn Leu Gln Ser Ser Asp Phe Gly Tyr Phe Glu Ser Ala
                565                 570                 575

Asn Ala Phe Thr Ser Ser Leu Gly Asn Ile Val Gly Val Arg Asn Phe
                580                 585                 590

Ser Gly Thr Ala Gly Val Ile Ile Asp Arg Phe Glu Phe Ile Pro Val
            595                 600                 605

Thr Ala Thr Leu Glu Ala Glu Tyr Asn Leu
            610                 615

<210> SEQ ID NO 5
<211> LENGTH: 618
<212> TYPE: PRT
<213> ORGANISM: Artificial Sequence
<220> FEATURE:
<223> OTHER INFORMATION: Mut-N06

<400> SEQUENCE: 5

Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
            20                  25                  30

Tyr Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Val Asp Ile Ile
    50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
        115                 120                 125

Glu Met Arg Ile Gln Phe Asn Asp Met Asn Ser Ala Leu Thr Thr Ala
    130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp Tyr Ala Val
        195                 200                 205

Arg Trp Tyr Asn Thr Gly Leu Glu Arg Val Trp Gly Pro Asp Ser Arg
    210                 215                 220

Asp Trp Val Arg Tyr Asn Gln Phe Arg Arg Glu Leu Thr Leu Thr Val
```

```
            225                 230                 235                 240
Leu Asp Ile Val Ser Leu Phe Ser Asn Tyr Asp Ser Arg Arg Tyr Pro
                245                 250                 255
Ile Arg Thr Val Ser Gln Leu Thr Arg Glu Ile Tyr Thr Asn Pro Val
                260                 265                 270
Leu Glu Asn Phe Asp Gly Ser Phe Arg Gly Met Ala Gln Arg Ile Glu
                275                 280                 285
Arg Ser Ile Arg Ser Pro His Leu Met Asp Ile Leu Asn Ser Ile Thr
        290                 295                 300
Ile Tyr Thr Asp Val His Arg Gly Tyr Tyr Trp Ser Gly His Gln
305                 310                 315                 320
Ile Thr Ala Ser Pro Val Gly Phe Ser Gly Pro Glu Phe Ala Phe Pro
                325                 330                 335
Leu Tyr Gly Thr Met Gly Asn Ala Ala Pro Gln Gln Arg Ile Val Ala
                340                 345                 350
Gln Leu Gly Gln Gly Val Tyr Arg Thr Leu Ser Ser Thr Leu Tyr Arg
            355                 360                 365
Arg Pro Phe Asn Ile Gly Pro Asn Asn Gln Gln Leu Ser Val Leu Asp
    370                 375                 380
Gly Thr Glu Phe Ala Tyr Gly Thr Ser Ser Asn Leu Pro Ser Ala Val
385                 390                 395                 400
Tyr Arg Lys Ser Gly Thr Val Asp Ser Leu Asp Val Ile Pro Pro Gln
                405                 410                 415
Asn Asn Asn Val Pro Pro Arg Ala Gly Phe Ser His Arg Leu Ser His
                420                 425                 430
Val Ser Met Phe Arg Ser Gly Phe Ser Asn Ser Ser Val Ser Ile Ile
            435                 440                 445
Arg Ala Pro Met Phe Ser Trp Ile His Arg Ser Ala Glu Phe Asn Asn
        450                 455                 460
Ile Ile Ala Ser Asp Ser Ile Thr Gln Ile Pro Ala Val Lys Gly Asn
465                 470                 475                 480
Phe Leu Phe Asn Gly Ser Val Ile Ser Gly Pro Gly Phe Thr Gly Gly
                485                 490                 495
Asp Leu Val Arg Leu Asn Ser Ser Gly Asn Asn Ile Gln Asn Arg Gly
                500                 505                 510
Tyr Ile Glu Val Pro Ile His Phe Pro Ser Thr Ser Thr Arg Tyr Arg
            515                 520                 525
Val Arg Val Arg Tyr Ala Ser Val Thr Pro Ile His Leu Asn Val Asn
        530                 535                 540
Trp Gly Asn Ser Ser Ile Phe Ser Asn Thr Val Pro Ala Thr Ala Thr
545                 550                 555                 560
Ser Leu Asp Asn Leu Gln Ser Ser Asp Phe Gly Tyr Phe Glu Ser Ala
                565                 570                 575
Asn Ala Phe Thr Ser Ser Leu Gly Asn Ile Val Gly Val Arg Asn Phe
                580                 585                 590
Ser Gly Thr Ala Gly Val Ile Ile Asp Arg Phe Glu Phe Ile Pro Val
            595                 600                 605
Thr Ala Thr Leu Glu Ala Glu Tyr Asn Leu
    610                 615

<210> SEQ ID NO 6
<211> LENGTH: 618
<212> TYPE: PRT
<213> ORGANISM: Artificial Sequence
```

```
<220> FEATURE:
<223> OTHER INFORMATION: Mut-N09

<400> SEQUENCE: 6

Met Asp Asn Asn Pro Asn Ile Asn Glu Cys Ile Pro Tyr Asn Cys Leu
 1               5                  10                  15

Ser Asn Pro Glu Val Glu Val Leu Gly Gly Glu Arg Ile Glu Thr Gly
            20                  25                  30

Tyr Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Val Asp Ile Ile
    50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
            100                 105                 110

Ser Phe Arg Ala Trp Glu Ala Asp Pro Thr Asn Pro Ala Leu Arg Glu
        115                 120                 125

Glu Met Arg Ile Gln Phe Asn Asp Met Asn Ser Ala Leu Thr Thr Ala
    130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp Tyr Ala Val
        195                 200                 205

Arg Trp Tyr Asn Thr Gly Leu Glu Arg Val Trp Gly Pro Asp Ser Arg
    210                 215                 220

Asp Trp Val Arg Tyr Asn Gln Phe Arg Arg Glu Leu Thr Leu Thr Val
225                 230                 235                 240

Leu Asp Ile Val Ala Leu Phe Ser Asn Tyr Asp Ser Arg Arg Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Met Ala Gln Arg Ile Glu
        275                 280                 285

Arg Ser Ile Arg Ser Pro His Leu Met Asp Ile Leu Asn Ser Ile Thr
    290                 295                 300

Ile Tyr Thr Asp Val His Arg Gly Tyr Tyr Trp Ser Gly His Gln Ile
305                 310                 315                 320

Ile Thr Ala Ser Pro Val Gly Phe Ser Gly Pro Glu Phe Ala Phe Pro
                325                 330                 335

Leu Tyr Gly Thr Met Gly Asn Ala Ala Pro Gln Gln Arg Ile Val Ala
            340                 345                 350

Gln Leu Gly Gln Gly Val Tyr Arg Thr Leu Ser Ser Thr Leu Tyr Arg
        355                 360                 365

Arg Pro Phe Asn Ile Gly Pro Asn Asn Gln Gln Leu Ser Val Leu Asp
    370                 375                 380

Gly Thr Glu Phe Ala Tyr Gly Ser Ser Asn Leu Pro Ser Ala Val
385                 390                 395                 400
```

Tyr Arg Lys Ser Gly Thr Val Asp Ser Leu Asp Val Ile Pro Pro Gln
                405                 410                 415

Asn Asn Asn Val Pro Pro Arg Ala Gly Phe Ser His Arg Leu Ser His
            420                 425                 430

Val Ser Met Phe Arg Ser Gly Phe Ser Asn Ser Ser Val Ser Ile Ile
        435                 440                 445

Arg Ala Pro Met Phe Ser Trp Ile His Arg Ser Ala Glu Phe Asn Asn
    450                 455                 460

Ile Ile Ala Ser Asp Ser Ile Thr Gln Ile Pro Ala Val Lys Gly Asn
465                 470                 475                 480

Phe Leu Phe Asn Gly Ser Val Ile Ser Gly Pro Gly Phe Thr Gly Gly
                485                 490                 495

Asp Leu Val Arg Leu Asn Ser Ser Gly Asn Asn Ile Gln Asn Arg Gly
            500                 505                 510

Tyr Ile Glu Val Pro Ile His Phe Pro Ser Thr Ser Thr Arg Tyr Arg
        515                 520                 525

Val Arg Val Arg Tyr Ala Ser Val Thr Pro Ile His Leu Asn Val Asn
    530                 535                 540

Trp Gly Asn Ser Ser Ile Phe Ser Asn Thr Val Pro Ala Thr Ala Thr
545                 550                 555                 560

Ser Leu Asp Asn Leu Gln Ser Ser Asp Phe Gly Tyr Phe Glu Ser Ala
                565                 570                 575

Asn Ala Phe Thr Ser Ser Leu Gly Asn Ile Val Gly Val Arg Asn Phe
            580                 585                 590

Ser Gly Thr Ala Gly Val Ile Ile Asp Arg Phe Glu Phe Ile Pro Val
        595                 600                 605

Thr Ala Thr Leu Glu Ala Glu Tyr Asn Leu
    610                 615

<210> SEQ ID NO 7
<211> LENGTH: 618
<212> TYPE: PRT
<213> ORGANISM: Artificial Sequence
<220> FEATURE:
<223> OTHER INFORMATION: Mut-N10

<400> SEQUENCE: 7

Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
            20                  25                  30

Tyr Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Val Asp Ile Ile
    50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Val
        115                 120                 125

Glu Met Arg Ile Gln Phe Asn Asp Met Asn Ser Ala Leu Thr Thr Ala
    130                 135                 140

```
Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Thr Thr Ile Asn Ser Arg
            180                 185                 190

Tyr Asn Asp Leu Thr Arg Leu Ile Gly Asn Tyr Thr Asp Tyr Ala Val
            195                 200                 205

Arg Trp Tyr Asn Thr Gly Leu Glu Arg Val Trp Gly Pro Asp Ser Arg
            210                 215                 220

Asp Trp Val Arg Tyr Asn Gln Phe Arg Arg Glu Leu Thr Leu Thr Val
225                 230                 235                 240

Leu Asp Ile Val Ser Leu Phe Ser Asn Tyr Asp Ser Arg Thr Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Met Ala Gln Arg Ile Glu
            275                 280                 285

Arg Ser Ile Arg Ser Pro His Leu Met Asp Ile Leu Asn Ser Ile Thr
290                 295                 300

Ile Tyr Thr Asp Val His Arg Gly Tyr Tyr Trp Ser Gly His Gln
305                 310                 315                 320

Ile Thr Ala Ser Pro Val Gly Phe Ser Gly Pro Glu Phe Ala Phe Pro
            325                 330                 335

Leu Tyr Gly Thr Met Gly Asn Ala Ala Pro Gln Gln Arg Ile Val Ala
            340                 345                 350

Gln Leu Gly Gln Gly Val Tyr Arg Thr Leu Ser Ser Thr Leu Tyr Arg
            355                 360                 365

Arg Pro Phe Asn Ile Gly Pro Asn Asn Gln Gln Leu Ser Val Leu Asp
            370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Val Ile Pro Pro Gln
            405                 410                 415

Asn Asn Asn Val Pro Pro Arg Ala Gly Phe Ser His Arg Leu Ser His
            420                 425                 430

Val Ser Met Phe Arg Ser Gly Phe Ser Asn Ser Ser Val Ser Ile Ile
            435                 440                 445

Arg Ala Pro Met Phe Ser Trp Ile His Arg Ser Ala Glu Phe Asn Asn
            450                 455                 460

Ile Ile Ala Ser Asp Ser Ile Thr Gln Ile Pro Ala Val Lys Gly Asn
465                 470                 475                 480

Phe Leu Phe Asn Gly Ser Val Ile Ser Gly Pro Gly Phe Thr Gly Gly
            485                 490                 495

Asp Leu Val Arg Leu Asn Ser Ser Gly Asn Asn Ile Gln Asn Arg Gly
            500                 505                 510

Tyr Ile Glu Val Pro Ile His Phe Pro Ser Thr Ser Thr Arg Tyr Arg
            515                 520                 525

Val Arg Val Arg Tyr Ala Ser Val Thr Pro Ile His Leu Asn Val Asn
            530                 535                 540

Trp Gly Asn Ser Ser Ile Phe Ser Asn Thr Val Pro Ala Thr Ala Thr
545                 550                 555                 560
```

```
Ser Leu Asp Asn Leu Gln Ser Asp Phe Gly Tyr Phe Glu Ser Ala
            565                 570                 575

Asn Ala Phe Thr Ser Ser Leu Gly Asn Ile Val Gly Val Arg Asn Phe
        580                 585                 590

Ser Gly Thr Ala Gly Val Ile Ile Asp Arg Phe Glu Phe Ile Pro Val
            595                 600                 605

Thr Ala Thr Leu Glu Ala Glu Tyr Asn Leu
            610                 615

<210> SEQ ID NO 8
<211> LENGTH: 618
<212> TYPE: PRT
<213> ORGANISM: Artificial Sequence
<220> FEATURE:
<223> OTHER INFORMATION: Mut-N12

<400> SEQUENCE: 8

Met Asp Asn Asn Pro Asn Ile Asn Glu Cys Ile Pro Tyr Asn Cys Leu
  1               5                  10                  15

Ser Asn Pro Glu Val Glu Val Leu Gly Gly Glu Arg Ile Glu Thr Gly
                20                  25                  30

Tyr Thr Pro Ile Asp Ile Ser Leu Ser Leu Thr Gln Phe Leu Leu Ser
            35                  40                  45

Glu Phe Val Pro Gly Ala Gly Phe Val Leu Gly Leu Val Asp Ile Ile
     50                  55                  60

Trp Gly Ile Phe Gly Pro Ser Gln Trp Asp Ala Phe Leu Val Gln Ile
 65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Val
        115                 120                 125

Glu Met Arg Ile Gln Phe Asn Asp Met Asn Ser Ala Leu Thr Thr Ala
    130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Thr Thr Ile Asn Ser Arg
            180                 185                 190

Tyr Asn Asp Leu Thr Arg Leu Ile Gly Asn Tyr Thr Asp Tyr Ala Val
        195                 200                 205

Arg Trp Tyr Asn Thr Gly Leu Glu Arg Val Trp Gly Pro Asp Ser Arg
    210                 215                 220

Asp Trp Ile Arg Tyr Asn Gln Phe Arg Arg Glu Leu Thr Leu Thr Val
225                 230                 235                 240

Leu Asp Ile Val Ser Leu Phe Ser Asn Tyr Asp Ser Arg Thr Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Met Ala Gln Arg Ile Glu
        275                 280                 285

Arg Ser Ile Arg Ser Pro His Leu Met Asp Ile Leu Asn Ser Ile Thr
    290                 295                 300
```

Ile Tyr Thr Asp Val His Arg Gly Tyr Tyr Trp Ser Gly His Gln
305                 310                 315                 320

Ile Thr Ala Ser Pro Val Gly Phe Ser Gly Pro Glu Phe Ala Phe Pro
                325                 330                 335

Leu Tyr Gly Thr Met Gly Asn Ala Ala Pro Gln Gln Arg Ile Val Ala
                340                 345                 350

Gln Leu Gly Gln Gly Val Tyr Arg Thr Leu Ser Ser Thr Leu Tyr Arg
            355                 360                 365

Arg Pro Phe Asn Ile Gly Pro Asn Asn Gln Gln Leu Ser Val Leu Asp
        370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Val Ile Pro Pro Gln
                405                 410                 415

Asn Asn Asn Val Pro Pro Arg Ala Gly Phe Ser His Arg Leu Ser His
                420                 425                 430

Val Ser Met Phe Arg Ser Gly Phe Ser Asn Ser Ser Val Ser Ile Ile
            435                 440                 445

Arg Ala Pro Met Phe Ser Trp Ile His Arg Ser Ala Glu Phe Asn Asn
        450                 455                 460

Ile Ile Ala Ser Asp Ser Ile Thr Gln Ile Pro Ala Val Lys Gly Asn
465                 470                 475                 480

Phe Leu Phe Asn Gly Ser Val Ile Ser Gly Pro Gly Phe Thr Gly Gly
                485                 490                 495

Asp Leu Val Arg Leu Asn Ser Ser Gly Asn Asn Ile Gln Asn Arg Gly
            500                 505                 510

Tyr Ile Glu Val Pro Ile His Phe Pro Ser Thr Ser Thr Arg Tyr Arg
        515                 520                 525

Val Arg Val Arg Tyr Ala Ser Val Thr Pro Ile His Leu Asn Val Asn
530                 535                 540

Trp Gly Asn Ser Ser Ile Phe Ser Asn Thr Val Pro Ala Thr Ala Thr
545                 550                 555                 560

Ser Leu Asp Asn Leu Gln Ser Ser Asp Phe Gly Tyr Phe Glu Ser Ala
                565                 570                 575

Asn Ala Phe Thr Ser Ser Leu Gly Asn Ile Val Gly Val Arg Asn Phe
                580                 585                 590

Ser Gly Thr Ala Gly Val Ile Ile Asp Arg Phe Glu Phe Ile Pro Val
            595                 600                 605

Thr Ala Thr Leu Glu Ala Glu Tyr Asn Leu
    610                 615

<210> SEQ ID NO 9
<211> LENGTH: 618
<212> TYPE: PRT
<213> ORGANISM: Artificial Sequence
<220> FEATURE:
<223> OTHER INFORMATION: Mut-N14

<400> SEQUENCE: 9

Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
                20                  25                  30

Tyr Thr Pro Ile Asp Ile Ser Leu Ser Leu Thr Gln Phe Leu Leu Ser
            35                  40                  45

```
Glu Phe Val Pro Gly Ala Gly Phe Val Leu Gly Leu Val Asp Ile Ile
 50                  55                  60
Trp Gly Ile Phe Gly Pro Ser Gln Trp Asp Ala Phe Leu Val Gln Ile
 65                  70                  75                  80
Glu Gln Leu Ile Asn Gln Arg Ile Glu Glu Phe Ala Arg Asn Gln Ala
                 85                  90                  95
Ile Ser Arg Leu Glu Gly Leu Ser Asn Leu Tyr Gln Ile Tyr Ala Glu
             100                 105                 110
Ser Phe Arg Glu Trp Glu Ala Asp Pro Thr Asn Pro Ala Leu Arg Val
         115                 120                 125
Glu Met Arg Ile Gln Phe Asn Asp Met Asn Ser Ala Leu Thr Thr Ala
     130                 135                 140
Ile Pro Leu Phe Ala Val Gln Asn Tyr Gln Val Pro Leu Leu Ser Val
145                 150                 155                 160
Tyr Val Gln Ala Ala Asn Leu His Leu Ser Val Leu Arg Asp Val Ser
                 165                 170                 175
Val Phe Gly Gln Arg Trp Gly Phe Asp Ala Thr Thr Ile Asn Ser Arg
             180                 185                 190
Tyr Asn Asp Leu Thr Arg Leu Ile Gly Asn Tyr Thr Asp Tyr Ala Val
         195                 200                 205
Arg Trp Tyr Asn Thr Gly Leu Glu Arg Val Trp Gly Pro Asp Ser Arg
     210                 215                 220
Asp Trp Ile Arg Tyr Asn Gln Phe Arg Arg Glu Leu Thr Leu Thr Val
225                 230                 235                 240
Leu Asp Ile Val Ser Leu Phe Ser Asn Tyr Asp Ser Arg Arg Tyr Pro
                 245                 250                 255
Ile Arg Thr Val Ser Gln Leu Thr Arg Glu Ile Tyr Thr Asn Pro Val
             260                 265                 270
Leu Glu Asn Phe Asp Gly Ser Phe Arg Gly Met Ala Gln Arg Ile Glu
         275                 280                 285
Arg Ser Ile Arg Ser Pro His Leu Met Asp Ile Leu Asn Ser Ile Thr
     290                 295                 300
Ile Tyr Thr Asp Val His Arg Gly Tyr Tyr Tyr Trp Ser Gly His Gln
305                 310                 315                 320
Ile Thr Ala Ser Pro Val Gly Phe Ser Gly Pro Glu Phe Ala Phe Pro
                 325                 330                 335
Leu Tyr Gly Thr Met Gly Asn Ala Ala Pro Gln Gln Arg Ile Val Ala
             340                 345                 350
Gln Leu Gly Gln Gly Val Tyr Arg Thr Leu Ser Ser Thr Leu Tyr Arg
         355                 360                 365
Arg Pro Phe Asn Ile Gly Pro Asn Asn Gln Gln Leu Ser Val Leu Asp
     370                 375                 380
Gly Thr Glu Phe Ala Tyr Gly Thr Ser Ser Asn Leu Pro Ser Ala Val
385                 390                 395                 400
Tyr Arg Lys Ser Gly Thr Val Asp Ser Leu Asp Val Ile Pro Pro Gln
                 405                 410                 415
Asn Asn Asn Val Pro Pro Arg Ala Gly Phe Ser His Arg Leu Ser His
             420                 425                 430
Val Ser Met Phe Arg Ser Gly Phe Ser Asn Ser Ser Val Ser Ile Ile
         435                 440                 445
Arg Ala Pro Met Phe Ser Trp Ile His Arg Ser Ala Glu Phe Asn Asn
     450                 455                 460
Ile Ile Ala Ser Asp Ser Ile Thr Gln Ile Pro Ala Val Lys Gly Asn
```

```
                465                 470                 475                 480
            Phe Leu Phe Asn Gly Ser Val Ile Ser Gly Pro Gly Phe Thr Gly Gly
                            485                 490                 495

Asp Leu Val Arg Leu Asn Ser Ser Gly Asn Asn Ile Gln Asn Arg Gly
                            500                 505                 510

Tyr Ile Glu Val Pro Ile His Phe Pro Ser Thr Ser Thr Arg Tyr Arg
                            515                 520                 525

Val Arg Val Arg Tyr Ala Ser Val Thr Pro Ile His Leu Asn Val Asn
                            530                 535                 540

Trp Gly Asn Ser Ser Ile Phe Ser Asn Thr Val Pro Ala Thr Ala Thr
            545                 550                 555                 560

Ser Leu Asp Asn Leu Gln Ser Ser Asp Phe Gly Tyr Phe Glu Ser Ala
                            565                 570                 575

Asn Ala Phe Thr Ser Ser Leu Gly Asn Ile Val Gly Val Arg Asn Phe
                            580                 585                 590

Ser Gly Thr Ala Gly Val Ile Ile Asp Arg Phe Glu Phe Ile Pro Val
                            595                 600                 605

Thr Ala Thr Leu Glu Ala Glu Tyr Asn Leu
                            610                 615

<210> SEQ ID NO 10
<211> LENGTH: 618
<212> TYPE: PRT
<213> ORGANISM: Artificial Sequence
<220> FEATURE:
<223> OTHER INFORMATION: Mut-N16

<400> SEQUENCE: 10

Met Asp Asn Asn Pro Asn Ile Asn Glu Cys Ile Pro Tyr Asn Cys Leu
            1               5                   10                  15

Ser Asn Pro Glu Val Glu Val Leu Gly Gly Glu Arg Ile Glu Thr Gly
                            20                  25                  30

Tyr Thr Pro Ile Asp Ile Ser Leu Ser Leu Thr Gln Phe Leu Leu Ser
                            35                  40                  45

Glu Phe Val Pro Gly Ala Gly Phe Val Leu Gly Leu Val Asp Ile Ile
                    50                  55                  60

Trp Gly Ile Phe Gly Pro Ser Gln Trp Asp Ala Phe Leu Val Gln Ile
            65                  70                  75                  80

Glu Gln Leu Ile Asn Gln Arg Ile Glu Glu Phe Ala Arg Asn Gln Ala
                            85                  90                  95

Ile Ser Arg Leu Glu Gly Leu Ser Asn Leu Tyr Gln Ile Tyr Ala Glu
                            100                 105                 110

Ser Phe Arg Ala Trp Glu Ala Asp Pro Thr Asn Pro Ala Leu Arg Val
                            115                 120                 125

Glu Met Arg Ile Gln Phe Asn Asp Met Asn Ser Ala Leu Thr Thr Ala
                            130                 135                 140

Ile Pro Leu Phe Ala Val Gln Asn Tyr Gln Val Pro Leu Leu Ser Val
            145                 150                 155                 160

Tyr Val Gln Ala Ala Asn Leu His Leu Ser Val Leu Arg Asp Val Ser
                            165                 170                 175

Val Phe Gly Gln Arg Trp Gly Phe Asp Ala Thr Thr Ile Asn Ser Arg
                            180                 185                 190

Tyr Asn Asp Leu Thr Arg Leu Ile Gly Asn Tyr Thr Asp Tyr Ala Val
                            195                 200                 205

Arg Trp Tyr Asn Thr Gly Leu Glu Arg Val Trp Gly Pro Asp Ser Arg
```

```
              210                 215                 220
Asp Trp Ile Arg Tyr Asn Gln Phe Arg Arg Glu Leu Thr Leu Thr Val
225                 230                 235                 240

Leu Asp Ile Val Ser Leu Phe Ser Asn Tyr Asp Ser Arg Thr Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Met Ala Gln Arg Ile Glu
        275                 280                 285

Arg Ser Ile Arg Ser Pro His Leu Met Asp Ile Leu Asn Ser Ile Thr
    290                 295                 300

Ile Tyr Thr Asp Val His Arg Gly Tyr Tyr Trp Ser Gly His Gln
305                 310                 315                 320

Ile Thr Ala Ser Pro Val Gly Phe Ser Gly Pro Glu Phe Ala Phe Pro
                325                 330                 335

Leu Tyr Gly Thr Met Gly Asn Ala Ala Pro Gln Gln Arg Ile Val Ala
            340                 345                 350

Gln Leu Gly Gln Gly Val Tyr Arg Thr Leu Ser Ser Thr Leu Tyr Arg
        355                 360                 365

Arg Pro Phe Asn Ile Gly Pro Asn Asn Gln Gln Leu Ser Val Leu Asp
    370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Val Ile Pro Pro Gln
                405                 410                 415

Asn Asn Asn Val Pro Pro Arg Ala Gly Phe Ser His Arg Leu Ser His
            420                 425                 430

Val Ser Met Phe Arg Ser Gly Phe Ser Asn Ser Ser Val Ser Ile Ile
        435                 440                 445

Arg Ala Pro Met Phe Ser Trp Ile His Arg Ser Ala Glu Phe Asn Asn
    450                 455                 460

Ile Ile Ala Ser Asp Ser Ile Thr Gln Ile Pro Ala Val Lys Gly Asn
465                 470                 475                 480

Phe Leu Phe Asn Gly Ser Val Ile Ser Gly Pro Gly Phe Thr Gly Gly
                485                 490                 495

Asp Leu Val Arg Leu Asn Ser Ser Gly Asn Asn Ile Gln Asn Arg Gly
            500                 505                 510

Tyr Ile Glu Val Pro Ile His Phe Pro Ser Thr Ser Thr Arg Tyr Arg
        515                 520                 525

Val Arg Val Arg Tyr Ala Ser Val Thr Pro Ile His Leu Asn Val Asn
    530                 535                 540

Trp Gly Asn Ser Ser Ile Phe Ser Asn Thr Val Pro Ala Thr Ala Thr
545                 550                 555                 560

Ser Leu Asp Asn Leu Gln Ser Ser Asp Phe Gly Tyr Phe Glu Ser Ala
                565                 570                 575

Asn Ala Phe Thr Ser Ser Leu Gly Asn Ile Val Gly Val Arg Asn Phe
            580                 585                 590

Ser Gly Thr Ala Gly Val Ile Ile Asp Arg Phe Glu Phe Ile Pro Val
        595                 600                 605

Thr Ala Thr Leu Glu Ala Glu Tyr Asn Leu
    610                 615
```

<210> SEQ ID NO 11

<211> LENGTH: 618
<212> TYPE: PRT
<213> ORGANISM: Artificial Sequence
<220> FEATURE:
<223> OTHER INFORMATION: Mut-N17

<400> SEQUENCE: 11

```
Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
            20                  25                  30

Tyr Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Val Asp Ile Ile
    50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
            100                 105                 110

Ser Phe Arg Ala Trp Glu Ala Asp Pro Thr Asn Pro Ala Leu Arg Val
        115                 120                 125

Glu Met Arg Ile Gln Phe Asn Asp Met Asn Ser Ala Leu Thr Thr Ala
    130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Thr Thr Ile Asn Ser Arg
            180                 185                 190

Tyr Asn Asp Leu Thr Arg Leu Ile Gly Asn Tyr Thr Asp Tyr Ala Val
        195                 200                 205

Arg Trp Tyr Asn Thr Gly Leu Glu Arg Val Trp Gly Pro Asp Ser Arg
    210                 215                 220

Asp Trp Val Arg Tyr Asn Gln Phe Arg Arg Glu Leu Thr Leu Thr Val
225                 230                 235                 240

Leu Asp Ile Val Ser Leu Phe Ser Asn Tyr Asp Ser Arg Thr Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Met Ala Gln Arg Ile Glu
        275                 280                 285

Arg Ser Ile Arg Ser Pro His Leu Met Asp Ile Leu Asn Ser Ile Thr
    290                 295                 300

Ile Tyr Thr Asp Val His Arg Gly Tyr Tyr Trp Ser Gly His Gln
305                 310                 315                 320

Ile Thr Ala Ser Pro Val Gly Phe Ser Gly Pro Glu Phe Ala Phe Pro
                325                 330                 335

Leu Tyr Gly Thr Met Gly Asn Ala Ala Pro Gln Gln Arg Ile Val Ala
            340                 345                 350

Gln Leu Gly Gln Gly Val Tyr Arg Thr Leu Ser Ser Thr Leu Tyr Arg
        355                 360                 365

Arg Pro Phe Asn Ile Gly Pro Asn Asn Gln Gln Leu Ser Val Leu Asp
    370                 375                 380
```

```
Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Val Ile Pro Pro Gln
            405                 410                 415

Asn Asn Asn Val Pro Pro Arg Ala Gly Phe Ser His Arg Leu Ser His
            420                 425                 430

Val Ser Met Phe Arg Ser Gly Phe Ser Asn Ser Ser Val Ser Ile Ile
        435                 440                 445

Arg Ala Pro Met Phe Ser Trp Ile His Arg Ser Ala Glu Phe Asn Asn
    450                 455                 460

Ile Ile Ala Ser Asp Ser Ile Thr Gln Ile Pro Ala Val Lys Gly Asn
465                 470                 475                 480

Phe Leu Phe Asn Gly Ser Val Ile Ser Gly Pro Gly Phe Thr Gly Gly
            485                 490                 495

Asp Leu Val Arg Leu Asn Ser Ser Gly Asn Asn Ile Gln Asn Arg Gly
            500                 505                 510

Tyr Ile Glu Val Pro Ile His Phe Pro Ser Thr Ser Thr Arg Tyr Arg
        515                 520                 525

Val Arg Val Arg Tyr Ala Ser Val Thr Pro Ile His Leu Asn Val Asn
        530                 535                 540

Trp Gly Asn Ser Ser Ile Phe Ser Asn Thr Val Pro Ala Thr Ala Thr
545                 550                 555                 560

Ser Leu Asp Asn Leu Gln Ser Ser Asp Phe Gly Tyr Phe Glu Ser Ala
            565                 570                 575

Asn Ala Phe Thr Ser Ser Leu Gly Asn Ile Val Gly Val Arg Asn Phe
        580                 585                 590

Ser Gly Thr Ala Gly Val Ile Ile Asp Arg Phe Glu Phe Ile Pro Val
        595                 600                 605

Thr Ala Thr Leu Glu Ala Glu Tyr Asn Leu
    610                 615

<210> SEQ ID NO 12
<211> LENGTH: 618
<212> TYPE: PRT
<213> ORGANISM: Artificial Sequence
<220> FEATURE:
<223> OTHER INFORMATION: Mut-N24

<400> SEQUENCE: 12

Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
            20                  25                  30

Tyr Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Val Asp Ile Ile
    50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
            85                  90                  95

Ile Ser Arg Leu Glu Gly Leu Ser Asn Leu Tyr Gln Ile Tyr Ala Glu
            100                 105                 110

Ser Phe Arg Ala Trp Glu Ala Asp Pro Thr Asn Pro Ala Leu Arg Val
        115                 120                 125
```

```
Glu Met Arg Ile Gln Phe Asn Asp Met Asn Ser Ala Leu Thr Thr Ala
130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Thr Thr Ile Asn Ser Arg
            180                 185                 190

Tyr Asn Asp Leu Thr Arg Leu Ile Gly Asn Tyr Thr Asp Tyr Ala Val
        195                 200                 205

Arg Trp Tyr Asn Thr Gly Leu Glu Arg Val Trp Gly Pro Asp Ser Arg
210                 215                 220

Asp Trp Ile Arg Tyr Asn Gln Phe Arg Arg Glu Leu Thr Leu Thr Val
225                 230                 235                 240

Leu Asp Ile Val Ser Leu Phe Ser Asn Tyr Asp Ser Arg Thr Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Met Ala Gln Arg Ile Glu
        275                 280                 285

Arg Ser Ile Arg Ser Pro His Leu Met Asp Ile Leu Asn Ser Ile Thr
290                 295                 300

Ile Tyr Thr Asp Val His Arg Gly Tyr Tyr Tyr Trp Ser Gly His Gln
305                 310                 315                 320

Ile Thr Ala Ser Pro Val Gly Phe Ser Gly Pro Glu Phe Ala Phe Pro
                325                 330                 335

Leu Tyr Gly Thr Met Gly Asn Ala Ala Pro Gln Gln Arg Ile Val Ala
            340                 345                 350

Gln Leu Gly Gln Gly Val Tyr Arg Thr Leu Ser Ser Thr Leu Tyr Arg
        355                 360                 365

Arg Pro Phe Asn Ile Gly Pro Asn Asn Gln Glu Leu Phe Val Leu Asp
370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Val Ile Pro Pro Gln
                405                 410                 415

Asn Asn Asn Val Pro Pro Arg Ala Gly Phe Ser His Arg Leu Ser His
            420                 425                 430

Val Ser Met Phe Arg Ser Gly Phe Ser Asn Ser Ser Val Ser Ile Ile
        435                 440                 445

Arg Ala Pro Met Phe Ser Trp Ile His Arg Ser Ala Glu Phe Asn Asn
450                 455                 460

Ile Ile Ala Ser Asp Ser Ile Thr Gln Ile Pro Ala Val Lys Gly Asn
465                 470                 475                 480

Phe Leu Phe Asn Gly Ser Val Ile Ser Gly Pro Gly Phe Thr Gly Gly
                485                 490                 495

Asp Leu Val Arg Leu Asn Ser Ser Gly Asn Asn Ile Gln Asn Arg Gly
            500                 505                 510

Tyr Ile Glu Val Pro Ile His Phe Pro Ser Thr Ser Thr Arg Tyr Arg
        515                 520                 525

Val Arg Val Arg Tyr Ala Ser Val Thr Pro Ile His Leu Asn Val Asn
530                 535                 540
```

```
Trp Gly Asn Ser Ser Ile Phe Ser Asn Thr Val Pro Ala Thr Ala Thr
545                 550                 555                 560

Ser Leu Asp Asn Leu Gln Ser Ser Asp Phe Gly Tyr Phe Glu Ser Ala
                565                 570                 575

Asn Ala Phe Thr Ser Ser Leu Gly Asn Ile Val Gly Val Arg Asn Phe
            580                 585                 590

Ser Gly Thr Ala Gly Val Ile Ile Asp Arg Phe Glu Phe Ile Pro Val
        595                 600                 605

Thr Ala Thr Leu Glu Ala Glu Tyr Asn Leu
    610                 615

<210> SEQ ID NO 13
<211> LENGTH: 618
<212> TYPE: PRT
<213> ORGANISM: Artificial Sequence
<220> FEATURE:
<223> OTHER INFORMATION: Mut-N27

<400> SEQUENCE: 13

Met Asp Asn Asn Pro Asn Ile Asn Glu Cys Ile Pro Tyr Asn Cys Leu
 1               5                  10                  15

Ser Asn Pro Glu Val Glu Val Leu Gly Gly Glu Arg Ile Glu Thr Gly
            20                  25                  30

Tyr Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Val Asp Ile Ile
    50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
            100                 105                 110

Ser Phe Arg Ala Trp Glu Ala Asp Pro Thr Asn Pro Ala Leu Arg Val
        115                 120                 125

Glu Met Arg Ile Gln Phe Asn Asp Met Asn Ser Ala Leu Thr Thr Ala
    130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Thr Thr Ile Asn Ser Arg
            180                 185                 190

Tyr Asn Asp Leu Thr Arg Leu Ile Gly Asn Tyr Thr Asp Tyr Ala Val
        195                 200                 205

Arg Trp Tyr Asn Thr Gly Leu Glu Arg Val Trp Gly Pro Asp Ser Arg
    210                 215                 220

Asp Trp Val Arg Tyr Asn Gln Phe Arg Arg Glu Leu Thr Leu Thr Val
225                 230                 235                 240

Leu Asp Ile Val Ser Leu Phe Ser Asn Tyr Asp Ser Arg Thr Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Met Ala Gln Arg Ile Glu
        275                 280                 285
```

```
Arg Ser Ile Arg Ser Pro His Leu Met Asp Ile Leu Asn Ser Ile Thr
    290                 295                 300
Ile Tyr Thr Asp Val His Arg Gly Tyr Tyr Trp Ser Gly His Gln
305                 310                 315                 320
Ile Thr Ala Ser Pro Val Gly Phe Ser Gly Pro Glu Phe Ala Phe Pro
                325                 330                 335
Leu Tyr Gly Thr Met Gly Asn Ala Ala Pro Gln Gln Arg Ile Val Ala
                340                 345                 350
Gln Leu Gly Gln Gly Val Tyr Arg Thr Leu Ser Ser Thr Leu Tyr Arg
            355                 360                 365
Arg Pro Phe Asn Ile Gly Pro Asn Asn Gln Glu Leu Phe Val Leu Asp
370                 375                 380
Gly Thr Glu Phe Ala Tyr Gly Thr Ser Ser Asn Leu Pro Ser Ala Val
385                 390                 395                 400
Tyr Arg Lys Ser Gly Thr Val Asp Ser Leu Asp Val Ile Pro Pro Gln
                405                 410                 415
Asp Asn Ser Val Pro Pro Arg Ala Gly Phe Ser His Arg Leu Ser His
                420                 425                 430
Val Ser Met Phe Arg Ser Gly Phe Ser Asn Ser Ser Val Ser Ile Ile
            435                 440                 445
Arg Ala Pro Met Phe Ser Trp Ile His Arg Ser Ala Glu Phe Asn Asn
450                 455                 460
Ile Ile Ala Ser Asp Ser Ile Thr Gln Ile Pro Ala Val Lys Gly Asn
465                 470                 475                 480
Phe Leu Phe Asn Gly Ser Val Ile Ser Gly Pro Gly Phe Thr Gly Gly
                485                 490                 495
Asp Leu Val Arg Leu Asn Ser Ser Gly Asn Asn Ile Gln Asn Arg Gly
                500                 505                 510
Tyr Ile Glu Val Pro Ile His Phe Pro Ser Thr Ser Thr Arg Tyr Arg
            515                 520                 525
Val Arg Val Arg Tyr Ala Ser Val Thr Pro Ile His Leu Asn Val Asn
530                 535                 540
Trp Gly Asn Ser Ser Ile Phe Ser Asn Thr Val Pro Ala Thr Ala Thr
545                 550                 555                 560
Ser Leu Asp Asn Leu Gln Ser Ser Asp Phe Gly Tyr Phe Glu Ser Ala
                565                 570                 575
Asn Ala Phe Thr Ser Ser Leu Gly Asn Ile Val Gly Val Arg Asn Phe
                580                 585                 590
Ser Gly Thr Ala Gly Val Ile Ile Asp Arg Phe Glu Phe Ile Pro Val
            595                 600                 605
Thr Ala Thr Leu Glu Ala Glu Tyr Asn Leu
610                 615

<210> SEQ ID NO 14
<211> LENGTH: 618
<212> TYPE: PRT
<213> ORGANISM: Artificial Sequence
<220> FEATURE:
<223> OTHER INFORMATION: Mut-N28

<400> SEQUENCE: 14

Met Asp Asn Asn Pro Asn Ile Asn Glu Cys Ile Pro Tyr Asn Cys Leu
 1               5                  10                  15
Ser Asn Pro Glu Val Glu Val Leu Gly Gly Glu Arg Ile Glu Thr Gly
            20                  25                  30
```

```
Tyr Thr Pro Ile Asp Ile Ser Leu Ser Leu Thr Gln Phe Leu Leu Ser
             35                  40                  45

Glu Phe Val Pro Gly Ala Gly Phe Val Leu Gly Leu Val Asp Ile Ile
 50                  55                  60

Trp Gly Ile Phe Gly Pro Ser Gln Trp Asp Ala Phe Leu Val Gln Ile
 65                  70                  75                  80

Glu Gln Leu Ile Asn Gln Arg Ile Glu Glu Phe Ala Arg Asn Gln Ala
                 85                  90                  95

Ile Ser Arg Leu Glu Gly Leu Ser Asn Leu Tyr Gln Ile Tyr Ala Glu
                100                 105                 110

Ser Phe Arg Glu Trp Glu Ala Asp Pro Thr Asn Pro Ala Leu Arg Glu
            115                 120                 125

Glu Met Arg Ile Gln Phe Asn Asp Met Asn Ser Ala Leu Thr Thr Ala
130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp Tyr Ala Val
            195                 200                 205

Arg Trp Tyr Asn Thr Gly Leu Glu Arg Val Trp Gly Pro Asp Ser Arg
210                 215                 220

Asp Trp Val Arg Tyr Asn Gln Phe Arg Arg Glu Leu Thr Leu Thr Val
225                 230                 235                 240

Leu Asp Ile Val Ser Leu Phe Ser Asn Tyr Asp Ser Arg Arg Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Met Ala Gln Arg Ile Glu
            275                 280                 285

Arg Ser Ile Arg Ser Pro His Leu Met Asp Ile Leu Asn Ser Ile Thr
290                 295                 300

Ile Tyr Thr Asp Val His Arg Gly Tyr Tyr Tyr Trp Ser Gly His Gln
305                 310                 315                 320

Ile Thr Ala Ser Pro Val Gly Phe Ser Gly Pro Glu Phe Ala Phe Pro
                325                 330                 335

Leu Phe Gly Asn Ala Gly Asn Ala Ala Pro Gln Gln Arg Ile Val Ala
            340                 345                 350

Gln Leu Gly Gln Gly Val Tyr Arg Thr Leu Ser Ser Thr Leu Tyr Arg
            355                 360                 365

Arg Pro Phe Asn Ile Gly Pro Asn Asn Gln Gln Leu Ser Val Leu Asp
370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Val Ile Pro Pro Gln
                405                 410                 415

Asn Asn Asn Val Pro Pro Arg Ala Gly Phe Ser His Arg Leu Ser His
            420                 425                 430

Val Ser Met Phe Arg Ser Gly Phe Ser Asn Ser Ser Val Ser Ile Ile
            435                 440                 445

Arg Ala Pro Met Phe Ser Trp Ile His Arg Ser Ala Glu Phe Asn Asn
```

```
                450                 455                 460
Ile Ile Ala Ser Asp Ser Ile Thr Gln Ile Pro Ala Val Lys Gly Asn
465                 470                 475                 480

Phe Leu Phe Asn Gly Ser Val Ile Ser Gly Pro Gly Phe Thr Gly Gly
                485                 490                 495

Asp Leu Val Arg Leu Asn Ser Ser Gly Asn Asn Ile Gln Asn Arg Gly
                500                 505                 510

Tyr Ile Glu Val Pro Ile His Phe Pro Ser Thr Ser Thr Arg Tyr Arg
            515                 520                 525

Val Arg Val Arg Tyr Ala Ser Val Thr Pro Ile His Leu Asn Val Asn
        530                 535                 540

Trp Gly Asn Ser Ser Ile Phe Ser Asn Thr Val Pro Ala Thr Ala Thr
545                 550                 555                 560

Ser Leu Asp Asn Leu Gln Ser Ser Asp Phe Gly Tyr Phe Glu Ser Ala
                565                 570                 575

Asn Ala Phe Thr Ser Ser Leu Gly Asn Ile Val Gly Val Arg Asn Phe
                580                 585                 590

Ser Gly Thr Ala Gly Val Ile Ile Asp Arg Phe Glu Phe Ile Pro Val
            595                 600                 605

Thr Ala Thr Leu Glu Ala Glu Tyr Asn Leu
            610                 615

<210> SEQ ID NO 15
<211> LENGTH: 618
<212> TYPE: PRT
<213> ORGANISM: Artificial Sequence
<220> FEATURE:
<223> OTHER INFORMATION: Mut-N29

<400> SEQUENCE: 15

Met Asp Asn Asn Pro Asn Ile Asn Glu Cys Ile Pro Tyr Asn Cys Leu
 1               5                  10                  15

Ser Asn Pro Glu Val Glu Val Leu Gly Gly Glu Arg Ile Glu Thr Gly
                20                  25                  30

Tyr Thr Pro Ile Asp Ile Ser Leu Ser Leu Thr Gln Phe Leu Leu Ser
            35                  40                  45

Glu Phe Val Pro Gly Ala Gly Phe Val Leu Gly Leu Val Asp Ile Ile
    50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Val
        115                 120                 125

Glu Met Arg Ile Gln Phe Asn Asp Met Asn Ser Ala Leu Thr Thr Ala
    130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Thr Thr Ile Asn Ser Arg
            180                 185                 190

Tyr Asn Asp Leu Thr Arg Leu Ile Gly Asn Tyr Thr Asp Tyr Ala Val
```

```
            195                 200                 205
Arg Trp Tyr Asn Thr Gly Leu Glu Arg Val Trp Gly Pro Asp Ser Arg
210                 215                 220

Asp Trp Val Arg Tyr Asn Gln Phe Arg Arg Glu Leu Thr Leu Thr Val
225                 230                 235                 240

Leu Asp Ile Val Ser Leu Phe Ser Asn Tyr Asp Ser Arg Arg Tyr Pro
                    245                 250                 255

Ile Arg Thr Val Ser Gln Leu Thr Arg Glu Ile Tyr Thr Asn Pro Val
                260                 265                 270

Leu Glu Asn Phe Asp Gly Ser Phe Arg Gly Met Ala Gln Arg Ile Glu
            275                 280                 285

Arg Ser Ile Arg Ser Pro His Leu Met Asp Ile Leu Asn Ser Ile Thr
290                 295                 300

Ile Tyr Thr Asp Val His Arg Gly Tyr Tyr Trp Ser Gly His Gln
305                 310                 315                 320

Ile Thr Ala Ser Pro Val Gly Phe Ser Gly Pro Glu Phe Ala Phe Pro
                    325                 330                 335

Leu Tyr Gly Thr Met Gly Asn Ala Ala Pro Gln Gln Arg Ile Val Ala
                340                 345                 350

Gln Leu Gly Gln Gly Val Tyr Arg Thr Leu Ser Ser Thr Leu Tyr Arg
            355                 360                 365

Arg Pro Phe Asn Ile Gly Pro Asn Asn Gln Leu Ser Val Leu Asp
370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Val Ile Pro Pro Gln
                    405                 410                 415

Asp Asn Ser Val Pro Pro Arg Ala Gly Phe Ser His Arg Leu Ser His
                420                 425                 430

Val Ser Met Phe Arg Ser Gly Phe Ser Asn Ser Ser Val Ser Ile Ile
            435                 440                 445

Arg Ala Pro Met Phe Ser Trp Ile His Arg Ser Ala Glu Phe Asn Asn
450                 455                 460

Ile Ile Ala Ser Asp Ser Ile Thr Gln Ile Pro Ala Val Lys Gly Asn
465                 470                 475                 480

Phe Leu Phe Asn Gly Ser Val Ile Ser Gly Pro Gly Phe Thr Gly Gly
                    485                 490                 495

Asp Leu Val Arg Leu Asn Ser Ser Gly Asn Asn Ile Gln Asn Arg Gly
                500                 505                 510

Tyr Ile Glu Val Pro Ile His Phe Pro Ser Thr Ser Thr Arg Tyr Arg
            515                 520                 525

Val Arg Val Arg Tyr Ala Ser Val Thr Pro Ile His Leu Asn Val Asn
530                 535                 540

Trp Gly Asn Ser Ser Ile Phe Ser Asn Thr Val Pro Ala Thr Ala Thr
545                 550                 555                 560

Ser Leu Asp Asn Leu Gln Ser Ser Asp Phe Gly Tyr Phe Glu Ser Ala
                    565                 570                 575

Asn Ala Phe Thr Ser Ser Leu Gly Asn Ile Val Gly Val Arg Asn Phe
                580                 585                 590

Ser Gly Thr Ala Gly Val Ile Ile Asp Arg Phe Glu Phe Ile Pro Val
            595                 600                 605

Thr Ala Thr Leu Glu Ala Glu Tyr Asn Leu
610                 615
```

<210> SEQ ID NO 16
<211> LENGTH: 618
<212> TYPE: PRT
<213> ORGANISM: Artificial Sequence
<220> FEATURE:
<223> OTHER INFORMATION: Mut-N31

<400> SEQUENCE: 16

```
Met Asp Asn Asn Pro Asn Ile Asn Glu Cys Ile Pro Tyr Asn Cys Leu
  1               5                  10                  15

Ser Asn Pro Glu Val Glu Val Leu Gly Gly Glu Arg Ile Glu Thr Gly
                 20                  25                  30

Tyr Thr Pro Ile Asp Ile Ser Leu Ser Leu Thr Gln Phe Leu Leu Ser
             35                  40                  45

Glu Phe Val Pro Gly Ala Gly Phe Val Leu Gly Leu Val Asp Ile Ile
         50                  55                  60

Trp Gly Ile Phe Gly Pro Ser Gln Trp Asp Ala Phe Leu Val Gln Ile
 65                  70                  75                  80

Glu Gln Leu Ile Asn Gln Arg Ile Glu Glu Phe Ala Arg Asn Gln Ala
                 85                  90                  95

Ile Ser Arg Leu Glu Gly Leu Ser Asn Leu Tyr Gln Ile Tyr Ala Glu
            100                 105                 110

Ser Phe Arg Ala Trp Glu Ala Asp Pro Thr Asn Pro Ala Leu Arg Glu
        115                 120                 125

Glu Met Arg Ile Gln Phe Asn Asp Met Asn Ser Ala Leu Thr Thr Ala
    130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Thr Thr Ile Asn Ser Arg
            180                 185                 190

Tyr Asn Asp Leu Thr Arg Leu Ile Gly Asn Tyr Thr Asp Tyr Ala Val
        195                 200                 205

Arg Trp Tyr Asn Thr Gly Leu Glu Arg Val Trp Gly Pro Asp Ser Arg
    210                 215                 220

Asp Trp Val Arg Tyr Asn Gln Phe Arg Arg Glu Leu Thr Leu Thr Val
225                 230                 235                 240

Leu Asp Ile Val Ser Leu Phe Ser Asn Tyr Asp Ser Arg Arg Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Met Ala Gln Arg Ile Glu
        275                 280                 285

Arg Ser Ile Arg Ser Pro His Leu Met Asp Ile Leu Asn Ser Ile Thr
    290                 295                 300

Ile Tyr Thr Asp Val His Arg Gly Tyr Tyr Tyr Trp Ser Gly His Gln
305                 310                 315                 320

Ile Thr Ala Ser Pro Val Gly Phe Ser Gly Pro Glu Phe Ala Phe Pro
                325                 330                 335

Leu Tyr Gly Thr Met Gly Asn Ala Ala Pro Gln Gln Arg Ile Val Ala
            340                 345                 350

Gln Leu Gly Gln Gly Val Tyr Arg Thr Leu Ser Ser Thr Leu Tyr Arg
        355                 360                 365
```

```
Arg Pro Phe Asn Ile Gly Pro Asn Asn Gln Glu Leu Phe Val Leu Asp
        370                 375                 380
Gly Thr Glu Phe Ala Tyr Gly Thr Ser Ser Asn Leu Pro Ser Ala Val
385                 390                 395                 400
Tyr Arg Lys Ser Gly Thr Val Asp Ser Leu Asp Val Ile Pro Pro Gln
            405                 410                 415
Asn Asn Asn Val Pro Pro Arg Ala Gly Phe Ser His Arg Leu Ser His
                420                 425                 430
Val Ser Met Phe Arg Ser Gly Phe Ser Asn Ser Ser Val Ser Ile Ile
            435                 440                 445
Arg Ala Pro Met Phe Ser Trp Ile His Arg Ser Ala Glu Phe Asn Asn
        450                 455                 460
Ile Ile Ala Ser Asp Ser Ile Thr Gln Ile Pro Ala Val Lys Gly Asn
465                 470                 475                 480
Phe Leu Phe Asn Gly Ser Val Ile Ser Gly Pro Gly Phe Thr Gly Gly
            485                 490                 495
Asp Leu Val Arg Leu Asn Ser Ser Gly Asn Asn Ile Gln Asn Arg Gly
                500                 505                 510
Tyr Ile Glu Val Pro Ile His Phe Pro Ser Thr Ser Thr Arg Tyr Arg
            515                 520                 525
Val Arg Val Arg Tyr Ala Ser Val Thr Pro Ile His Leu Asn Val Asn
        530                 535                 540
Trp Gly Asn Ser Ser Ile Phe Ser Asn Thr Val Pro Ala Thr Ala Thr
545                 550                 555                 560
Ser Leu Asp Asn Leu Gln Ser Ser Asp Phe Gly Tyr Phe Glu Ser Ala
                565                 570                 575
Asn Ala Phe Thr Ser Ser Leu Gly Asn Ile Val Gly Val Arg Asn Phe
            580                 585                 590
Ser Gly Thr Ala Gly Val Ile Ile Asp Arg Phe Glu Phe Ile Pro Val
        595                 600                 605
Thr Ala Thr Leu Glu Ala Glu Tyr Asn Leu
        610                 615

<210> SEQ ID NO 17
<211> LENGTH: 618
<212> TYPE: PRT
<213> ORGANISM: Artificial Sequence
<220> FEATURE:
<223> OTHER INFORMATION: Mut-N32

<400> SEQUENCE: 17

Met Asp Asn Asn Pro Asn Ile Asn Glu Cys Ile Pro Tyr Asn Cys Leu
  1               5                  10                  15
Ser Asn Pro Glu Val Glu Val Leu Gly Gly Glu Arg Ile Glu Thr Gly
                 20                  25                  30
Tyr Thr Pro Ile Asp Ile Ser Leu Ser Leu Thr Gln Phe Leu Leu Ser
             35                  40                  45
Glu Phe Val Pro Gly Ala Gly Phe Val Leu Gly Leu Val Asp Ile Ile
         50                  55                  60
Trp Gly Ile Phe Gly Pro Ser Gln Trp Asp Ala Phe Leu Val Gln Ile
 65                  70                  75                  80
Glu Gln Leu Ile Asn Gln Arg Ile Glu Glu Phe Ala Arg Asn Gln Ala
                 85                  90                  95
Ile Ser Arg Leu Glu Gly Leu Ser Asn Leu Tyr Gln Ile Tyr Ala Glu
                100                 105                 110
```

```
Ser Phe Arg Ala Trp Glu Ala Asp Pro Thr Asn Pro Ala Leu Arg Val
    115                 120                 125

Glu Met Arg Ile Gln Phe Asn Asp Met Asn Ser Ala Leu Thr Thr Ala
130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
                180                 185                 190

Tyr Asn Asp Leu Thr Arg Leu Ile Gly Asn Tyr Thr Asp Tyr Ala Val
                195                 200                 205

Arg Trp Tyr Asn Thr Gly Leu Glu Arg Val Trp Gly Pro Asp Ser Arg
210                 215                 220

Asp Trp Val Arg Tyr Asn Gln Phe Arg Arg Glu Leu Thr Leu Thr Val
225                 230                 235                 240

Leu Asp Ile Val Ala Leu Phe Ser Asn Tyr Asp Ser Arg Arg Tyr Pro
                245                 250                 255

Ile Arg Thr Val Ser Gln Leu Thr Arg Glu Ile Tyr Thr Asn Pro Val
                260                 265                 270

Leu Glu Asn Phe Asp Gly Ser Phe Arg Gly Met Ala Gln Arg Ile Glu
                275                 280                 285

Arg Ser Ile Arg Ser Pro His Leu Met Asp Ile Leu Asn Ser Ile Thr
                290                 295                 300

Ile Tyr Thr Asp Val His Arg Gly Tyr Tyr Trp Ser Gly His Gln
305                 310                 315                 320

Ile Thr Ala Ser Pro Val Gly Phe Ser Gly Pro Glu Phe Ala Phe Pro
                325                 330                 335

Leu Tyr Gly Thr Met Gly Asn Ala Ala Pro Gln Gln Arg Ile Val Ala
                340                 345                 350

Gln Leu Gly Gln Gly Val Tyr Arg Thr Leu Ser Ser Thr Leu Tyr Arg
                355                 360                 365

Arg Pro Phe Asn Ile Gly Pro Asn Asn Gln Gln Leu Ser Val Leu Asp
370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Val Ile Pro Pro Gln
                405                 410                 415

Asn Asn Asn Val Pro Pro Arg Ala Gly Phe Ser His Arg Leu Ser His
                420                 425                 430

Val Ser Met Phe Arg Ser Gly Phe Ser Asn Ser Ser Val Ser Ile Ile
                435                 440                 445

Arg Ala Pro Met Phe Ser Trp Ile His Arg Ser Ala Glu Phe Asn Asn
450                 455                 460

Ile Ile Ala Ser Asp Ser Ile Thr Gln Ile Pro Ala Val Lys Gly Asn
465                 470                 475                 480

Phe Leu Phe Asn Gly Ser Val Ile Ser Gly Pro Gly Phe Thr Gly Gly
                485                 490                 495

Asp Leu Val Arg Leu Asn Ser Ser Gly Asn Asn Ile Gln Asn Arg Gly
                500                 505                 510

Tyr Ile Glu Val Pro Ile His Phe Pro Ser Thr Ser Thr Arg Tyr Arg
                515                 520                 525
```

```
Val Arg Val Arg Tyr Ala Ser Val Thr Pro Ile His Leu Asn Val Asn
    530                 535                 540

Trp Gly Asn Ser Ser Ile Phe Ser Asn Thr Val Pro Ala Thr Ala Thr
545                 550                 555                 560

Ser Leu Asp Asn Leu Gln Ser Ser Asp Phe Gly Tyr Phe Glu Ser Ala
                565                 570                 575

Asn Ala Phe Thr Ser Ser Leu Gly Asn Ile Val Gly Val Arg Asn Phe
            580                 585                 590

Ser Gly Thr Ala Gly Val Ile Ile Asp Arg Phe Glu Phe Ile Pro Val
        595                 600                 605

Thr Ala Thr Leu Glu Ala Glu Tyr Asn Leu
    610                 615
```

<210> SEQ ID NO 18
<211> LENGTH: 618
<212> TYPE: PRT
<213> ORGANISM: Artificial Sequence
<220> FEATURE:
<223> OTHER INFORMATION: Mut-N33

<400> SEQUENCE: 18

```
Met Asp Asn Asn Pro Asn Ile Asn Glu Cys Ile Pro Tyr Asn Cys Leu
  1               5                  10                  15

Ser Asn Pro Glu Val Glu Val Leu Gly Gly Glu Arg Ile Glu Thr Gly
                 20                  25                  30

Tyr Thr Pro Ile Asp Ile Ser Leu Ser Leu Thr Gln Phe Leu Leu Ser
             35                  40                  45

Glu Phe Val Pro Gly Ala Gly Phe Val Leu Gly Leu Val Asp Ile Ile
         50                  55                  60

Trp Gly Ile Phe Gly Pro Ser Gln Trp Asp Ala Phe Leu Val Gln Ile
 65                  70                  75                  80

Glu Gln Leu Ile Asn Gln Arg Ile Glu Glu Phe Ala Arg Asn Gln Ala
                 85                  90                  95

Ile Ser Arg Leu Glu Gly Leu Ser Asn Leu Tyr Gln Ile Tyr Ala Glu
            100                 105                 110

Ser Phe Arg Ala Trp Glu Ala Asp Pro Thr Asn Pro Ala Leu Arg Glu
        115                 120                 125

Glu Met Arg Ile Gln Phe Asn Asp Met Asn Ser Ala Leu Thr Thr Ala
    130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp Tyr Ala Val
        195                 200                 205

Arg Trp Tyr Asn Thr Gly Leu Glu Arg Val Trp Gly Pro Asp Ser Arg
    210                 215                 220

Asp Trp Val Arg Tyr Asn Gln Phe Arg Arg Glu Leu Thr Leu Thr Val
225                 230                 235                 240

Leu Asp Ile Val Ala Leu Phe Ser Asn Tyr Asp Ser Arg Arg Tyr Pro
                245                 250                 255

Ile Arg Thr Val Ser Gln Leu Thr Arg Glu Ile Tyr Thr Asn Pro Val
            260                 265                 270
```

```
Leu Glu Asn Phe Asp Gly Ser Phe Arg Gly Met Ala Gln Arg Ile Glu
            275                 280                 285

Arg Ser Ile Arg Ser Pro His Leu Met Asp Ile Leu Asn Ser Ile Thr
        290                 295                 300

Ile Tyr Thr Asp Val His Arg Gly Tyr Tyr Trp Ser Gly His Gln
305                 310                 315                 320

Ile Thr Ala Ser Pro Val Gly Phe Ser Gly Pro Glu Phe Ala Phe Pro
                325                 330                 335

Leu Phe Gly Asn Ala Gly Asn Ala Ala Pro Gln Gln Arg Ile Val Ala
            340                 345                 350

Gln Leu Gly Gln Gly Val Tyr Arg Thr Leu Ser Ser Thr Leu Tyr Arg
        355                 360                 365

Arg Pro Phe Asn Ile Gly Pro Asn Asn Gln Gln Leu Ser Val Leu Asp
    370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Val Ile Pro Pro Gln
                405                 410                 415

Asn Asn Asn Val Pro Pro Arg Ala Gly Phe Ser His Arg Leu Ser His
            420                 425                 430

Val Ser Met Phe Arg Ser Gly Phe Ser Asn Ser Ser Val Ser Ile Ile
        435                 440                 445

Arg Ala Pro Met Phe Ser Trp Ile His Arg Ser Ala Glu Phe Asn Asn
    450                 455                 460

Ile Ile Ala Ser Asp Ser Ile Thr Gln Ile Pro Ala Val Lys Gly Asn
465                 470                 475                 480

Phe Leu Phe Asn Gly Ser Val Ile Ser Gly Pro Gly Phe Thr Gly Gly
                485                 490                 495

Asp Leu Val Arg Leu Asn Ser Ser Gly Asn Asn Ile Gln Asn Arg Gly
            500                 505                 510

Tyr Ile Glu Val Pro Ile His Phe Pro Ser Thr Ser Thr Arg Tyr Arg
        515                 520                 525

Val Arg Val Arg Tyr Ala Ser Val Thr Pro Ile His Leu Asn Val Asn
    530                 535                 540

Trp Gly Asn Ser Ser Ile Phe Ser Asn Thr Val Pro Ala Thr Ala Thr
545                 550                 555                 560

Ser Leu Asp Asn Leu Gln Ser Ser Asp Phe Gly Tyr Phe Glu Ser Ala
                565                 570                 575

Asn Ala Phe Thr Ser Ser Leu Gly Asn Ile Val Gly Val Arg Asn Phe
            580                 585                 590

Ser Gly Thr Ala Gly Val Ile Ile Asp Arg Phe Glu Phe Ile Pro Val
        595                 600                 605

Thr Ala Thr Leu Glu Ala Glu Tyr Asn Leu
    610                 615

<210> SEQ ID NO 19
<211> LENGTH: 618
<212> TYPE: PRT
<213> ORGANISM: Artificial Sequence
<220> FEATURE:
<223> OTHER INFORMATION: Mut-N35

<400> SEQUENCE: 19

Met Asp Asn Asn Pro Asn Ile Asn Glu Cys Ile Pro Tyr Asn Cys Leu
1               5                   10                  15
```

```
Ser Asn Pro Glu Val Glu Val Leu Gly Gly Glu Arg Ile Glu Thr Gly
             20                  25                  30

Tyr Thr Pro Ile Asp Ile Ser Leu Ser Leu Thr Gln Phe Leu Leu Ser
         35                  40                  45

Glu Phe Val Pro Gly Ala Gly Phe Val Leu Gly Leu Val Asp Ile Ile
 50                  55                  60

Trp Gly Ile Phe Gly Pro Ser Gln Trp Asp Ala Phe Leu Val Gln Ile
 65                  70                  75                  80

Glu Gln Leu Ile Asn Gln Arg Ile Glu Phe Ala Arg Asn Gln Ala
                 85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
        115                 120                 125

Glu Met Arg Ile Gln Phe Asn Asp Met Asn Ser Ala Leu Thr Thr Ala
130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Thr Thr Ile Asn Ser Arg
            180                 185                 190

Tyr Asn Asp Leu Thr Arg Leu Ile Gly Asn Tyr Thr Asp Tyr Ala Val
        195                 200                 205

Arg Trp Tyr Asn Thr Gly Leu Glu Arg Val Trp Gly Pro Asp Ser Arg
210                 215                 220

Asp Trp Val Arg Tyr Asn Gln Phe Arg Arg Glu Leu Thr Leu Thr Val
225                 230                 235                 240

Leu Asp Ile Val Ala Leu Phe Ser Asn Tyr Asp Ser Arg Arg Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Met Ala Gln Arg Ile Glu
        275                 280                 285

Arg Ser Ile Arg Ser Pro His Leu Met Asp Ile Leu Asn Ser Ile Thr
290                 295                 300

Ile Tyr Thr Asp Val His Arg Gly Tyr Tyr Tyr Trp Ser Gly His Gln
305                 310                 315                 320

Ile Thr Ala Ser Pro Val Gly Phe Ser Gly Pro Glu Phe Ala Phe Pro
                325                 330                 335

Leu Phe Gly Asn Ala Gly Asn Ala Ala Pro Gln Gln Arg Ile Val Ala
            340                 345                 350

Gln Leu Gly Gln Gly Val Tyr Arg Thr Leu Ser Ser Thr Leu Tyr Arg
        355                 360                 365

Arg Pro Phe Asn Ile Gly Pro Asn Asn Gln Gln Leu Ser Val Leu Asp
370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Val Ile Pro Pro Gln
                405                 410                 415

Asp Asn Ser Val Pro Pro Arg Ala Gly Phe Ser His Arg Leu Ser His
            420                 425                 430

Val Ser Met Phe Arg Ser Gly Phe Ser Asn Ser Ser Val Ser Ile Ile
```

```
            435                 440                 445
Arg Ala Pro Met Phe Ser Trp Ile His Arg Ser Ala Glu Phe Asn Asn
450                 455                 460

Ile Ile Ala Ser Asp Ser Ile Thr Gln Ile Pro Ala Val Lys Gly Asn
465                 470                 475                 480

Phe Leu Phe Asn Gly Ser Val Ile Ser Gly Pro Gly Phe Thr Gly Gly
                485                 490                 495

Asp Leu Val Arg Leu Asn Ser Ser Gly Asn Asn Ile Gln Asn Arg Gly
            500                 505                 510

Tyr Ile Glu Val Pro Ile His Phe Pro Ser Thr Ser Thr Arg Tyr Arg
        515                 520                 525

Val Arg Val Arg Tyr Ala Ser Val Thr Pro Ile His Leu Asn Val Asn
    530                 535                 540

Trp Gly Asn Ser Ser Ile Phe Ser Asn Thr Val Pro Ala Thr Ala Thr
545                 550                 555                 560

Ser Leu Asp Asn Leu Gln Ser Ser Asp Phe Gly Tyr Phe Glu Ser Ala
                565                 570                 575

Asn Ala Phe Thr Ser Ser Leu Gly Asn Ile Val Gly Val Arg Asn Phe
            580                 585                 590

Ser Gly Thr Ala Gly Val Ile Ile Asp Arg Phe Glu Phe Ile Pro Val
        595                 600                 605

Thr Ala Thr Leu Glu Ala Glu Tyr Asn Leu
    610                 615

<210> SEQ ID NO 20
<211> LENGTH: 618
<212> TYPE: PRT
<213> ORGANISM: Artificial Sequence
<220> FEATURE:
<223> OTHER INFORMATION: Mut-N37

<400> SEQUENCE: 20

Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
                20                  25                  30

Tyr Thr Pro Ile Asp Ile Ser Leu Ser Leu Thr Gln Phe Leu Leu Ser
            35                  40                  45

Glu Phe Val Pro Gly Ala Gly Phe Val Leu Gly Leu Val Asp Ile Ile
        50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Val
        115                 120                 125

Glu Met Arg Ile Gln Phe Asn Asp Met Asn Ser Ala Leu Thr Thr Ala
    130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Thr Thr Ile Asn Ser Arg
```

```
                180              185              190
Tyr Asn Asp Leu Thr Arg Leu Ile Gly Asn Tyr Thr Asp Tyr Ala Val
        195                 200                 205
Arg Trp Tyr Asn Thr Gly Leu Glu Arg Val Trp Gly Pro Asp Ser Arg
        210                 215                 220
Asp Trp Ile Arg Tyr Asn Gln Phe Arg Arg Glu Leu Thr Leu Thr Val
225                 230                 235                 240
Leu Asp Ile Val Ser Leu Phe Ser Asn Tyr Asp Ser Arg Arg Tyr Pro
                245                 250                 255
Ile Arg Thr Val Ser Gln Leu Thr Arg Glu Ile Tyr Thr Asn Pro Val
        260                 265                 270
Leu Glu Asn Phe Asp Gly Ser Phe Arg Gly Met Ala Gln Arg Ile Glu
        275                 280                 285
Arg Ser Ile Arg Ser Pro His Leu Met Asp Ile Leu Asn Ser Ile Thr
        290                 295                 300
Ile Tyr Thr Asp Val His Arg Gly Tyr Tyr Trp Ser Gly His Gln
305                 310                 315                 320
Ile Thr Ala Ser Pro Val Gly Phe Ser Gly Pro Glu Phe Ala Phe Pro
                325                 330                 335
Leu Tyr Gly Thr Met Gly Asn Ala Ala Pro Gln Gln Arg Ile Val Ala
                340                 345                 350
Gln Leu Gly Gln Gly Val Tyr Arg Thr Leu Ser Ser Thr Leu Tyr Arg
        355                 360                 365
Arg Pro Phe Asn Ile Gly Pro Asn Asn Gln Glu Leu Phe Val Leu Asp
        370                 375                 380
Gly Thr Glu Phe Ala Tyr Gly Thr Ser Ser Asn Leu Pro Ser Ala Val
385                 390                 395                 400
Tyr Arg Lys Ser Gly Thr Val Asp Ser Leu Asp Val Ile Pro Pro Gln
                405                 410                 415
Asp Asn Ser Val Pro Pro Arg Ala Gly Phe Ser His Arg Leu Ser His
                420                 425                 430
Val Ser Met Phe Arg Ser Gly Phe Ser Asn Ser Ser Val Ser Ile Ile
        435                 440                 445
Arg Ala Pro Met Phe Ser Trp Ile His Arg Ser Ala Glu Phe Asn Asn
        450                 455                 460
Ile Ile Ala Ser Asp Ser Ile Thr Gln Ile Pro Ala Val Lys Gly Asn
465                 470                 475                 480
Phe Leu Phe Asn Gly Ser Val Ile Ser Gly Pro Gly Phe Thr Gly Gly
                485                 490                 495
Asp Leu Val Arg Leu Asn Ser Ser Gly Asn Asn Ile Gln Asn Arg Gly
                500                 505                 510
Tyr Ile Glu Val Pro Ile His Phe Pro Ser Thr Ser Thr Arg Tyr Arg
        515                 520                 525
Val Arg Val Arg Tyr Ala Ser Val Thr Pro Ile His Leu Asn Val Asn
        530                 535                 540
Trp Gly Asn Ser Ser Ile Phe Ser Asn Thr Val Pro Ala Thr Ala Thr
545                 550                 555                 560
Ser Leu Asp Asn Leu Gln Ser Ser Asp Phe Gly Tyr Phe Glu Ser Ala
                565                 570                 575
Asn Ala Phe Thr Ser Ser Leu Gly Asn Ile Val Gly Val Arg Asn Phe
                580                 585                 590
Ser Gly Thr Ala Gly Val Ile Ile Asp Arg Phe Glu Phe Ile Pro Val
        595                 600                 605
```

```
Thr Ala Thr Leu Glu Ala Glu Tyr Asn Leu
        610             615
```

<210> SEQ ID NO 21
<211> LENGTH: 618
<212> TYPE: PRT
<213> ORGANISM: Artificial Sequence
<220> FEATURE:
<223> OTHER INFORMATION: Mut-N38

<400> SEQUENCE: 21

```
Met Asp Asn Asn Pro Asn Ile Asn Glu Cys Ile Pro Tyr Asn Cys Leu
  1               5                  10                  15

Ser Asn Pro Glu Val Glu Val Leu Gly Gly Glu Arg Ile Glu Thr Gly
             20                  25                  30

Tyr Thr Pro Ile Asp Ile Ser Leu Ser Leu Thr Gln Phe Leu Leu Ser
         35                  40                  45

Glu Phe Val Pro Gly Ala Gly Phe Val Leu Gly Leu Val Asp Ile Ile
     50                  55                  60

Trp Gly Ile Phe Gly Pro Ser Gln Trp Asp Ala Phe Leu Val Gln Ile
 65                  70                  75                  80

Glu Gln Leu Ile Asn Gln Arg Ile Glu Glu Phe Ala Arg Asn Gln Ala
                 85                  90                  95

Ile Ser Arg Leu Glu Gly Leu Ser Asn Leu Tyr Gln Ile Tyr Ala Glu
            100                 105                 110

Ser Phe Arg Ala Trp Glu Ala Asp Pro Thr Asn Pro Ala Leu Arg Val
        115                 120                 125

Glu Met Arg Ile Gln Phe Asn Asp Met Asn Ser Ala Leu Thr Thr Ala
    130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Thr Thr Ile Asn Ser Arg
            180                 185                 190

Tyr Asn Asp Leu Thr Arg Leu Ile Gly Asn Tyr Thr Asp Tyr Ala Val
        195                 200                 205

Arg Trp Tyr Asn Thr Gly Leu Glu Arg Val Trp Gly Pro Asp Ser Arg
    210                 215                 220

Asp Trp Ile Arg Tyr Asn Gln Phe Arg Arg Glu Leu Thr Leu Thr Val
225                 230                 235                 240

Leu Asp Ile Val Ser Leu Phe Ser Asn Tyr Asp Ser Arg Thr Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Met Ala Gln Arg Ile Glu
        275                 280                 285

Arg Ser Ile Arg Ser Pro His Leu Met Asp Ile Leu Asn Ser Ile Thr
    290                 295                 300

Ile Tyr Thr Asp Val His Arg Gly Tyr Tyr Trp Ser Gly His Gln
305                 310                 315                 320

Ile Thr Ala Ser Pro Val Gly Phe Ser Gly Pro Glu Phe Ala Phe Pro
                325                 330                 335

Leu Tyr Gly Thr Met Gly Asn Ala Ala Pro Gln Gln Arg Ile Val Ala
            340                 345                 350
```

```
Gln Leu Gly Gln Gly Val Tyr Arg Thr Leu Ser Ser Thr Leu Tyr Arg
        355                 360                 365

Arg Pro Phe Asn Ile Gly Pro Asn Asn Gln Gln Leu Ser Val Leu Asp
370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Val Ile Pro Pro Gln
                405                 410                 415

Asp Asn Ser Val Pro Pro Arg Ala Gly Phe Ser His Arg Leu Ser His
            420                 425                 430

Val Ser Met Phe Arg Ser Gly Phe Ser Asn Ser Val Ser Ile Ile
            435                 440                 445

Arg Ala Pro Met Phe Ser Trp Ile His Arg Ser Ala Glu Phe Asn Asn
450                 455                 460

Ile Ile Ala Ser Asp Ser Ile Thr Gln Ile Pro Ala Val Lys Gly Asn
465                 470                 475                 480

Phe Leu Phe Asn Gly Ser Val Ile Ser Gly Pro Gly Phe Thr Gly Gly
                485                 490                 495

Asp Leu Val Arg Leu Asn Ser Ser Gly Asn Asn Ile Asn Arg Gly
            500                 505                 510

Tyr Ile Glu Val Pro Ile His Phe Pro Ser Thr Ser Thr Arg Tyr Arg
            515                 520                 525

Val Arg Val Arg Tyr Ala Ser Val Thr Pro Ile His Leu Asn Val Asn
            530                 535                 540

Trp Gly Asn Ser Ser Ile Phe Ser Asn Thr Val Pro Ala Thr Ala Thr
545                 550                 555                 560

Ser Leu Asp Asn Leu Gln Ser Ser Asp Phe Gly Tyr Phe Glu Ser Ala
                565                 570                 575

Asn Ala Phe Thr Ser Ser Leu Gly Asn Ile Val Gly Val Arg Asn Phe
            580                 585                 590

Ser Gly Thr Ala Gly Val Ile Ile Asp Arg Phe Glu Phe Ile Pro Val
            595                 600                 605

Thr Ala Thr Leu Glu Ala Glu Tyr Asn Leu
    610                 615

<210> SEQ ID NO 22
<211> LENGTH: 618
<212> TYPE: PRT
<213> ORGANISM: Artificial Sequence
<220> FEATURE:
<223> OTHER INFORMATION: Mut-N39

<400> SEQUENCE: 22

Met Asp Asn Asn Pro Asn Ile Asn Glu Cys Ile Pro Tyr Asn Cys Leu
 1               5                  10                  15

Ser Asn Pro Glu Val Glu Val Leu Gly Gly Glu Arg Ile Glu Thr Gly
                20                  25                  30

Tyr Thr Pro Ile Asp Ile Ser Leu Ser Leu Thr Gln Phe Leu Leu Ser
                35                  40                  45

Glu Phe Val Pro Gly Ala Gly Phe Val Leu Gly Leu Val Asp Ile Ile
        50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
                85                  90                  95
```

-continued

```
Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
            115                 120                 125

Glu Met Arg Ile Gln Phe Asn Asp Met Asn Ser Ala Leu Thr Thr Ala
            130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Thr Thr Ile Asn Ser Arg
            180                 185                 190

Tyr Asn Asp Leu Thr Arg Leu Ile Gly Asn Tyr Thr Asp Tyr Ala Val
            195                 200                 205

Arg Trp Tyr Asn Thr Gly Leu Glu Arg Val Trp Gly Pro Asp Ser Arg
210                 215                 220

Asp Trp Val Arg Tyr Asn Gln Phe Arg Arg Glu Leu Thr Leu Thr Val
225                 230                 235                 240

Leu Asp Ile Val Ala Leu Phe Ser Asn Tyr Asp Ser Arg Arg Tyr Pro
            245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Met Ala Gln Arg Ile Glu
            275                 280                 285

Arg Ser Ile Arg Ser Pro His Leu Met Asp Ile Leu Asn Ser Ile Thr
290                 295                 300

Ile Tyr Thr Asp Val His Arg Gly Tyr Tyr Trp Ser Gly His Gln
305                 310                 315                 320

Ile Thr Ala Ser Pro Val Gly Phe Ser Gly Pro Glu Phe Ala Phe Pro
            325                 330                 335

Leu Tyr Gly Thr Met Gly Asn Ala Ala Pro Gln Gln Arg Ile Val Ala
            340                 345                 350

Gln Leu Gly Gln Gly Val Tyr Arg Thr Leu Ser Thr Leu Tyr Arg
            355                 360                 365

Arg Pro Phe Asn Ile Gly Pro Asn Asn Gln Gln Leu Ser Val Leu Asp
370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Val Ile Pro Pro Gln
                405                 410                 415

Asp Asn Ser Val Pro Pro Arg Ala Gly Phe Ser His Arg Leu Ser His
            420                 425                 430

Val Ser Met Phe Arg Ser Gly Phe Ser Asn Ser Ser Val Ser Ile Ile
            435                 440                 445

Arg Ala Pro Met Phe Ser Trp Ile His Arg Ser Ala Glu Phe Asn Asn
            450                 455                 460

Ile Ile Ala Ser Asp Ser Ile Thr Gln Ile Pro Ala Val Lys Gly Asn
465                 470                 475                 480

Phe Leu Phe Asn Gly Ser Val Ile Ser Gly Pro Gly Phe Thr Gly Gly
                485                 490                 495

Asp Leu Val Arg Leu Asn Ser Ser Gly Asn Asn Ile Gln Asn Arg Gly
            500                 505                 510
```

```
Tyr Ile Glu Val Pro Ile His Phe Pro Ser Thr Ser Thr Arg Tyr Arg
            515                 520                 525

Val Arg Val Arg Tyr Ala Ser Val Thr Pro Ile His Leu Asn Val Asn
530                 535                 540

Trp Gly Asn Ser Ser Ile Phe Ser Asn Thr Val Pro Ala Thr Ala Thr
545                 550                 555                 560

Ser Leu Asp Asn Leu Gln Ser Ser Asp Phe Gly Tyr Phe Glu Ser Ala
                565                 570                 575

Asn Ala Phe Thr Ser Ser Leu Gly Asn Ile Val Gly Val Arg Asn Phe
            580                 585                 590

Ser Gly Thr Ala Gly Val Ile Ile Asp Arg Phe Glu Phe Ile Pro Val
        595                 600                 605

Thr Ala Thr Leu Glu Ala Glu Tyr Asn Leu
        610                 615

<210> SEQ ID NO 23
<211> LENGTH: 618
<212> TYPE: PRT
<213> ORGANISM: Artificial Sequence
<220> FEATURE:
<223> OTHER INFORMATION: Mut-N40

<400> SEQUENCE: 23

Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
            20                  25                  30

Tyr Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Val Asp Ile Ile
    50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
        115                 120                 125

Glu Met Arg Ile Gln Phe Asn Asp Met Asn Ser Ala Leu Thr Thr Ala
    130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp Tyr Ala Val
        195                 200                 205

Arg Trp Tyr Asn Thr Gly Leu Glu Arg Val Trp Gly Pro Asp Ser Arg
    210                 215                 220

Asp Trp Val Arg Tyr Asn Gln Phe Arg Arg Glu Leu Thr Leu Thr Val
225                 230                 235                 240

Leu Asp Ile Val Ser Leu Phe Ser Asn Tyr Asp Ser Arg Arg Tyr Pro
                245                 250                 255
```

```
Ile Arg Thr Val Ser Gln Leu Thr Arg Glu Ile Tyr Thr Asn Pro Val
            260                 265                 270

Leu Glu Asn Phe Asp Gly Ser Phe Arg Gly Met Ala Gln Arg Ile Glu
        275                 280                 285

Arg Ser Ile Arg Ser Pro His Leu Met Asp Ile Leu Asn Ser Ile Thr
    290                 295                 300

Ile Tyr Thr Asp Val His Arg Gly Tyr Tyr Trp Ser Gly His Gln
305                 310                 315                 320

Ile Thr Ala Ser Pro Val Gly Phe Ser Gly Pro Glu Phe Ala Phe Pro
                325                 330                 335

Leu Tyr Gly Thr Met Gly Asn Ala Ala Pro Gln Gln Arg Ile Val Ala
            340                 345                 350

Gln Leu Gly Gln Gly Val Tyr Arg Thr Leu Ser Ser Thr Leu Tyr Arg
        355                 360                 365

Arg Pro Phe Asn Ile Gly Pro Asn Asn Gln Glu Leu Phe Val Leu Asp
    370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Val Ile Pro Pro Gln
                405                 410                 415

Asn Asn Asn Val Pro Pro Arg Ala Gly Phe Ser His Arg Leu Ser His
            420                 425                 430

Val Ser Met Phe Arg Ser Gly Phe Ser Asn Ser Ser Val Ser Ile Ile
        435                 440                 445

Arg Ala Pro Met Phe Ser Trp Ile His Arg Ser Ala Glu Phe Asn Asn
    450                 455                 460

Ile Ile Ala Ser Asp Ser Ile Thr Gln Ile Pro Ala Val Lys Gly Asn
465                 470                 475                 480

Phe Leu Phe Asn Gly Ser Val Ile Ser Gly Pro Gly Phe Thr Gly Gly
                485                 490                 495

Asp Leu Val Arg Leu Asn Ser Ser Gly Asn Asn Ile Gln Asn Arg Gly
            500                 505                 510

Tyr Ile Glu Val Pro Ile His Phe Pro Ser Thr Ser Thr Arg Tyr Arg
        515                 520                 525

Val Arg Val Arg Tyr Ala Ser Val Thr Pro Ile His Leu Asn Val Asn
    530                 535                 540

Trp Gly Asn Ser Ser Ile Phe Ser Asn Thr Val Pro Ala Thr Ala Thr
545                 550                 555                 560

Ser Leu Asp Asn Leu Gln Ser Ser Asp Phe Gly Tyr Phe Glu Ser Ala
                565                 570                 575

Asn Ala Phe Thr Ser Ser Leu Gly Asn Ile Val Gly Val Arg Asn Phe
            580                 585                 590

Ser Gly Thr Ala Gly Val Ile Ile Asp Arg Phe Glu Phe Ile Pro Val
        595                 600                 605

Thr Ala Thr Leu Glu Ala Glu Tyr Asn Leu
    610                 615

<210> SEQ ID NO 24
<211> LENGTH: 618
<212> TYPE: PRT
<213> ORGANISM: Artificial Sequence
<220> FEATURE:
<223> OTHER INFORMATION: Mut-N41

<400> SEQUENCE: 24
```

```
Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
            20                  25                  30

Tyr Thr Pro Ile Asp Ile Ser Leu Ser Leu Thr Gln Phe Leu Leu Ser
            35                  40                  45

Glu Phe Val Pro Gly Ala Gly Phe Val Leu Gly Leu Val Asp Ile Ile
        50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
                100                 105                 110

Ser Phe Arg Ala Trp Glu Ala Asp Pro Thr Asn Pro Ala Leu Arg Glu
            115                 120                 125

Glu Met Arg Ile Gln Phe Asn Asp Met Asn Ser Ala Leu Thr Thr Ala
        130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Thr Thr Ile Asn Ser Arg
            180                 185                 190

Tyr Asn Asp Leu Thr Arg Leu Ile Gly Asn Tyr Thr Asp Tyr Ala Val
            195                 200                 205

Arg Trp Tyr Asn Thr Gly Leu Glu Arg Val Trp Gly Pro Asp Ser Arg
        210                 215                 220

Asp Trp Val Arg Tyr Asn Gln Phe Arg Arg Glu Leu Thr Leu Thr Val
225                 230                 235                 240

Leu Asp Ile Val Ser Leu Phe Ser Asn Tyr Asp Ser Arg Arg Tyr Pro
                245                 250                 255

Ile Arg Thr Val Ser Gln Leu Thr Arg Glu Ile Tyr Thr Asn Pro Val
                260                 265                 270

Leu Glu Asn Phe Asp Gly Ser Phe Arg Gly Met Ala Gln Arg Ile Glu
            275                 280                 285

Arg Ser Ile Arg Ser Pro His Leu Met Asp Ile Leu Asn Ser Ile Thr
        290                 295                 300

Ile Tyr Thr Asp Val His Arg Gly Tyr Tyr Trp Ser Gly His Gln
305                 310                 315                 320

Ile Thr Ala Ser Pro Val Gly Phe Ser Gly Pro Glu Phe Ala Phe Pro
            325                 330                 335

Leu Tyr Gly Thr Met Gly Asn Ala Ala Pro Gln Gln Arg Ile Val Ala
            340                 345                 350

Gln Leu Gly Gln Gly Val Tyr Arg Thr Leu Ser Ser Thr Leu Tyr Arg
        355                 360                 365

Arg Pro Phe Asn Ile Gly Pro Asn Asn Gln Gln Leu Ser Val Leu Asp
    370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Val Ile Pro Pro Gln
                405                 410                 415

Asp Asn Ser Val Pro Pro Arg Ala Gly Phe Ser His Arg Leu Ser His
```

```
            420             425             430
Val Ser Met Phe Arg Ser Gly Phe Ser Asn Ser Val Ser Ile Ile
        435             440             445

Arg Ala Pro Met Phe Ser Trp Ile His Arg Ser Ala Glu Phe Asn Asn
450             455             460

Ile Ile Ala Ser Asp Ser Ile Thr Gln Ile Pro Ala Val Lys Gly Asn
465             470             475             480

Phe Leu Phe Asn Gly Ser Val Ile Ser Gly Pro Gly Phe Thr Gly Gly
                485             490             495

Asp Leu Val Arg Leu Asn Ser Ser Gly Asn Asn Ile Gln Asn Arg Gly
                500             505             510

Tyr Ile Glu Val Pro Ile His Phe Pro Ser Thr Ser Thr Arg Tyr Arg
        515             520             525

Val Arg Val Arg Tyr Ala Ser Val Thr Pro Ile His Leu Asn Val Asn
530             535             540

Trp Gly Asn Ser Ser Ile Phe Ser Asn Thr Val Pro Ala Thr Ala Thr
545             550             555             560

Ser Leu Asp Asn Leu Gln Ser Ser Asp Phe Gly Tyr Phe Glu Ser Ala
                565             570             575

Asn Ala Phe Thr Ser Ser Leu Gly Asn Ile Val Gly Val Arg Asn Phe
                580             585             590

Ser Gly Thr Ala Gly Val Ile Ile Asp Arg Phe Glu Phe Ile Pro Val
        595             600             605

Thr Ala Thr Leu Glu Ala Glu Tyr Asn Leu
        610             615

<210> SEQ ID NO 25
<211> LENGTH: 618
<212> TYPE: PRT
<213> ORGANISM: Artificial Sequence
<220> FEATURE:
<223> OTHER INFORMATION: Mut-N44

<400> SEQUENCE: 25

Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
                20                  25                  30

Tyr Thr Pro Ile Asp Ile Ser Leu Ser Leu Thr Gln Phe Leu Leu Ser
            35                  40                  45

Glu Phe Val Pro Gly Ala Gly Phe Val Leu Gly Leu Val Asp Ile Ile
        50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
            100                 105                 110

Ser Phe Arg Ala Trp Glu Ala Asp Pro Thr Asn Pro Ala Leu Arg Glu
        115                 120                 125

Glu Met Arg Ile Gln Phe Asn Asp Met Asn Ser Ala Leu Thr Thr Ala
    130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
```

```
                    165                 170                 175
Val Phe Gly Gln Arg Trp Glu Phe Asp Ala Thr Thr Ile Asn Ser Arg
                180                 185                 190

Tyr Asn Asp Leu Thr Arg Leu Ile Gly Asn Tyr Thr Asp Tyr Ala Val
            195                 200                 205

Arg Trp Tyr Asn Thr Gly Leu Glu Arg Val Trp Gly Pro Asp Ser Arg
        210                 215                 220

Asp Trp Val Arg Tyr Asn Gln Phe Arg Arg Glu Leu Thr Leu Thr Val
225                 230                 235                 240

Leu Asp Ile Val Ser Leu Phe Ser Asn Tyr Asp Ser Arg Arg Tyr Pro
                245                 250                 255

Ile Arg Thr Val Ser Gln Leu Thr Arg Glu Ile Tyr Thr Asn Pro Val
                260                 265                 270

Leu Glu Asn Phe Asp Gly Ser Phe Arg Gly Met Ala Gln Arg Ile Glu
            275                 280                 285

Arg Ser Ile Arg Ser Pro His Leu Met Asp Ile Leu Asn Ser Ile Thr
        290                 295                 300

Ile Tyr Thr Asp Val His Arg Gly Tyr Tyr Trp Ser Gly His Gln
305                 310                 315                 320

Ile Thr Ala Ser Pro Val Gly Phe Ser Gly Pro Glu Phe Ala Phe Pro
                325                 330                 335

Leu Tyr Gly Thr Met Gly Asn Ala Ala Pro Gln Gln Arg Ile Val Ala
            340                 345                 350

Gln Leu Gly Gln Gly Val Tyr Arg Thr Leu Ser Ser Thr Leu Tyr Arg
        355                 360                 365

Arg Pro Phe Asn Ile Gly Pro Asn Asn Gln Gln Leu Ser Val Leu Asp
        370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Val Ile Pro Pro Gln
                405                 410                 415

Asp Asn Ser Val Pro Pro Arg Ala Gly Phe Ser His Arg Leu Ser His
            420                 425                 430

Val Ser Met Phe Arg Ser Gly Phe Ser Asn Ser Ser Val Ser Ile Ile
        435                 440                 445

Arg Ala Pro Met Phe Ser Trp Ile His Arg Ser Ala Glu Phe Asn Asn
        450                 455                 460

Ile Ile Ala Ser Asp Ser Ile Thr Gln Ile Pro Ala Val Lys Gly Asn
465                 470                 475                 480

Phe Leu Phe Asn Gly Ser Val Ile Ser Gly Pro Gly Phe Thr Gly Gly
                485                 490                 495

Asp Leu Val Arg Leu Asn Ser Ser Gly Asn Asn Ile Gln Asn Arg Gly
            500                 505                 510

Tyr Ile Glu Val Pro Ile His Phe Pro Ser Thr Ser Thr Arg Tyr Arg
        515                 520                 525

Val Arg Val Arg Tyr Ala Ser Val Thr Pro Ile His Leu Asn Val Asn
        530                 535                 540

Trp Gly Asn Ser Ser Ile Phe Ser Asn Thr Val Pro Ala Thr Ala Thr
545                 550                 555                 560

Ser Leu Asp Asn Leu Gln Ser Ser Asp Phe Gly Tyr Phe Glu Ser Ala
                565                 570                 575

Asn Ala Phe Thr Ser Ser Leu Gly Asn Ile Val Gly Val Arg Asn Phe
            580                 585                 590
```

Ser Gly Thr Ala Gly Val Ile Ile Asp Arg Phe Glu Phe Ile Pro Val
            595                 600                 605

Thr Ala Thr Leu Glu Ala Glu Tyr Asn Leu
            610                 615

<210> SEQ ID NO 26
<211> LENGTH: 618
<212> TYPE: PRT
<213> ORGANISM: Artificial Sequence
<220> FEATURE:
<223> OTHER INFORMATION: Mut-N51

<400> SEQUENCE: 26

Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
            20                  25                  30

Tyr Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Val Asp Ile Ile
    50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
            100                 105                 110

Ser Phe Arg Ala Trp Glu Ala Asp Pro Thr Asn Pro Ala Leu Arg Val
        115                 120                 125

Glu Met Arg Ile Gln Phe Asn Asp Met Asn Ser Ala Leu Thr Thr Ala
    130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Thr Thr Ile Asn Ser Arg
            180                 185                 190

Tyr Asn Asp Leu Thr Arg Leu Ile Gly Asn Tyr Thr Asp Tyr Ala Val
        195                 200                 205

Arg Trp Tyr Asn Thr Gly Leu Glu Arg Val Trp Gly Pro Asp Ser Arg
    210                 215                 220

Asp Trp Ile Arg Tyr Asn Gln Phe Arg Arg Glu Leu Thr Leu Thr Val
225                 230                 235                 240

Leu Asp Ile Val Ser Leu Phe Pro Asn Tyr Asp Ser Arg Thr Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Ser Ala Gln Gly Ile Glu
        275                 280                 285

Arg Ser Ile Arg Ser Pro His Leu Met Asp Ile Leu Asn Ser Ile Thr
    290                 295                 300

Ile Tyr Thr Asp Val His Arg Gly Tyr Tyr Tyr Trp Ser Gly His Gln
305                 310                 315                 320

Ile Thr Ala Ser Pro Val Gly Phe Ser Gly Pro Glu Phe Thr Phe Pro
                325                 330                 335

Leu Tyr Gly Thr Met Gly Asn Ala Ala Pro Gln Gln Arg Ile Val Ala
            340                 345                 350

Gln Leu Gly Gln Gly Val Tyr Arg Thr Leu Ser Ser Thr Leu Tyr Arg
        355                 360                 365

Arg Pro Phe Asn Ile Gly Ile Asn Asn Gln Gln Leu Ser Val Leu Asp
    370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Val Ile Pro Pro Gln
                405                 410                 415

Asn Asn Asn Val Pro Pro Arg Ala Gly Phe Ser His Arg Leu Ser His
            420                 425                 430

Val Ser Met Phe Arg Ser Gly Phe Ser Asn Ser Val Ser Ile Ile
        435                 440                 445

Arg Ala Pro Met Phe Ser Trp Ile His Arg Ser Ala Glu Phe Asn Asn
    450                 455                 460

Ile Ile Ala Ser Asp Ser Ile Thr Gln Ile Pro Ala Val Lys Gly Asn
465                 470                 475                 480

Phe Leu Phe Asn Gly Ser Val Ile Ser Gly Pro Gly Phe Thr Gly Gly
                485                 490                 495

Asp Leu Val Arg Leu Asn Ser Ser Gly Asn Asn Ile Gln Asn Arg Gly
            500                 505                 510

Tyr Ile Glu Val Pro Ile His Phe Pro Ser Thr Ser Thr Arg Tyr Arg
        515                 520                 525

Val Arg Val Arg Tyr Ala Ser Val Thr Pro Ile His Leu Asn Val Asn
    530                 535                 540

Trp Gly Asn Ser Ser Ile Phe Ser Asn Thr Val Pro Ala Thr Ala Thr
545                 550                 555                 560

Ser Leu Asp Asn Leu Gln Ser Ser Asp Phe Gly Tyr Phe Glu Ser Ala
                565                 570                 575

Asn Ala Phe Thr Ser Ser Leu Gly Asn Ile Val Gly Val Arg Asn Phe
            580                 585                 590

Ser Gly Thr Ala Gly Val Ile Ile Asp Arg Phe Glu Phe Ile Pro Val
        595                 600                 605

Thr Ala Thr Leu Glu Ala Glu Tyr Asn Leu
    610                 615

<210> SEQ ID NO 27
<211> LENGTH: 618
<212> TYPE: PRT
<213> ORGANISM: Artificial Sequence
<220> FEATURE:
<223> OTHER INFORMATION: Mut-N52

<400> SEQUENCE: 27

Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
            20                  25                  30

Tyr Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Val Asp Ile Ile
    50                  55                  60

Trp Gly Ile Phe Gly Pro Ser Gln Trp Asp Ala Phe Leu Val Gln Ile
65                  70                  75                  80

```
Glu Gln Leu Ile Asn Gln Arg Ile Glu Glu Phe Ala Arg Asn Gln Ala
             85                  90                  95

Ile Ser Arg Leu Glu Gly Leu Ser Asn Leu Tyr Gln Ile Tyr Ala Glu
            100                 105                 110

Ser Phe Arg Ala Trp Glu Ala Asp Pro Thr Asn Pro Ala Leu Arg Val
            115                 120                 125

Glu Met Arg Ile Gln Phe Asn Asp Met Asn Ser Ala Leu Thr Thr Ala
            130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
            165                 170                 175

Val Phe Gly Gln Arg Trp Gly Phe Asp Ala Thr Thr Ile Asn Ser Arg
            180                 185                 190

Tyr Asn Asp Leu Thr Arg Leu Ile Gly Asn Tyr Thr Asp Tyr Ala Val
            195                 200                 205

Arg Trp Tyr Asn Thr Gly Leu Glu Arg Val Trp Gly Pro Asp Ser Arg
            210                 215                 220

Asp Trp Ile Arg Tyr Asn Gln Phe Arg Arg Glu Leu Thr Leu Thr Val
225                 230                 235                 240

Leu Asp Ile Val Ser Leu Phe Pro Asn Tyr Asp Ser Arg Thr Tyr Pro
            245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Met Ala Gln Gly Ile Glu
            275                 280                 285

Arg Ser Ile Arg Ser Pro His Leu Met Asp Ile Leu Asn Ser Ile Thr
            290                 295                 300

Ile Tyr Thr Asp Val His Arg Gly Tyr Tyr Tyr Trp Ser Gly His Gln
305                 310                 315                 320

Ile Thr Ala Ser Pro Val Gly Phe Ser Gly Pro Glu Phe Thr Phe Pro
            325                 330                 335

Leu Tyr Gly Thr Met Gly Asn Ala Ala Pro Gln Gln Arg Ile Val Ala
            340                 345                 350

Gln Leu Gly Gln Gly Val Tyr Arg Thr Leu Ser Ser Thr Leu Tyr Arg
            355                 360                 365

Arg Pro Phe Asn Ile Gly Ile Asn Asn Gln Gln Leu Ser Val Leu Asp
            370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Val Ile Pro Pro Gln
            405                 410                 415

Asn Asn Asn Val Pro Pro Arg Ala Gly Phe Ser His Arg Leu Ser His
            420                 425                 430

Val Ser Met Phe Arg Ser Gly Phe Ser Asn Ser Ser Val Ser Ile Ile
            435                 440                 445

Arg Ala Pro Met Phe Ser Trp Ile His Arg Ser Ala Glu Phe Asn Asn
450                 455                 460

Ile Ile Ala Ser Asp Ser Ile Thr Gln Ile Pro Ala Val Lys Gly Asn
465                 470                 475                 480

Phe Leu Phe Asn Gly Ser Val Ile Ser Gly Pro Gly Phe Thr Gly Gly
            485                 490                 495
```

```
Asp Leu Val Arg Leu Asn Ser Ser Gly Asn Asn Ile Gln Asn Arg Gly
                500                 505                 510

Tyr Ile Glu Val Pro Ile His Phe Pro Ser Thr Ser Thr Arg Tyr Arg
            515                 520                 525

Val Arg Val Arg Tyr Ala Ser Val Thr Pro Ile His Leu Asn Val Asn
        530                 535                 540

Trp Gly Asn Ser Ser Ile Phe Ser Asn Thr Val Pro Ala Thr Ala Thr
545                 550                 555                 560

Ser Leu Asp Asn Leu Gln Ser Ser Asp Phe Gly Tyr Phe Glu Ser Ala
                565                 570                 575

Asn Ala Phe Thr Ser Ser Leu Gly Asn Ile Val Gly Val Arg Asn Phe
            580                 585                 590

Ser Gly Thr Ala Gly Val Ile Ile Asp Arg Phe Glu Phe Ile Pro Val
        595                 600                 605

Thr Ala Thr Leu Glu Ala Glu Tyr Asn Leu
            610                 615

<210> SEQ ID NO 28
<211> LENGTH: 618
<212> TYPE: PRT
<213> ORGANISM: Artificial Sequence
<220> FEATURE:
<223> OTHER INFORMATION: Mut-N54

<400> SEQUENCE: 28

Met Asp Asn Asn Pro Asn Ile Asn Glu Cys Ile Pro Tyr Asn Cys Leu
1               5                   10                  15

Ser Asn Pro Glu Val Glu Val Leu Gly Gly Arg Ile Glu Thr Gly
            20                  25                  30

Tyr Thr Pro Ile Asp Ile Ser Leu Ser Leu Thr Gln Phe Leu Leu Ser
            35                  40                  45

Glu Phe Val Pro Gly Ala Gly Phe Val Leu Gly Leu Val Asp Ile Ile
        50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
            100                 105                 110

Ser Phe Arg Ala Trp Glu Ala Asp Pro Thr Asn Pro Ala Leu Arg Val
        115                 120                 125

Glu Met Arg Ile Gln Phe Asn Asp Met Asn Ser Ala Leu Thr Thr Ala
130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Thr Thr Ile Asn Ser Arg
            180                 185                 190

Tyr Asn Asp Leu Thr Arg Leu Ile Gly Asn Tyr Thr Asp Tyr Ala Val
        195                 200                 205

Arg Trp Tyr Asn Thr Gly Leu Glu Arg Val Trp Gly Pro Asp Ser Arg
210                 215                 220

Asp Trp Ile Arg Tyr Asn Gln Phe Arg Arg Glu Leu Thr Leu Thr Val
225                 230                 235                 240
```

Leu Asp Ile Val Ser Leu Phe Pro Asn Tyr Asp Ser Arg Thr Tyr Pro
          245                 250                 255

Ile Arg Thr Val Ser Gln Leu Thr Arg Glu Ile Tyr Thr Asn Pro Val
        260                 265                 270

Leu Glu Asn Phe Asp Gly Ser Phe Arg Gly Ser Ala Gln Gly Ile Glu
        275                 280                 285

Arg Ser Ile Arg Ser Pro His Leu Met Asp Ile Leu Asn Ser Ile Thr
        290                 295                 300

Ile Tyr Thr Asp Val His Arg Gly Tyr Tyr Trp Ser Gly His Gln
305                 310                 315                 320

Ile Thr Ala Ser Pro Val Gly Phe Ser Gly Pro Glu Phe Ala Phe Pro
                325                 330                 335

Leu Tyr Gly Thr Met Gly Asn Ala Ala Pro Gln Gln Arg Ile Val Ala
            340                 345                 350

Gln Leu Gly Gln Gly Val Tyr Arg Thr Leu Ser Ser Thr Leu Tyr Arg
        355                 360                 365

Arg Pro Phe Asn Ile Gly Ile Asn Asn Gln Gln Leu Ser Val Leu Asp
    370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Val Ile Pro Pro Gln
            405                 410                 415

Asn Asn Asn Val Pro Pro Arg Ala Gly Phe Ser His Arg Leu Ser His
            420                 425                 430

Val Ser Met Phe Arg Ser Gly Phe Ser Asn Ser Ser Val Ser Ile Ile
        435                 440                 445

Arg Ala Pro Met Phe Ser Trp Ile His Arg Ser Ala Glu Phe Asn Asn
    450                 455                 460

Ile Ile Ala Ser Asp Ser Ile Thr Gln Ile Pro Ala Val Lys Gly Asn
465                 470                 475                 480

Phe Leu Phe Asn Gly Ser Val Ile Ser Gly Pro Gly Phe Thr Gly Gly
                485                 490                 495

Asp Leu Val Arg Leu Asn Ser Ser Gly Asn Asn Ile Gln Asn Arg Gly
            500                 505                 510

Tyr Ile Glu Val Pro Ile His Phe Pro Ser Thr Ser Thr Arg Tyr Arg
        515                 520                 525

Val Arg Val Arg Tyr Ala Ser Val Thr Pro Ile His Leu Asn Val Asn
    530                 535                 540

Trp Gly Asn Ser Ser Ile Phe Ser Asn Thr Val Pro Ala Thr Ala Thr
545                 550                 555                 560

Ser Leu Asp Asn Leu Gln Ser Ser Asp Phe Gly Tyr Phe Glu Ser Ala
            565                 570                 575

Asn Ala Phe Thr Ser Ser Leu Gly Asn Ile Val Gly Val Arg Asn Phe
        580                 585                 590

Ser Gly Thr Ala Gly Val Ile Ile Asp Arg Phe Glu Phe Ile Pro Val
    595                 600                 605

Thr Ala Thr Leu Glu Ala Glu Tyr Asn Leu
    610                 615

<210> SEQ ID NO 29
<211> LENGTH: 618
<212> TYPE: PRT
<213> ORGANISM: Artificial Sequence
<220> FEATURE:
<223> OTHER INFORMATION: Mut-N55

<400> SEQUENCE: 29

```
Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
            20                  25                  30

Tyr Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Val Asp Ile Ile
    50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
            100                 105                 110

Ser Phe Arg Ala Trp Glu Ala Asp Pro Thr Asn Pro Ala Leu Arg Val
        115                 120                 125

Glu Met Arg Ile Gln Phe Asn Asp Met Asn Ser Ala Leu Thr Thr Ala
    130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Thr Thr Ile Asn Ser Arg
            180                 185                 190

Tyr Asn Asp Leu Thr Arg Leu Ile Gly Asn Tyr Thr Asp Tyr Ala Val
        195                 200                 205

Arg Trp Tyr Asn Thr Gly Leu Glu Arg Val Trp Gly Pro Asp Ser Arg
    210                 215                 220

Asp Trp Ile Arg Tyr Asn Gln Phe Arg Arg Glu Leu Thr Leu Thr Val
225                 230                 235                 240

Leu Asp Ile Val Ser Leu Phe Pro Asn Tyr Asp Ser Arg Thr Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Ser Ala Gln Gly Ile Glu
        275                 280                 285

Arg Ser Ile Arg Ser Pro His Leu Met Asp Ile Leu Asn Ser Ile Thr
    290                 295                 300

Ile Tyr Thr Asp Val His Arg Gly Tyr Tyr Tyr Trp Ser Gly His Gln
305                 310                 315                 320

Ile Thr Ala Ser Pro Val Gly Phe Ser Gly Pro Glu Phe Thr Phe Pro
                325                 330                 335

Leu Tyr Gly Thr Met Gly Asn Ala Ala Pro Gln Gln Arg Ile Val Ala
            340                 345                 350

Gln Leu Gly Gln Gly Val Tyr Arg Thr Leu Ser Ser Thr Leu Tyr Arg
        355                 360                 365

Arg Pro Phe Asn Ile Gly Pro Asn Asn Gln Gln Leu Ser Val Leu Asp
    370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Val Ile Pro Pro Gln
```

```
                    405                 410                 415
Asn Asn Asn Val Pro Pro Arg Ala Gly Phe Ser His Arg Leu Ser His
                420                 425                 430

Val Ser Met Phe Arg Ser Gly Phe Ser Asn Ser Ser Val Ser Ile Ile
                435                 440                 445

Arg Ala Pro Met Phe Ser Trp Ile His Arg Ser Ala Glu Phe Asn Asn
450                 455                 460

Ile Ile Ala Ser Asp Ser Ile Thr Gln Ile Pro Ala Val Lys Gly Asn
465                 470                 475                 480

Phe Leu Phe Asn Gly Ser Val Ile Ser Gly Pro Gly Phe Thr Gly Gly
                485                 490                 495

Asp Leu Val Arg Leu Asn Ser Ser Gly Asn Asn Ile Gln Asn Arg Gly
                500                 505                 510

Tyr Ile Glu Val Pro Ile His Phe Pro Ser Thr Ser Thr Arg Tyr Arg
                515                 520                 525

Val Arg Val Arg Tyr Ala Ser Val Thr Pro Ile His Leu Asn Val Asn
                530                 535                 540

Trp Gly Asn Ser Ser Ile Phe Ser Asn Thr Val Pro Ala Thr Ala Thr
545                 550                 555                 560

Ser Leu Asp Asn Leu Gln Ser Ser Asp Phe Gly Tyr Phe Glu Ser Ala
                565                 570                 575

Asn Ala Phe Thr Ser Ser Leu Gly Asn Ile Val Gly Val Arg Asn Phe
                580                 585                 590

Ser Gly Thr Ala Gly Val Ile Ile Asp Arg Phe Glu Phe Ile Pro Val
                595                 600                 605

Thr Ala Thr Leu Glu Ala Glu Tyr Asn Leu
                610                 615

<210> SEQ ID NO 30
<211> LENGTH: 618
<212> TYPE: PRT
<213> ORGANISM: Artificial Sequence
<220> FEATURE:
<223> OTHER INFORMATION: Mut-N57

<400> SEQUENCE: 30

Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
                20                  25                  30

Tyr Thr Pro Ile Asp Ile Ser Leu Ser Leu Thr Gln Phe Leu Leu Ser
            35                  40                  45

Glu Phe Val Pro Gly Ala Gly Phe Val Leu Gly Leu Val Asp Ile Ile
        50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
            100                 105                 110

Ser Phe Arg Ala Trp Glu Ala Asp Pro Thr Asn Pro Ala Leu Arg Val
        115                 120                 125

Glu Met Arg Ile Gln Phe Asn Asp Met Asn Ser Ala Leu Thr Thr Ala
    130                 135                 140

Ile Pro Leu Phe Ala Val Gln Asn Tyr Gln Val Pro Leu Leu Ser Val
```

-continued

```
145                 150                 155                 160
Tyr Val Gln Ala Ala Asn Leu His Leu Ser Val Leu Arg Asp Val Ser
                165                 170                 175
Val Phe Gly Gln Arg Trp Gly Phe Asp Ala Thr Thr Ile Asn Ser Arg
                180                 185                 190
Tyr Asn Asp Leu Thr Arg Leu Ile Gly Asn Tyr Thr Asp Tyr Ala Val
                195                 200                 205
Arg Trp Tyr Asn Thr Gly Leu Glu Arg Val Trp Gly Pro Asp Ser Arg
210                 215                 220
Asp Trp Ile Arg Tyr Asn Gln Phe Arg Glu Leu Thr Leu Thr Val
225                 230                 235                 240
Leu Asp Ile Val Ser Leu Phe Pro Asn Tyr Asp Ser Arg Thr Tyr Pro
                245                 250                 255
Ile Arg Thr Val Ser Gln Leu Thr Arg Glu Ile Tyr Thr Asn Pro Val
                260                 265                 270
Leu Glu Asn Phe Asp Gly Ser Phe Arg Gly Met Ala Gln Gly Ile Glu
                275                 280                 285
Arg Ser Ile Arg Ser Pro His Leu Met Asp Ile Leu Asn Ser Ile Thr
                290                 295                 300
Ile Tyr Thr Asp Val His Arg Gly Tyr Tyr Tyr Trp Ser Gly His Gln
305                 310                 315                 320
Ile Thr Ala Ser Pro Val Gly Phe Ser Gly Pro Glu Phe Ala Phe Pro
                325                 330                 335
Leu Tyr Gly Thr Met Gly Asn Ala Ala Pro Gln Gln Arg Ile Val Ala
                340                 345                 350
Gln Leu Gly Gln Gly Val Tyr Arg Thr Leu Ser Ser Thr Leu Tyr Arg
                355                 360                 365
Arg Pro Phe Asn Ile Gly Ile Asn Asn Gln Gln Leu Ser Val Leu Asp
                370                 375                 380
Gly Thr Glu Phe Ala Tyr Gly Thr Ser Ser Asn Leu Pro Ser Ala Val
385                 390                 395                 400
Tyr Arg Lys Ser Gly Thr Val Asp Ser Leu Asp Val Ile Pro Pro Gln
                405                 410                 415
Asn Asn Asn Val Pro Pro Arg Ala Gly Phe Ser His Arg Leu Ser His
                420                 425                 430
Val Ser Met Phe Arg Ser Gly Phe Ser Asn Ser Ser Val Ser Ile Ile
                435                 440                 445
Arg Ala Pro Met Phe Ser Trp Ile His Arg Ser Ala Glu Phe Asn Asn
450                 455                 460
Ile Ile Ala Ser Asp Ser Ile Thr Gln Ile Pro Ala Val Lys Gly Asn
465                 470                 475                 480
Phe Leu Phe Asn Gly Ser Val Ile Ser Gly Pro Gly Phe Thr Gly Gly
                485                 490                 495
Asp Leu Val Arg Leu Asn Ser Ser Gly Asn Asn Ile Gln Asn Arg Gly
                500                 505                 510
Tyr Ile Glu Val Pro Ile His Phe Pro Ser Thr Ser Thr Arg Tyr Arg
                515                 520                 525
Val Arg Val Arg Tyr Ala Ser Val Thr Pro Ile His Leu Asn Val Asn
                530                 535                 540
Trp Gly Asn Ser Ser Ile Phe Ser Asn Thr Val Pro Ala Thr Ala Thr
545                 550                 555                 560
Ser Leu Asp Asn Leu Gln Ser Ser Asp Phe Gly Tyr Phe Glu Ser Ala
                565                 570                 575
```

Asn Ala Phe Thr Ser Ser Leu Gly Asn Ile Val Gly Val Arg Asn Phe
            580                 585                 590

Ser Gly Thr Ala Gly Val Ile Ile Asp Arg Phe Glu Phe Ile Pro Val
        595                 600                 605

Thr Ala Thr Leu Glu Ala Glu Tyr Asn Leu
        610                 615

<210> SEQ ID NO 31
<211> LENGTH: 618
<212> TYPE: PRT
<213> ORGANISM: Artificial Sequence
<220> FEATURE:
<223> OTHER INFORMATION: Mut-N58

<400> SEQUENCE: 31

Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
            20                  25                  30

Tyr Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Val Asp Ile Ile
    50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
            100                 105                 110

Ser Phe Arg Ala Trp Glu Ala Asp Pro Thr Asn Pro Ala Leu Arg Val
        115                 120                 125

Glu Met Arg Ile Gln Phe Asn Asp Met Asn Ser Ala Leu Thr Thr Ala
    130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Thr Thr Ile Asn Ser Arg
            180                 185                 190

Tyr Asn Asp Leu Thr Arg Leu Ile Gly Asn Tyr Thr Asp Tyr Ala Val
        195                 200                 205

Arg Trp Tyr Asn Thr Gly Leu Glu Arg Val Trp Gly Pro Asp Ser Arg
    210                 215                 220

Asp Trp Ile Arg Tyr Asn Gln Phe Arg Arg Glu Leu Thr Leu Thr Val
225                 230                 235                 240

Leu Asp Ile Val Ser Leu Phe Pro Asn Tyr Asp Ser Arg Thr Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Met Ala Gln Gly Ile Glu
        275                 280                 285

Arg Ser Ile Arg Ser Pro His Leu Met Asp Ile Leu Asn Ser Ile Thr
    290                 295                 300

Ile Tyr Thr Asp Val His Arg Gly Tyr Tyr Tyr Trp Ser Gly His Gln
305                 310                 315                 320

```
Ile Thr Ala Ser Pro Val Gly Phe Ser Gly Pro Glu Phe Thr Phe Pro
            325                 330                 335

Leu Tyr Gly Thr Met Gly Asn Ala Ala Pro Gln Gln Arg Ile Val Ala
            340                 345                 350

Gln Leu Gly Gln Gly Val Tyr Arg Thr Leu Ser Ser Thr Leu Tyr Arg
            355                 360                 365

Arg Pro Phe Asn Ile Gly Pro Asn Asn Gln Gln Leu Ser Val Leu Asp
370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Val Ile Pro Pro Gln
            405                 410                 415

Asn Asn Asn Val Pro Pro Arg Ala Gly Phe Ser His Arg Leu Ser His
            420                 425                 430

Val Ser Met Phe Arg Ser Gly Phe Ser Asn Ser Ser Val Ser Ile Ile
            435                 440                 445

Arg Ala Pro Met Phe Ser Trp Ile His Arg Ser Ala Glu Phe Asn Asn
            450                 455                 460

Ile Ile Ala Ser Asp Ser Ile Thr Gln Ile Pro Ala Val Lys Gly Asn
465                 470                 475                 480

Phe Leu Phe Asn Gly Ser Val Ile Ser Gly Pro Gly Phe Thr Gly Gly
            485                 490                 495

Asp Leu Val Arg Leu Asn Ser Ser Gly Asn Asn Ile Gln Asn Arg Gly
            500                 505                 510

Tyr Ile Glu Val Pro Ile His Phe Pro Ser Thr Ser Thr Arg Tyr Arg
            515                 520                 525

Val Arg Val Arg Tyr Ala Ser Val Thr Pro Ile His Leu Asn Val Asn
            530                 535                 540

Trp Gly Asn Ser Ser Ile Phe Ser Asn Thr Val Pro Ala Thr Ala Thr
545                 550                 555                 560

Ser Leu Asp Asn Leu Gln Ser Ser Asp Phe Gly Tyr Phe Glu Ser Ala
            565                 570                 575

Asn Ala Phe Thr Ser Ser Leu Gly Asn Ile Val Gly Val Arg Asn Phe
            580                 585                 590

Ser Gly Thr Ala Gly Val Ile Ile Asp Arg Phe Glu Phe Ile Pro Val
            595                 600                 605

Thr Ala Thr Leu Glu Ala Glu Tyr Asn Leu
            610                 615

<210> SEQ ID NO 32
<211> LENGTH: 618
<212> TYPE: PRT
<213> ORGANISM: Artificial Sequence
<220> FEATURE:
<223> OTHER INFORMATION: Mut-N61

<400> SEQUENCE: 32

Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
            20                  25                  30

Tyr Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Val Asp Ile Ile
    50                  55                  60
```

-continued

```
Trp Gly Ile Phe Gly Pro Ser Gln Trp Asp Ala Phe Leu Val Gln Ile
 65                  70                  75                  80

Glu Gln Leu Ile Asn Gln Arg Ile Glu Glu Phe Ala Arg Asn Gln Ala
                 85                  90                  95

Ile Ser Arg Leu Glu Gly Leu Ser Asn Leu Tyr Gln Ile Tyr Ala Glu
            100                 105                 110

Ser Phe Arg Ala Trp Glu Ala Asp Pro Thr Asn Pro Ala Leu Arg Val
        115                 120                 125

Glu Met Arg Ile Gln Phe Asn Asp Met Asn Ser Ala Leu Thr Thr Ala
    130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Thr Thr Ile Asn Ser Arg
            180                 185                 190

Tyr Asn Asp Leu Thr Arg Leu Ile Gly Asn Tyr Thr Asp Tyr Ala Val
        195                 200                 205

Arg Trp Tyr Asn Thr Gly Leu Glu Arg Val Trp Gly Pro Asp Ser Arg
    210                 215                 220

Asp Trp Ile Arg Tyr Asn Gln Phe Arg Arg Glu Leu Thr Leu Thr Val
225                 230                 235                 240

Leu Asp Ile Val Ser Leu Phe Pro Asn Tyr Asp Ser Arg Thr Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Ser Ala Gln Arg Ile Glu
        275                 280                 285

Arg Ser Ile Arg Ser Pro His Leu Met Asp Ile Leu Asn Ser Ile Thr
    290                 295                 300

Ile Tyr Thr Asp Val His Arg Gly Tyr Tyr Tyr Trp Ser Gly His Gln
305                 310                 315                 320

Ile Thr Ala Ser Pro Val Gly Phe Ser Gly Pro Glu Phe Thr Phe Pro
                325                 330                 335

Leu Tyr Gly Thr Met Gly Asn Ala Ala Pro Gln Gln Arg Ile Val Ala
            340                 345                 350

Gln Leu Gly Gln Gly Val Tyr Arg Thr Leu Ser Ser Thr Leu Tyr Arg
        355                 360                 365

Arg Pro Phe Asn Ile Gly Pro Asn Asn Gln Gln Leu Ser Val Leu Asp
    370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Val Ile Pro Pro Gln
                405                 410                 415

Asn Asn Asn Val Pro Pro Arg Ala Gly Phe Ser His Arg Leu Ser His
            420                 425                 430

Val Ser Met Phe Arg Ser Gly Phe Ser Asn Ser Ser Val Ser Ile Ile
        435                 440                 445

Arg Ala Pro Met Phe Ser Trp Ile His Arg Ser Ala Glu Phe Asn Asn
    450                 455                 460

Ile Ile Ala Ser Asp Ser Ile Thr Gln Ile Pro Ala Val Lys Gly Asn
465                 470                 475                 480
```

```
Phe Leu Phe Asn Gly Ser Val Ile Ser Gly Pro Gly Phe Thr Gly Gly
                485                 490                 495

Asp Leu Val Arg Leu Asn Ser Ser Gly Asn Asn Ile Gln Asn Arg Gly
            500                 505                 510

Tyr Ile Glu Val Pro Ile His Phe Pro Ser Thr Ser Thr Arg Tyr Arg
        515                 520                 525

Val Arg Val Arg Tyr Ala Ser Val Thr Pro Ile His Leu Asn Val Asn
    530                 535                 540

Trp Gly Asn Ser Ser Ile Phe Ser Asn Thr Val Pro Ala Thr Ala Thr
545                 550                 555                 560

Ser Leu Asp Asn Leu Gln Ser Ser Asp Phe Gly Tyr Phe Glu Ser Ala
                565                 570                 575

Asn Ala Phe Thr Ser Ser Leu Gly Asn Ile Val Gly Val Arg Asn Phe
            580                 585                 590

Ser Gly Thr Ala Gly Val Ile Ile Asp Arg Phe Glu Phe Ile Pro Val
        595                 600                 605

Thr Ala Thr Leu Glu Ala Glu Tyr Asn Leu
    610                 615

<210> SEQ ID NO 33
<211> LENGTH: 618
<212> TYPE: PRT
<213> ORGANISM: Artificial Sequence
<220> FEATURE:
<223> OTHER INFORMATION: Mut-N64

<400> SEQUENCE: 33

Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
            20                  25                  30

Tyr Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Val Asp Ile Ile
    50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
            100                 105                 110

Ser Phe Arg Ala Trp Glu Ala Asp Pro Thr Asn Pro Ala Leu Arg Val
        115                 120                 125

Glu Met Arg Ile Gln Phe Asn Asp Met Asn Ser Ala Leu Thr Thr Ala
    130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Thr Thr Ile Asn Ser Arg
            180                 185                 190

Tyr Asn Asp Leu Thr Arg Leu Ile Gly Asn Tyr Thr Asp Tyr Ala Val
        195                 200                 205

Arg Trp Tyr Asn Thr Gly Leu Glu Arg Val Trp Gly Pro Asp Ser Arg
    210                 215                 220
```

```
Asp Trp Ile Arg Tyr Asn Gln Phe Arg Arg Glu Leu Thr Leu Thr Val
225                 230                 235                 240

Leu Asp Ile Val Ser Leu Phe Pro Asn Tyr Asp Ser Arg Thr Tyr Pro
            245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Ser Ala Gln Gly Ile Glu
            275                 280                 285

Arg Ser Ile Arg Ser Pro His Leu Met Asp Ile Leu Asn Ser Ile Thr
290                 295                 300

Ile Tyr Thr Asp Val His Arg Gly Tyr Tyr Trp Ser Gly His Gln
305                 310                 315                 320

Ile Thr Ala Ser Pro Val Gly Phe Ser Gly Pro Glu Phe Ala Phe Pro
            325                 330                 335

Leu Tyr Gly Thr Met Gly Asn Ala Ala Pro Gln Gln Arg Ile Val Ala
            340                 345                 350

Gln Leu Gly Gln Gly Val Tyr Arg Thr Leu Ser Ser Thr Leu Tyr Arg
            355                 360                 365

Arg Pro Phe Asn Ile Gly Pro Asn Asn Gln Gln Leu Ser Val Leu Asp
370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Val Ile Pro Pro Gln
            405                 410                 415

Asn Asn Asn Val Pro Pro Arg Ala Gly Phe Ser His Arg Leu Ser His
            420                 425                 430

Val Ser Met Phe Arg Ser Gly Phe Ser Asn Ser Ser Val Ser Ile Ile
            435                 440                 445

Arg Ala Pro Met Phe Ser Trp Ile His Arg Ser Ala Glu Phe Asn Asn
450                 455                 460

Ile Ile Ala Ser Asp Ser Ile Thr Gln Ile Pro Ala Val Lys Gly Asn
465                 470                 475                 480

Phe Leu Phe Asn Gly Ser Val Ile Ser Gly Pro Gly Phe Thr Gly Gly
            485                 490                 495

Asp Leu Val Arg Leu Asn Ser Ser Gly Asn Asn Ile Gln Asn Arg Gly
            500                 505                 510

Tyr Ile Glu Val Pro Ile His Phe Pro Ser Thr Ser Thr Arg Tyr Arg
            515                 520                 525

Val Arg Val Arg Tyr Ala Ser Val Thr Pro Ile His Leu Asn Val Asn
530                 535                 540

Trp Gly Asn Ser Ser Ile Phe Ser Asn Thr Val Pro Ala Thr Ala Thr
545                 550                 555                 560

Ser Leu Asp Asn Leu Gln Ser Ser Asp Phe Gly Tyr Phe Glu Ser Ala
            565                 570                 575

Asn Ala Phe Thr Ser Ser Leu Gly Asn Ile Val Gly Val Arg Asn Phe
            580                 585                 590

Ser Gly Thr Ala Gly Val Ile Ile Asp Arg Phe Glu Phe Ile Pro Val
            595                 600                 605

Thr Ala Thr Leu Glu Ala Glu Tyr Asn Leu
            610                 615

<210> SEQ ID NO 34
<211> LENGTH: 618
<212> TYPE: PRT
```

<213> ORGANISM: Artificial Sequence
<220> FEATURE:
<223> OTHER INFORMATION: Mut-N68

<400> SEQUENCE: 34

```
Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
            20                  25                  30

Tyr Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Val Asp Ile Ile
    50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
            100                 105                 110

Ser Phe Arg Ala Trp Glu Ala Asp Pro Thr Asn Pro Ala Leu Arg Val
        115                 120                 125

Glu Met Arg Ile Gln Phe Asn Asp Met Asn Ser Ala Leu Thr Thr Ala
    130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Thr Thr Ile Asn Ser Arg
            180                 185                 190

Tyr Asn Asp Leu Thr Arg Leu Ile Gly Asn Tyr Thr Asp Tyr Ala Val
        195                 200                 205

Arg Trp Tyr Asn Thr Gly Leu Glu Arg Val Trp Gly Pro Asp Ser Arg
    210                 215                 220

Asp Trp Ile Arg Tyr Asn Gln Phe Arg Arg Glu Leu Thr Leu Thr Val
225                 230                 235                 240

Leu Asp Ile Val Ser Leu Phe Pro Asn Tyr Asp Ser Arg Thr Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Met Ala Gln Arg Ile Glu
        275                 280                 285

Arg Ser Ile Arg Ser Pro His Leu Met Asp Ile Leu Asn Ser Ile Thr
    290                 295                 300

Ile Tyr Thr Asp Val His Arg Gly Tyr Tyr Tyr Trp Ser Gly His Gln
305                 310                 315                 320

Ile Thr Ala Ser Pro Val Gly Phe Ser Gly Pro Glu Phe Ala Phe Pro
                325                 330                 335

Leu Tyr Gly Thr Met Gly Asn Ala Ala Pro Gln Gln Arg Ile Val Ala
            340                 345                 350

Gln Leu Gly Gln Gly Val Tyr Arg Thr Leu Ser Ser Thr Leu Tyr Arg
        355                 360                 365

Arg Pro Phe Asn Ile Gly Pro Asn Asn Gln Gln Leu Ser Val Leu Asp
    370                 375                 380

Gly Thr Glu Phe Ala Tyr Gly Thr Ser Ser Asn Leu Pro Ser Ala Val
```

```
                385                 390                 395                 400
Tyr Arg Lys Ser Gly Thr Val Asp Ser Leu Asp Val Ile Pro Pro Gln
                    405                 410                 415

Asn Asn Asn Val Pro Pro Arg Ala Gly Phe Ser His Arg Leu Ser His
                420                 425                 430

Val Ser Met Phe Arg Ser Gly Phe Ser Asn Ser Ser Val Ser Ile Ile
                435                 440                 445

Arg Ala Pro Met Phe Ser Trp Ile His Arg Ser Ala Glu Phe Asn Asn
            450                 455                 460

Ile Ile Ala Ser Asp Ser Ile Thr Gln Ile Pro Ala Val Lys Gly Asn
465                 470                 475                 480

Phe Leu Phe Asn Gly Ser Val Ile Ser Gly Pro Gly Phe Thr Gly Gly
                485                 490                 495

Asp Leu Val Arg Leu Asn Ser Ser Gly Asn Asn Ile Gln Asn Arg Gly
                500                 505                 510

Tyr Ile Glu Val Pro Ile His Phe Pro Ser Thr Ser Thr Arg Tyr Arg
            515                 520                 525

Val Arg Val Arg Tyr Ala Ser Val Thr Pro Ile His Leu Asn Val Asn
            530                 535                 540

Trp Gly Asn Ser Ser Ile Phe Ser Asn Thr Val Pro Ala Thr Ala Thr
545                 550                 555                 560

Ser Leu Asp Asn Leu Gln Ser Ser Asp Phe Gly Tyr Phe Glu Ser Ala
                565                 570                 575

Asn Ala Phe Thr Ser Ser Leu Gly Asn Ile Val Gly Val Arg Asn Phe
                580                 585                 590

Ser Gly Thr Ala Gly Val Ile Ile Asp Arg Phe Glu Phe Ile Pro Val
            595                 600                 605

Thr Ala Thr Leu Glu Ala Glu Tyr Asn Leu
            610                 615

<210> SEQ ID NO 35
<211> LENGTH: 618
<212> TYPE: PRT
<213> ORGANISM: Artificial Sequence
<220> FEATURE:
<223> OTHER INFORMATION: Mut-N71

<400> SEQUENCE: 35

Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
            20                  25                  30

Tyr Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Val Asp Ile Ile
    50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
            100                 105                 110

Ser Phe Arg Ala Trp Glu Ala Asp Pro Thr Asn Pro Ala Leu Arg Val
        115                 120                 125

Glu Met Arg Ile Gln Phe Asn Asp Met Asn Ser Ala Leu Thr Thr Ala
```

```
              130                 135                 140
Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Thr Thr Ile Asn Ser Arg
                180                 185                 190

Tyr Asn Asp Leu Thr Arg Leu Ile Gly Asn Tyr Thr Asp Tyr Ala Val
                195                 200                 205

Arg Trp Tyr Asn Thr Gly Leu Glu Arg Val Trp Gly Pro Asp Ser Arg
            210                 215                 220

Asp Trp Ile Arg Tyr Asn Gln Phe Arg Arg Glu Leu Thr Leu Thr Val
225                 230                 235                 240

Leu Asp Ile Val Ser Leu Phe Pro Asn Tyr Asp Ser Arg Thr Tyr Pro
                245                 250                 255

Ile Arg Thr Val Ser Gln Leu Thr Arg Glu Ile Tyr Thr Asn Pro Val
                260                 265                 270

Leu Glu Asn Phe Asp Gly Ser Phe Arg Gly Met Ala Gln Gly Ile Glu
                275                 280                 285

Arg Ser Ile Arg Ser Pro His Leu Met Asp Ile Leu Asn Ser Ile Thr
            290                 295                 300

Ile Tyr Thr Asp Val His Arg Gly Tyr Tyr Trp Ser Gly His Gln
305                 310                 315                 320

Ile Thr Ala Ser Pro Val Gly Phe Ser Gly Pro Glu Phe Ala Phe Pro
                325                 330                 335

Leu Tyr Gly Thr Met Gly Asn Ala Ala Pro Gln Gln Arg Ile Val Ala
                340                 345                 350

Gln Leu Gly Gln Gly Val Tyr Arg Thr Leu Ser Ser Thr Leu Tyr Arg
            355                 360                 365

Arg Pro Phe Asn Ile Gly Pro Asn Asn Gln Gln Leu Ser Val Leu Asp
            370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Val Ile Pro Pro Gln
                405                 410                 415

Asn Asn Asn Val Pro Pro Arg Ala Gly Phe Ser His Arg Leu Ser His
                420                 425                 430

Val Ser Met Phe Arg Ser Gly Phe Ser Asn Ser Ser Val Ser Ile Ile
                435                 440                 445

Arg Ala Pro Met Phe Ser Trp Ile His Arg Ser Ala Glu Phe Asn Asn
450                 455                 460

Ile Ile Ala Ser Asp Ser Ile Thr Gln Ile Pro Ala Val Lys Gly Asn
465                 470                 475                 480

Phe Leu Phe Asn Gly Ser Val Ile Ser Gly Pro Gly Phe Thr Gly Gly
                485                 490                 495

Asp Leu Val Arg Leu Asn Ser Ser Gly Asn Asn Ile Gln Asn Arg Gly
                500                 505                 510

Tyr Ile Glu Val Pro Ile His Phe Pro Ser Thr Ser Thr Arg Tyr Arg
                515                 520                 525

Val Arg Val Arg Tyr Ala Ser Val Thr Pro Ile His Leu Asn Val Asn
            530                 535                 540

Trp Gly Asn Ser Ser Ile Phe Ser Asn Thr Val Pro Ala Thr Ala Thr
545                 550                 555                 560
```

```
Ser Leu Asp Asn Leu Gln Ser Ser Asp Phe Gly Tyr Phe Glu Ser Ala
            565                 570                 575

Asn Ala Phe Thr Ser Ser Leu Gly Asn Ile Val Gly Val Arg Asn Phe
        580                 585                 590

Ser Gly Thr Ala Gly Val Ile Ile Asp Arg Phe Glu Phe Ile Pro Val
    595                 600                 605

Thr Ala Thr Leu Glu Ala Glu Tyr Asn Leu
    610                 615

<210> SEQ ID NO 36
<211> LENGTH: 1857
<212> TYPE: DNA
<213> ORGANISM: Artificial Sequence
<220> FEATURE:
<223> OTHER INFORMATION: Mod-cry1Ac

<400> SEQUENCE: 36
atggacaaca acccaaacat caacgaatgc attccataca actgcttgag taacccagaa      60
gttgaagtac ttggtggaga acgcattgaa accggttaca ctcccatcga catctccttg     120
tccttgacac agtttctgct cagcgagttc gtgccaggag ctgggttcgt tctcggacta     180
gttgacatca tctggggtat ctttggtcca tctcaatggg atgcattcct ggtgcaaatt     240
gagcagttga tcaaccagag gatcgaagag ttcgccagga accaggccat ctctcgtttg     300
gaaggattga gcaatctcta ccaaatctat gcagagagct cagagagtgg gaagccgat      360
cctactaacc cagctctccg cgaggaaatg cgtattcaat tcaacgacat gaacagcgcc     420
ttgaccacag ctatcccatt gttcgcagtc cagaactacc aagttcctct cttgtccgtg     480
tacgttcaag cagctaatct tcacctcagc gtgcttcgag acgttagcgt gtttgggcaa     540
agatggggat tcgatgctgc aaccatcaat agccgttaca cgaccttac taggctgatt      600
ggaaactaca ccgactacgc tgttcgttgg tacaacactg gcttggagcg tgtctggggt     660
cctgattcta gagattgggt gagatacaac cagttcagga gagaattgac cctcacagtt     720
ttggacattg tggctctctt cccgaactat gactccagac gttaccctat ccgtacagtg     780
tcccaactta ccagagaaat ctacactaac ccagttcttg agaacttcga cggtagcttc     840
cgtggttctg cccagggtat cgaaagatcc atcaggagcc acacttgat ggacatcttg      900
aacagcataa ctatctacac cgatgctcac agaggatact attactggtc tggacaccag     960
atcatggcct ttcagttgg attctccgga cctgagttta cctttcctct ctatggaact     1020
atgggaaacg ccgctccaca acaacgtatc gttgctcaac taggacaggg tgtctacaga    1080
accttgtctt ccaccttgta cagaagaccc ttcaatatcg gtatcaacaa ccagcaactt    1140
tccgttcttg acggaacaga gttcgcctat ggaacctctt ctaacttgcc atccgctgtt    1200
tacagaaaga gcggaaccgt tgattccttg gacgaaatcc caccacagaa caacaatgtg    1260
ccacccaggc aaggattctc ccacaggctt agccacgtgt ccatgttccg ttccggattc    1320
agcaacagtt ccgtgagcat catcagagct cctatgttct cttggattca ccgttctgcc    1380
gagttcaaca acatcatcgc atctgatagt attactcaaa tccctgccgt gaagggaaac    1440
ttcctttca atggaagcgt tatcagcgga ccaggattca ctggcggaga tcttgtgaga    1500
cttaacagct ctggcaacaa cattcagaat agaggctaca tcgaagttcc tatccacttc    1560
ccatccacat ctactagata cagagttagg gttagatacg cctctgtgac cccaatccac    1620
cttaacgtga actggggcaa ttcatctatc ttctccaaca ccgttccagc tactgctacc    1680
```

| tcactcgata atcttcaatc cagcgatttt ggttacttcg aaagtgccaa cgcattcact | 1740 |
| tcttcattgg gcaacatcgt gggtgttagg aatttcagcg gtactgcagg agtgatcatt | 1800 |
| gacagattcg agttcattcc tgttactgcc actcttgagg ctgagtacaa tctttaa | 1857 |

<210> SEQ ID NO 37
<211> LENGTH: 1857
<212> TYPE: DNA
<213> ORGANISM: Artificial Sequence
<220> FEATURE:
<223> OTHER INFORMATION: Mut-N02

<400> SEQUENCE: 37

| atggacaaca acccaaacat caacgaatgc attccataca actgcttgag taacccagaa | 60 |
| gttgaagtac ttggtggaga acgcattgaa accggttaca ctcccatcga catctccttg | 120 |
| tccttgacac agtttctgct cagcgagttc gtgccaggag ctgggttcgt tctcggacta | 180 |
| gttgacatca tctggggtat ctttggtcca tctcaatggg atgcattcct ggtgcaaatt | 240 |
| gagcagttga tcaaccagag gatcgaagag ttcgccagga accaggccat ctctcgtttg | 300 |
| gaaggattga gcaatctcta ccaaatctat gcagagagct tcagagagtg gaagccgat | 360 |
| cctactaacc cagctctccg cgaggaaatg cgtattcaat tcaacgacat gaacagcgcc | 420 |
| ttgaccacag ctatcccatt gttcgcagtc cagaactacc aagttcctct cttgtccgtg | 480 |
| tacgttcaag cagctaatct tcacctcagc gtgcttcgag acgttagcgt gtttgggcaa | 540 |
| agatggggat tcgatgctac caccatcaat agccgttaca cgaccttac taggctgatt | 600 |
| ggaaactaca ccgactacgc tgttcgttgg tacaacactg gcttggagcg tgtctggggt | 660 |
| cctgattcta gagattgggt gagatacaac cagttcagga gagaattgac cctcacagtt | 720 |
| ttggacattg tgtctctctt cagcaactat gactccagac gttaccctat ccgtacagtg | 780 |
| tcccaactta ccagagaaat ctacactaac ccagttcttg agaacttcga cggtagcttc | 840 |
| cgtggtatgg cccagaggat cgaaagatcc atcaggagcc acacttgat ggacatcttg | 900 |
| aacagcataa ctatctacac cgatgtgcac agaggatact attactggtc tggacaccag | 960 |
| atcaccgcct ctccagttgg attctccgga cctgagtttg cttttcctct ctatggaact | 1020 |
| atgggaaacg ccgctccaca caacgtatc gttgctcaac taggacaggg tgtctacaga | 1080 |
| accttgtctt ccaccttgta cagaagaccc ttcaatatcg gtcctaacaa ccagcaactt | 1140 |
| tccgttcttg acggaacaga gttcgcctat ggaacctctt ctaacttgcc atccgctgtt | 1200 |
| tacagaaaga gcgaaccgt tgattccttg gacgtgatcc caccacagaa caacaatgtg | 1260 |
| ccacccaggg ctggattctc ccacaggctt agccacgtgt ccatgttccg ttccggattc | 1320 |
| agcaacagtt ccgtgagcat catcagagct cctatgttct cttggattca ccgttctgcc | 1380 |
| gagttcaaca acatcatcgc atctgatagt attactcaaa tccctgccgt gaagggaaac | 1440 |
| ttccttttca atggaagcgt tatcagcgga ccaggattca ctggcggaga tcttgtgaga | 1500 |
| cttaacagct ctggcaacaa cattcagaat agaggctaca tcgaagttcc tatccacttc | 1560 |
| ccatccacat ctactagata cagagttagg gttagatacg cctctgtgac cccaatccac | 1620 |
| cttaacgtga actggggcaa ttcatctatc ttctccaaca ccgttccagc tactgctacc | 1680 |
| tcactcgata atcttcaatc cagcgatttt ggttacttcg aaagtgccaa cgcattcact | 1740 |
| tcttcattgg gcaacatcgt gggtgttagg aatttcagcg gtactgcagg agtgatcatt | 1800 |
| gacagattcg agttcattcc tgttactgcc actcttgagg ctgagtacaa tctttaa | 1857 |

<210> SEQ ID NO 38
<211> LENGTH: 1857
<212> TYPE: DNA
<213> ORGANISM: Artificial Sequence
<220> FEATURE:
<223> OTHER INFORMATION: Mut-N04

<400> SEQUENCE: 38

| | | | | | |
|---|---|---|---|---|---|
| atggacaaca | acccaaacat | caacgaatgc | attccataca | actgcttgag | taacccagaa | 60 |
| gttgaagtac | ttggtggaga | acgcattgaa | accggttaca | ctcccatcga | catctccttg | 120 |
| tccttgacac | agtttctgct | cagcgagttc | gtgccaggag | ctgggttcgt | tctcggacta | 180 |
| gttgacatca | tctggggtat | ctttggtcca | tctcaatggg | atgcattcct | ggtgcaaatt | 240 |
| gagcagttga | tcaaccagag | gatcgaagag | ttcgccagga | accaggccat | ctctcgtttg | 300 |
| gaaggattga | gcaatctcta | ccaaatctat | gcagagagct | tcagagagtg | ggaagccgat | 360 |
| cctactaacc | cagctctccg | cgaggaaatg | cgtattcaat | caacgacat | gaacagcgcc | 420 |
| ttgaccacag | ctatcccatt | gttcgcagtc | cagaactacc | aagttcctct | cttgtccgtg | 480 |
| tacgttcaag | cagctaatct | tcacctcagc | gtgcttcgag | acgttagcgt | gtttgggcaa | 540 |
| agatggggat | tcgatgctac | caccatcaat | agccgttaca | acgaccttac | taggctgatt | 600 |
| ggaaactaca | ccgactacgc | tgttcgttgg | tacaacactg | gcttggagcg | tgtctggggt | 660 |
| cctgattcta | gagattgggt | gagatacaac | cagttcagga | gagaattgac | cctcacagtt | 720 |
| ttggacattg | tggctctctt | cagcaactat | gactccagac | gttaccctat | ccgtacagtg | 780 |
| tcccaactta | ccagagaaat | ctacactaac | ccagttcttg | agaacttcga | cggtagcttc | 840 |
| cgtggtatgg | cccagaggat | cgaaagatcc | atcaggagcc | cacacttgat | ggacatcttg | 900 |
| aacagcataa | ctatctacac | cgatgtgcac | agaggatact | attactggtc | tggacaccag | 960 |
| atcaccgcct | ctccagttgg | attctccgga | cctgagtttg | cttttcctct | ctatggaact | 1020 |
| atgggaaacg | ccgctccaca | acaacgtatc | gttgctcaac | taggacaggg | tgtctacaga | 1080 |
| accttgtctt | ccaccttgta | cagaagaccc | ttcaatatcg | gtcctaacaa | ccagcaactt | 1140 |
| tccgttcttg | acggaacaga | gttcgcctat | ggaacctctt | ctaacttgcc | atccgctgtt | 1200 |
| tacagaaaga | gcggaaccgt | tgattccttg | gacgtgatcc | caccacagaa | caacaatgtg | 1260 |
| ccacccaggg | ctggattctc | ccacaggctt | agccacgtgt | ccatgttccg | ttccggattc | 1320 |
| agcaacagtt | ccgtgagcat | catcagagct | cctatgttct | cttggattca | ccgttctgcc | 1380 |
| gagttcaaca | acatcatcgc | atctgatagt | attactcaaa | tccctgccgt | gaagggaaac | 1440 |
| ttcctttca | atggaagcgt | tatcagcgga | ccaggattca | ctggcggaga | tcttgtgaga | 1500 |
| cttaacagct | ctggcaacaa | cattcagaat | agaggctaca | tcgaagttcc | tatccacttc | 1560 |
| ccatccacat | ctactagata | cagagttagg | gttagatacg | cctctgtgac | cccaatccac | 1620 |
| cttaacgtga | actggggcaa | ttcatctatc | ttctccaaca | ccgttccagc | tactgctacc | 1680 |
| tcactcgata | tcttcaatc | cagcgatttt | ggttacttcg | aaagtgccaa | cgcattcact | 1740 |
| tcttcattgg | gcaacatcgt | gggtgttagg | aatttcagcg | gtactgcagg | agtgatcatt | 1800 |
| gacagattcg | agttcattcc | tgttactgcc | actcttgagg | ctgagtacaa | tctttaa | 1857 |

<210> SEQ ID NO 39
<211> LENGTH: 1857
<212> TYPE: DNA
<213> ORGANISM: Artificial Sequence
<220> FEATURE:
<223> OTHER INFORMATION: Mut-N05

<400> SEQUENCE: 39

```
atggacaaca acccaaacat caacgaatgc attccataca actgcttgag taacccagaa        60
gttgaagtac ttggtggaga acgcattgaa accggttaca ctcccatcga catctccttg       120
tccttgacac agtttctgct cagcgagttc gtgccaggag ctgggttcgt tctcggacta       180
gttgacatca tctggggtat ctttggtcca tctcaatggg atgcattcct ggtgcaaatt       240
gagcagttga tcaaccagag gatcgaagag ttcgccagga accaggccat ctctcgtttg       300
gaaggattga gcaatctcta ccaaatctat gcagagagct tcagagcttg ggaagccgat       360
cctactaacc cagctctccg cgaggaaatg cgtattcaat tcaacgacat gaacagcgcc       420
ttgaccacag ctatcccatt gttcgcagtc cagaactacc aagttcctct cttgtccgtg       480
tacgttcaag cagctaatct tcacctcagc gtgcttcgag acgttagcgt gtttgggcaa       540
agatggggat tcgatgctac caccatcaat agccgttaca acgaccttac taggctgatt       600
ggaaactaca ccgactacgc tgttcgttgg tacaacactg gcttggagcg tgtctggggt       660
cctgattcta gagattgggt gagatacaac cagttcagga gagaattgac cctcacagtt       720
ttggacattg tgtctctctt cagcaactat gactccagac gttaccctat ccgtacagtg       780
tcccaactta ccagagaaat ctacactaac ccagttcttg agaacttcga cggtagcttc       840
cgtggtatgg cccagaggat cgaaagatcc atcaggagcc cacacttgat ggacatcttg       900
aacagcataa ctatctacac cgatgtgcac agaggatact attactggtc tggacaccag       960
atcaccgcct ctccagttgg attctccgga cctgagtttg cttttcctct ctatggaact      1020
atgggaaacg ccgctccaca acaacgtatc gttgctcaac taggacaggg tgtctacaga      1080
accttgtctt ccaccttgta cagaagaccc ttcaatatcg gtcctaacaa ccagcaactt      1140
tccgttcttg acgaacagaa gttcgcctat ggaacctctt ctaacttgcc atccgctgtt      1200
tacagaaaga gcggaaccgt tgattccttg acgtgatcc caccacagaa caacaatgtg       1260
ccacccaggg ctggattctc ccacaggctt agccacgtgt ccatgttccg ttccggattc      1320
agcaacagtt ccgtgagcat catcagagct cctatgttct cttggattca ccgttctgcc      1380
gagttcaaca acatcatcgc atctgatagt attactcaaa tccctgccgt gaagggaaac      1440
ttccttttca atggaagcgt tatcagcgga ccaggattca ctggcggaga tcttgtgaga      1500
cttaacagct ctggcaacaa cattcagaat agaggctaca tcgaagttcc tatccacttc      1560
ccatccacat ctactagata cagagttagg gttagatacg cctctgtgac cccaatccac      1620
cttaacgtga actggggcaa ttcatctatc ttctccaaca ccgttccagc tactgctacc      1680
tcactcgata atcttcaatc cagcgatttt ggttacttcg aaagtgccaa cgcattcact      1740
tcttcattgg gcaacatcgt gggtgttagg aatttcagcg gtactgcagg agtgatcatt      1800
gacagattcg agttcattcc tgttactgcc actcttgagg ctgagtacaa tctttaa       1857
```

<210> SEQ ID NO 40
<211> LENGTH: 1857
<212> TYPE: DNA
<213> ORGANISM: Artificial Sequence
<220> FEATURE:
<223> OTHER INFORMATION: Mut-N06

<400> SEQUENCE: 40

```
atggacaaca acccaaacat caacgaatgc attccataca actgcttgag taacccagaa        60
gttgaagtac ttggtggaga acgcattgaa accggttaca ctcccatcga catctccttg       120
tccttgacac agtttctgct cagcgagttc gtgccaggag ctgggttcgt tctcggacta       180
```

```
gttgacatca tctggggtat ctttggtcca tctcaatggg atgcattcct ggtgcaaatt    240
gagcagttga tcaaccagag gatcgaagag ttcgccagga accaggccat ctctcgtttg    300
gaaggattga gcaatctcta ccaaatctat gcagagagct tcagagagtg ggaagccgat    360
cctactaacc cagctctccg cgaggaaatg cgtattcaat tcaacgacat gaacagcgcc    420
ttgaccacag ctatcccatt gttcgcagtc cagaactacc aagttcctct cttgtccgtg    480
tacgttcaag cagctaatct tcacctcagc gtgcttcgag acgttagcgt gtttgggcaa    540
agatggggat tcgatgctgc aaccatcaat agccgttaca acgacttac taggctgatt    600 ggaaactaca ccgactacgc tgttcgttgg tacaacactg gcttggagcg tgtctggggt    660
cctgattcta gagattgggt gagatacaac cagttcagga gagaattgac cctcacagtt    720
ttggacattg tgtctctctt cagcaactat gactccagac gttaccctat ccgtacagtg    780
tcccaactta ccagagaaat ctacactaac ccagttcttg agaacttcga cggtagcttc    840
cgtggtatgg cccagaggat cgaaagatcc atcaggagcc acacttgat ggacatcttg    900 aacagcataa ctatctacac cgatgtgcac agaggatact attactggtc tggacaccag    960
atcaccgcct ctccagttgg attctccgga cctgagtttg cttttcctct ctatggaact   1020
atgggaaacg ccgctccaca caacgtatc gttgctcaac taggacaggg tgtctacaga   1080
accttgtctt ccaccttgta cagaagaccc ttcaatatcg gtcctaacaa ccagcaactt   1140
tccgttcttg acggaacaga gttcgcctat ggaacctctt ctaacttgcc atccgctgtt   1200
tacagaaaga gcggaaccgt tgattccttg acgtgatcc caccacagaa caacaatgtg   1260
ccacccaggg ctggattctc ccacaggctt agccacgtgt ccatgttccg ttccggattc   1320
agcaacagtt ccgtgagcat catcagagct cctatgttct cttggattca ccgttctgcc   1380
gagttcaaca acatcatcgc atctgatagt attactcaaa tccctgccgt gaagggaaac   1440
ttccttttca atgaagcgt tatcagcgga ccaggattca ctggcggaga tcttgtgaga   1500
cttaacagct ctggcaacaa cattcagaat agaggctaca tcgaagttcc tatccacttc   1560
ccatccacat ctactagata cagagttagg gttagatacg cctctgtgac cccaatccac   1620
cttaacgtga actgggcaa ttcatctatc ttctccaaca ccgttccagc tactgctacc   1680
tcactcgata tcttcaatc cagcgatttt ggttacttcg aaagtgccaa cgcattcact   1740
tcttcattgg gcaacatcgt gggtgttagg aatttcagcg gtactgcagg agtgatcatt   1800
gacagattcg agttcattcc tgttactgcc actcttgagg ctgagtacaa tctttaa     1857
```

<210> SEQ ID NO 41
<211> LENGTH: 1857
<212> TYPE: DNA
<213> ORGANISM: Artificial Sequence
<220> FEATURE:
<223> OTHER INFORMATION: Mut-N09

<400> SEQUENCE: 41

```
atggacaaca acccaaacat caacgaatgc attccataca actgcttgag taacccagaa     60
gttgaagtac ttggtggaga acgcattgaa accggttaca ctcccatcga catctccttg    120
tccttgacac agtttctgct cagcgagttc gtgccaggag ctgggttcgt tctcggacta    180
gttgacatca tctggggtat ctttggtcca tctcaatggg atgcattcct ggtgcaaatt    240
gagcagttga tcaaccagag gatcgaagag ttcgccagga accaggccat ctctcgtttg    300
gaaggattga gcaatctcta ccaaatctat gcagagagct tcagagcttg ggaagccgat    360
```

```
cctactaacc cagctctccg cgaggaaatg cgtattcaat tcaacgacat gaacagcgcc    420
ttgaccacag ctatcccatt gttcgcagtc cagaactacc aagttcctct cttgtccgtg    480
tacgttcaag cagctaatct tcacctcagc gtgcttcgag acgttagcgt gtttgggcaa    540
agatggggat tcgatgctgc aaccatcaat agccgttaca acgaccttac taggctgatt    600
ggaaactaca ccgactacgc tgttcgttgg tacaacactg gcttggagcg tgtctggggt    660
cctgattcta gagattgggt gagatacaac cagttcagga gagaattgac cctcacagtt    720
ttggacattg tggctctctt cagcaactat gactccagac gttaccctat ccgtacagtg    780
tcccaactta ccagagaaat ctacactaac ccagttcttg agaacttcga cggtagcttc    840
cgtggtatgg cccagaggat cgaaagatcc atcaggagcc acacttgat  ggacatcttg    900 aacagcataa ctatctacac cgatgtgcac agaggatact attactggtc tggacaccag    960
atcaccgcct ctccagttgg attctccgga cctgagtttg cttttcctct ctatggaact   1020
atgggaaacg ccgctccaca caacgtatc  gttgctcaac taggacaggg tgtctacaga   1080
accttgtctt ccaccttgta cagaagaccc ttcaatatcg gtcctaacaa ccagcaactt   1140
tccgttcttg acggaacaga gttcgcctat ggaacctctt ctaacttgcc atccgctgtt   1200
tacagaaaga gcggaaccgt tgattccttg acgtgatcc  caccacagaa caacaatgtg   1260
ccacccaggg ctggattctc ccacaggctt agccacgtgt ccatgttccg ttccggattc   1320
agcaacagtt ccgtgagcat catcagagct cctatgttct cttggattca ccgttctgcc   1380
gagttcaaca acatcatcgc atctgatagt attactcaaa tccctgccgt gaagggaaac   1440 ttcctttttca atggaagcgt tatcagcgga ccaggattca ctggcggaga tcttgtgaga   1500
cttaacagct ctggcaacaa cattcagaat agaggctaca tcgaagttcc tatccacttc   1560
ccatccacat ctactagata cagagttagg gttagatacg cctctgtgac cccaatccac   1620
cttaacgtga actggggcaa ttcatctatc ttctccaaca ccgttccagc tactgctacc   1680
tcactcgata atcttcaatc cagcgatttt ggttacttcg aaagtgccaa cgcattcact   1740
tcttcattgg gcaacatcgt gggtgttagg aatttcagcg gtactgcagg agtgatcatt   1800
gacagattcg agttcattcc tgttactgcc actcttgagg ctgagtacaa tctttaa     1857
```

<210> SEQ ID NO 42
<211> LENGTH: 1857
<212> TYPE: DNA
<213> ORGANISM: Artificial Sequence
<220> FEATURE:
<223> OTHER INFORMATION: Mut-N10

<400> SEQUENCE: 42

```
atggacaaca acccaaacat caacgaatgc attccataca actgcttgag taacccagaa     60
gttgaagtac ttggtggaga acgcattgaa accggttaca ctcccatcga catctccttg    120
tccttgacac agtttctgct cagcgagttc gtgccaggag ctgggttcgt tctcggacta    180
gttgacatca tctggggtat cttttggtcca tctcaatggg atgcattcct ggtgcaaatt    240
gagcagttga tcaaccagag gatcgaagag ttcgccagga accaggccat ctctcgtttg    300
gaaggattga gcaatctcta ccaaatctat gcagagagct tcagagagtg ggaagccgat    360
cctactaacc cagctctccg cgtggaaatg cgtattcaat tcaacgacat gaacagcgcc    420
ttgaccacag ctatcccatt gttcgcagtc cagaactacc aagttcctct cttgtccgtg    480
tacgttcaag cagctaatct tcacctcagc gtgcttcgag acgttagcgt gtttgggcaa    540
agatggggat tcgatgctac caccatcaat agccgttaca acgaccttac taggctgatt    600
```

```
ggaaactaca ccgactacgc tgttcgttgg tacaacactg gcttggagcg tgtctggggt     660
cctgattcta gagattgggt gagatacaac cagttcagga gagaattgac cctcacagtt     720
ttggacattg tgtctctctt cagcaactat gactccagaa cctaccctat ccgtacagtg     780
tcccaactta ccagagaaat ctacactaac ccagttcttg agaacttcga cggtagcttc     840
cgtggtatgg cccagaggat cgaaagatcc atcaggagcc cacacttgat ggacatcttg     900
aacagcataa ctatctacac cgatgtgcac agaggatact attactggtc tggacaccag     960
atcaccgcct ctccagttgg attctccgga cctgagtttg cttttcctct ctatggaact    1020
atgggaaacg ccgctccaca acaacgtatc gttgctcaac taggacaggg tgtctacaga    1080
accttgtctt ccaccttgta cagaagaccc ttcaatatcg gtcctaacaa ccagcaactt    1140
tccgttcttg acggaacaga gttcgcctat ggaacctctt ctaacttgcc atccgctgtt    1200
tacagaaaga gcggaaccgt tgattccttg gacgtgatcc caccacagaa caacaatgtg    1260
ccacccaggg ctggattctc ccacaggctt agccacgtgt ccatgttccg ttccggattc    1320
agcaacagtt ccgtgagcat catcagagct cctatgttct cttggattca ccgttctgcc    1380
gagttcaaca acatcatcgc atctgatagt attactcaaa tccctgccgt gaagggaaac    1440
ttccttttca atggaagcgt aatcagcgga ccaggattca ctggcggaga tcttgtgaga    1500
cttaacagct ctggcaacaa cattcagaat agaggctaca tcgaagttcc tatccacttc    1560
ccatccacat ctactagata cagagttagg gttagatacg cctctgtgac cccaatccac    1620
cttaacgtga actggggcaa ttcatctatc ttctccaaca ccgttccagc tactgctacc    1680
tcactcgata atcttcaatc cagcgatttt ggttacttcg aaagtgccaa cgcattcact    1740
tcttcattgg gcaacatcgt gggtgttagg aatttcagcg gtactgcagg agtgatcatt    1800
gacagattcg agttcattcc tgttactgcc actcttgagg ctgagtacaa tctttaa      1857
```

<210> SEQ ID NO 43
<211> LENGTH: 1857
<212> TYPE: DNA
<213> ORGANISM: Artificial Sequence
<220> FEATURE:
<223> OTHER INFORMATION: Mut-N12

<400> SEQUENCE: 43

```
atggacaaca acccaaacat caacgaatgc attccataca actgcttgag taacccagaa      60
gttgaagtac ttggtggaga acgcattgaa accggttaca ctcccatcga catctccttg     120
tccttgacac agtttctgct cagcgagttc gtgccaggag ctgggttcgt tctcggacta     180
gttgacatca tctggggtat ctttggtcca tctcaatggg atgcattcct ggtgcaaatt     240
gagcagttga tcaaccagag gatcgaagag ttcgccagga accaggccat ctctcgtttg     300
gaaggattga gcaatctcta ccaaatctat gcagagagct tcagagagtg ggaagccgat     360
cctactaacc cagctctccg cgtggaaatg cgtattcaat tcaacgacat gaacagcgcc     420
ttgaccacag ctatcccatt gttcgcagtc cagaactacc aagttcctct cttgtccgtg     480
tacgttcaag cagctaatct tcacctcagc gtgcttcgag acgttagcgt gtttgggcaa     540
agatggggat cgatgctaca ccatcaat agccgttaca cgaccttac taggctgatt     600 ggaaactaca ccgactacgc tgttcgttgg tacaacactg gcttggagcg tgtctggggt     660
cctgattcta gagattggat cagatacaac cagttcagga gagaattgac cctcacagtt     720
ttggacattg tgtctctctt cagcaactat gactccagaa cctaccctat ccgtacagtg     780
```

| | |
|---|---|
| tcccaactta ccagagaaat ctacactaac ccagttcttg agaacttcga cggtagcttc | 840 |
| cgtggtatgg cccagaggat cgaaagatcc atcaggagcc cacacttgat ggacatcttg | 900 |
| aacagcataa ctatctacac cgatgtgcac agaggatact attactggtc tggacaccag | 960 |
| atcaccgcct ctccagttgg attctccgga cctgagtttg cttttcctct ctatggaact | 1020 |
| atgggaaacg ccgctccaca caacgtatc gttgctcaac taggacaggg tgtctacaga | 1080 |
| accttgtctt ccaccttgta cagaagaccc ttcaatatcg gtcctaacaa ccagcaactt | 1140 |
| tccgttcttg acggaacaga gttcgcctat ggaacctctt ctaacttgcc atccgctgtt | 1200 |
| tacagaaaga gcgaaccgt tgattccttg acgtgatcc caccacagaa caacaatgtg | 1260 |
| ccacccaggg ctggattctc ccacaggctt agccacgtgt ccatgttccg ttccggattc | 1320 |
| agcaacagtt ccgtgagcat catcagagct cctatgttct cttggattca ccgttctgcc | 1380 |
| gagttcaaca acatcatcgc atctgatagt attactcaaa tccctgccgt gaagggaaac | 1440 |
| ttccttttca tggaagcgt tatcagcgga ccaggattca ctggcggaga tcttgtgaga | 1500 |
| cttaacagct ctggcaacaa cattcagaat agaggctaca tcgaagttcc tatccacttc | 1560 |
| ccatccacat ctactagata cagagttagg gttagatacg cctctgtgac cccaatccac | 1620 |
| cttaacgtga actgggcaa ttcatctatc ttctccaaca ccgttccagc tactgctacc | 1680 |
| tcactcgata atcttcaatc cagcgatttt ggttacttcg aaagtgccaa cgcattcact | 1740 |
| tcttcattgg gcaacatcgt gggtgttagg aatttcagcg gtactgcagg agtgatcatt | 1800 |
| gacagattcg agttcattcc tgttactgcc actcttgagg ctgagtacaa tcttttaa | 1857 |

<210> SEQ ID NO 44
<211> LENGTH: 1857
<212> TYPE: DNA
<213> ORGANISM: Artificial Sequence
<220> FEATURE:
<223> OTHER INFORMATION: Mut-N14

<400> SEQUENCE: 44

| | |
|---|---|
| atggacaaca acccaaacat caacgaatgc attccataca actgcttgag taacccagaa | 60 |
| gttgaagtac ttggtggaga acgcattgaa accggttaca ctcccatcga catctccttg | 120 |
| tccttgacac agtttctgct cagcgagttc gtgccaggag ctgggttcgt tctcggacta | 180 |
| gttgacatca tctggggtat cttttggtcca tctcaatggg atgcattcct ggtgcaaatt | 240 |
| gagcagttga tcaaccagag gatcgaagag ttcgccagga accaggccat ctctcgtttg | 300 |
| gaaggattga gcaatctcta ccaaatctat gcagagagct tcagagagtg ggaagccgat | 360 |
| cctactaacc cagctctccg cgtggaaatg cgtattcaat tcaacgacat gaacagcgcc | 420 |
| ttgaccacag ctatcccatt gttcgcagtc cagaactacc aagttcctct cttgtccgtg | 480 |
| tacgttcaag cagctaatct tcacctcagc gtgcttcgag acgttagcgt gtttgggcaa | 540 |
| agatggggat cgatgctac caccatcaat agccgttaca cgaccttac taggctgatt | 600 |
| ggaaactaca ccgactacgc tgttcgttgg tacaacactg gcttggagcg tgtctggggt | 660 |
| cctgattcta gagattggat cagatacaac cagttcagga gagaattgac cctcacagtt | 720 |
| ttggacattg tgtctctctt cagcaactat gactccagac gttacccta ccgtacagtg | 780 |
| tcccaactta ccagagaaat ctacactaac ccagttcttg agaacttcga cggtagcttc | 840 |
| cgtggtatgg cccagaggat cgaaagatcc atcaggagcc cacacttgat ggacatcttg | 900 |
| aacagcataa ctatctacac cgatgtgcac agaggatact attactggtc tggacaccag | 960 |
| atcaccgcct ctccagttgg attctccgga cctgagtttg cttttcctct ctatggaact | 1020 |

```
atgggaaacg ccgctccaca acaacgtatc gttgctcaac taggacaggg tgtctacaga   1080
accttgtctt ccaccttgta cagaagaccc ttcaatatcg tcctaacaa ccagcaactt    1140 tccgttcttg acggaacaga gttcgcctat ggaacctctt ctaacttgcc atccgctgtt   1200
tacagaaaga gcggaaccgt tgattccttg acgtgatcc caccacagaa caacaatgtg    1260
ccacccaggg ctggattctc ccacaggctt agccacgtgt ccatgttccg ttccggattc   1320
agcaacagtt ccgtgagcat catcagagct cctatgttct cttggattca ccgttctgcc   1380
gagttcaaca acatcatcgc atctgatagt attactcaaa tccctgccgt gaagggaaac   1440
ttccttttca atgaagcgt tatcagcgga ccaggattca ctggcggaga tcttgtgaga    1500
cttaacagct ctggcaacaa cattcagaat agaggctaca tcgaagttcc tatccacttc   1560
ccatccacat ctactagata cagagttagg gttagatacg cctctgtgac cccaatccac   1620
cttaacgtga actggggcaa ttcatctatc ttctccaaca ccgttccagc tactgctacc   1680
tcactcgata tcttcaatc cagcgatttt ggttacttcg aaagtgccaa cgcattcact    1740
tcttcattgg gcaacatcgt gggtgttagg aatttcagcg gtactgcagg agtgatcatt   1800
gacagattcg agttcattcc tgttactgcc actcttgagg ctgagtacaa tctttaa      1857
```

<210> SEQ ID NO 45
<211> LENGTH: 1857
<212> TYPE: DNA
<213> ORGANISM: Artificial Sequence
<220> FEATURE:
<223> OTHER INFORMATION: Mut-N16

<400> SEQUENCE: 45

```
atggacaaca acccaaacat caacgaatgc attccataca actgcttgag taacccagaa   60
gttgaagtac ttggtggaga acgcattgaa accggttaca ctcccatcga catctccttg   120
tccttgacac agtttctgct cagcgagttc gtgccaggag ctgggttcgt tctcggacta   180
gttgacatca tctggggtat cttttggtcca tctcaatggg atgcattcct ggtgcaaatt   240
gagcagttga tcaaccagag gatcgaagag ttcgccagga accaggccat ctctcgtttg   300
gaaggattga gcaatctcta ccaaatctat gcagagagct tcagagcttg ggaagccgat   360
cctactaacc cagctctccg cgtggaaatg cgtattcaat tcaacgacat gaacagcgcc   420
ttgaccacag ctatcccatt gttcgcagtc cagaactacc aagttcctct cttgtccgtg   480
tacgttcaag cagctaatct tcacctcagc gtgcttcgag acgttagcgt gtttgggcaa   540
agatggggat cgatgctac caccatcaat agccgttaca acgaccttac taggctgatt   600
ggaaactaca ccgactacgc tgttcgttgg tacaacactg gcttggagcg tgtctggggt   660
cctgattcta gagattggat cagatacaac cagttcagga gagaattgac cctcacagtt   720
ttggacattg tgtctctctt cagcaactat gactccagaa cctaccctat ccgtacagtg   780
tcccaactta ccagagaaat ctacactaac ccagttcttg agaacttcga cggtagcttc   840
cgtggtatgg cccagaggat cgaaagatcc atcaggagcc cacacttgat ggacatcttg   900
aacagcataa ctatctacac cgatgtgcac agaggatact attactggtc tggacaccag   960
atcaccgcct ctccagttgg attctccgga cctgagtttg cttttcctct ctatggaact   1020
atgggaaacg ccgctccaca acaacgtatc gttgctcaac taggacaggg tgtctacaga   1080
accttgtctt ccaccttgta cagaagaccc ttcaatatcg tcctaacaa ccagcaactt    1140 tccgttcttg acggaacaga gttcgcctat ggaacctctt ctaacttgcc atccgctgtt   1200
```

| | |
|---|---|
| tacagaaaga gcggaaccgt tgattccttg gacgtgatcc caccacagaa caacaatgtg | 1260 |
| ccacccaggg ctggattctc ccacaggctt agccacgtgt ccatgttccg ttccggattc | 1320 |
| agcaacagtt ccgtgagcat catcagagct cctatgttct cttggattca ccgttctgcc | 1380 |
| gagttcaaca acatcatcgc atctgatagt attactcaaa tccctgccgt gaagggaaac | 1440 |
| ttccttttca atggaagcgt tatcagcgga ccaggattca ctggcggaga tcttgtgaga | 1500 |
| cttaacagct ctggcaacaa cattcagaat agaggctaca tcgaagttcc tatccacttc | 1560 |
| ccatccacat ctactagata cagagttagg gttagatacg cctctgtgac cccaatccac | 1620 |
| cttaacgtga actggggcaa ttcatctatc ttctccaaca ccgttccagc tactgctacc | 1680 |
| tcactcgata atcttcaatc cagcgatttt ggttacttcg aaagtgccaa cgcattcact | 1740 |
| tcttcattgg gcaacatcgt gggtgttagg aatttcagcg gtactgcagg agtgatcatt | 1800 |
| gacagattcg agttcattcc tgttactgcc actcttgagg ctgagtacaa tctttaa | 1857 |

<210> SEQ ID NO 46
<211> LENGTH: 1857
<212> TYPE: DNA
<213> ORGANISM: Artificial Sequence
<220> FEATURE:
<223> OTHER INFORMATION: Mut-N17

<400> SEQUENCE: 46

| | |
|---|---|
| atggacaaca acccaaacat caacgaatgc attccataca actgcttgag taacccagaa | 60 |
| gttgaagtac ttggtggaga acgcattgaa accggttaca ctcccatcga catctccttg | 120 |
| tccttgacac agtttctgct cagcgagttc gtgccaggag ctgggttcgt tctcggacta | 180 |
| gttgacatca tctggggtat ctttggtcca tctcaatggg atgcattcct ggtgcaaatt | 240 |
| gagcagttga tcaaccagag gatcgaagag ttcgccagga accaggccat ctctcgtttg | 300 |
| gaaggattga gcaatctcta ccaaatctat gcagagagct tcagagcttg ggaagccgat | 360 |
| cctactaacc cagctctccg cgtggaaatg cgtattcaat tcaacgacat gaacagcgcc | 420 |
| ttgaccacag ctatcccatt gttcgcagtc cagaactacc aagttcctct cttgtccgtg | 480 |
| tacgttcaag cagctaatct tcacctcagc gtgcttcgag acgttagcgt gtttgggcaa | 540 |
| agatggggat tcgatgctac caccatcaat agccgttaca acgaccttac taggctgatt | 600 |
| ggaaactaca ccgactacgc tgttcgttgg tacaacactg gcttggagcg tgtctggggt | 660 |
| cctgattcta gagattgggt gagatacaac cagttcagga gagaattgac cctcacagtt | 720 |
| ttggacattg tgtctctctt cagcaactat gactccagaa cctaccctat ccgtacagtg | 780 |
| tcccaactta ccagagaaat ctacactaac ccagttcttg agaacttcga cggtagcttc | 840 |
| cgtggtatgg cccagaggat cgaaagatcc atcaggagcc acacttgat ggacatcttg | 900 |
| aacagcataa ctatctacac cgatgtgcac agaggatact attactggtc tggacaccag | 960 |
| atcaccgcct ctccagttgg attctccgga cctgagtttg cttttcctct ctatggaact | 1020 |
| atgggaaacg ccgctccaca caacgtatcg gttgctcaac taggacaggg tgtctacaga | 1080 |
| accttgtctt ccaccttgta cagaagaccc ttcaatatcg gtcctaacaa ccagcaactt | 1140 |
| tccgttcttg acggaacaga gttcgcctat ggaacctctt ctaacttgcc atccgctgtt | 1200 |
| tacagaaaga gcggaaccgt tgattccttg gacgtgatcc caccacagaa caacaatgtg | 1260 |
| ccacccaggg ctggattctc ccacaggctt agccacgtgt ccatgttccg ttccggattc | 1320 |
| agcaacagtt ccgtgagcat catcagagct cctatgttct cttggattca ccgttctgcc | 1380 |
| gagttcaaca acatcatcgc atctgatagt attactcaaa tccctgccgt gaagggaaac | 1440 |

```
ttccttttca atggaagcgt tatcagcgga ccaggattca ctggcggaga tcttgtgaga    1500
cttaacagct ctggcaacaa cattcagaat agaggctaca tcgaagttcc tatccacttc    1560
ccatccacat ctactagata cagagttagg gttagatacg cctctgtgac cccaatccac    1620
cttaacgtga actggggcaa ttcatctatc ttctccaaca ccgttccagc tactgctacc    1680
tcactcgata tcttcaatc cagcgatttt ggttacttcg aaagtgccaa cgcattcact    1740
tcttcattgg gcaacatcgt gggtgttagg aatttcagcg gtactgcagg agtgatcatt    1800
gacagattcg agttcattcc tgttactgcc actcttgagg ctgagtacaa tctttaa       1857
```

<210> SEQ ID NO 47
<211> LENGTH: 1857
<212> TYPE: DNA
<213> ORGANISM: Artificial Sequence
<220> FEATURE:
<223> OTHER INFORMATION: Mut-N24

<400> SEQUENCE: 47

```
atggacaaca acccaaacat caacgaatgc attccataca actgcttgag taacccagaa      60
gttgaagtac ttggtggaga acgcattgaa accggttaca ctcccatcga catctccttg     120
tccttgacac agtttctgct cagcgagttc gtgccaggag ctgggttcgt tctcggacta     180
gttgacatca tctggggtat cttttggtcca tctcaatggg atgcattcct ggtgcaaatt     240
gagcagttga tcaaccagag gatcgaagag ttcgccagga accaggccat ctctcgtttg     300
gaaggattga gcaatctcta ccaaatctat gcagagagct tcagagcttg ggaagccgat     360
cctactaacc cagctctccg cgtggaaatg cgtattcaat tcaacgacat gaacagcgcc     420
ttgaccacag ctatcccatt gttcgcagtc cagaactacc aagttcctct cttgtccgtg     480
tacgttcaag cagctaatct tcacctcagc gtgcttcgag acgttagcgt gtttgggcaa     540
agatggggat tcgatgctac caccatcaat agccgttaca acgacttac taggctgatt      600 ggaaactaca ccgactacgc tgttcgttgg tacaacactg gcttggagcg tgtctggggt     660
cctgattcta gagattggat cagatacaac cagttcagga gagaattgac cctcacagtt     720
ttggacattg tgtctctctt cagcaactat gactccagaa cctaccctat ccgtacagtg     780
tcccaactta ccagagaaat ctacactaac ccagttcttg agaacttcga cggtagcttc     840
cgtggtatgg cccagaggat cgaaagatcc atcaggagcc acacttgat ggacatcttg      900 aacagcataa ctatctacac cgatgtgcac agaggatact attactggtc tggacaccag    960
atcaccgcct ctccagttgg attctccgga cctgagtttg ctttcctct ctatggaact     1020 atgggaaacg ccgctccaca caacgtatc gttgctcaac taggacaggg tgtctacaga     1080
accttgtctt ccaccttgta cagaagaccc ttcaatatcg gtcctaacaa ccaggagctt    1140
ttcgttcttg acggaacaga gttcgcctat ggaacctctt ctaacttgcc atccgctgtt    1200
tacagaaaga gcggaaccgt tgattccttg gacgtgatcc caccacagaa caacaatgtg    1260
ccacccaggg ctgcattctc ccacaggctt agccacgtgt ccatgttccg ttccggattc    1320
agcaacagtt ccgtgagcat catccagagct cctatgttct cttggattca ccgttctgcc    1380
gagttcaaca acatcatcgc atctgatagt attactcaaa tccctgccgt gaagggaaac    1440
ttccttttca atggaagcgt tatcagcgga ccaggattca ctggcggaga tcttgtgaga    1500
cttaacagct ctggcaacaa cattcagaat agaggctaca tcgaagttcc tatccacttc    1560
ccatccacat ctactagata cagagttagg gttagatacg cctctgtgac cccaatccac    1620
```

-continued

| | |
|---|---|
| cttaacgtga actggggcaa ttcatctatc ttctccaaca ccgttccagc tactgctacc | 1680 |
| tcactcgata atcttcaatc cagcgatttt ggttacttcg aaagtgccaa cgcattcact | 1740 |
| tcttcattgg gcaacatcgt gggtgttagg aatttcagcg gtactgcagg agtgatcatt | 1800 |
| gacagattcg agttcattcc tgttactgcc actcttgagg ctgagtacaa tctttaa | 1857 |

<210> SEQ ID NO 48
<211> LENGTH: 1857
<212> TYPE: DNA
<213> ORGANISM: Artificial Sequence
<220> FEATURE:
<223> OTHER INFORMATION: Mut-N27

<400> SEQUENCE: 48

| | |
|---|---|
| atggacaaca acccaaacat caacgaatgc attccataca actgcttgag taacccagaa | 60 |
| gttgaagtac ttggtggaga acgcattgaa accggttaca ctcccatcga catctccttg | 120 |
| tccttgacac agtttctgct cagcgagttc gtgccaggag ctgggttcgt tctcggacta | 180 |
| gttgacatca tctggggtat ctttggtcca tctcaatggg atgcattcct ggtgcaaatt | 240 |
| gagcagttga tcaaccagag gatcgaagag ttcgccagga accaggccat ctctcgtttg | 300 |
| gaaggattga gcaatctcta ccaaatctat gcagagagct tcagagcttg ggaagccgat | 360 |
| cctactaacc cagctctccg cgtggaaatg cgtattcaat tcaacgacat gaacagcgcc | 420 |
| ttgaccacag ctatcccatt gttcgcagtc cagaactacc aagttcctct cttgtccgtg | 480 |
| tacgttcaag cagctaatct tcacctcagc gtgcttcgag acgttagcgt gtttgggcaa | 540 |
| agatggggat cgatgctac caccatcaat agccgttaca cgaccttac taggctgatt | 600 |
| ggaaactaca ccgactacgc tgttcgttgg tacaacactg gcttggagcg tgtctggggt | 660 |
| cctgattcta gagattgggt gagatacaac cagttcagga gagaattgac cctcacagtt | 720 |
| ttggacattg tgtctctctt cagcaactat gactccagaa cctaccctat ccgtacagtg | 780 |
| tcccaactta ccagagaaat ctacactaac ccagttcttg agaacttcga cggtagcttc | 840 |
| cgtggtatgg cccagaggat cgaaagatcc atcaggagcc cacacttgat ggacatcttg | 900 |
| aacagcataa ctatctacac cgatgtgcac agaggatact attactggtc tggacaccag | 960 |
| atcaccgcct ctccagttgg attctccgga cctgagtttg cttttcctct ctatggaact | 1020 |
| atgggaaacg ccgctccaca acaacgtatc gttgctcaac taggacaggg tgtctacaga | 1080 |
| accttgtctt ccaccttgta cagaagaccc ttcaatatcg gtcctaacaa ccaggagctt | 1140 |
| ttcgttcttg acggaacaga gttcgcctat ggaacctctt ctaacttgcc atccgctgtt | 1200 |
| tacagaaaga gcggaaccgt tgattccttg gacgtgatcc caccacagga caacagcgtg | 1260 |
| ccacccaggg ctggattctc ccacaggctt agccacgtgt ccatgttccg ttccggattc | 1320 |
| agcaacagtt ccgtgagcat catcagagct cctatgttct cttggattca ccgttctgcc | 1380 |
| gagttcaaca acatcatcgc atctgatagt attactcaaa tccctgccgt gaagggaaac | 1440 |
| ttcctttcca atggaagcgt tatcagcgga ccaggattca ctggcggaga tcttgtgaga | 1500 |
| cttaacagct ctggcaacaa cattcagaat agaggctaca tcgaagttcc tatccacttc | 1560 |
| ccatccacat ctactagata cagagttagg gttagatacg cctctgtgac cccaatccac | 1620 |
| cttaacgtga actggggcaa ttcatctatc ttctccaaca ccgttccagc tactgctacc | 1680 |
| tcactcgata atcttcaatc cagcgatttt ggttacttcg aaagtgccaa cgcattcact | 1740 |
| tcttcattgg gcaacatcgt gggtgttagg aatttcagcg gtactgcagg agtgatcatt | 1800 |
| gacagattcg agttcattcc tgttactgcc actcttgagg ctgagtacaa tctttaa | 1857 |

<210> SEQ ID NO 49
<211> LENGTH: 1857
<212> TYPE: DNA
<213> ORGANISM: Artificial Sequence
<220> FEATURE:
<223> OTHER INFORMATION: Mut-N28

<400> SEQUENCE: 49

```
atggacaaca acccaaacat caacgaatgc attccataca actgcttgag taacccagaa      60
gttgaagtac ttggtggaga acgcattgaa accggttaca ctcccatcga catctccttg     120
tccttgacac agtttctgct cagcgagttc gtgccaggag ctgggttcgt tctcggacta     180
gttgacatca tctggggtat ctttggtcca tctcaatggg atgcattcct ggtgcaaatt     240
gagcagttga tcaaccagag gatcgaagag ttcgccagga accaggccat ctctcgtttg     300
gaaggattga gcaatctcta ccaaatctat gcagagagct tcagagagtg ggaagccgat     360
cctactaacc cagctctccg cgaggaaatg cgtattcaat tcaacgacat gaacagcgcc     420
ttgaccacag ctatcccatt gttcgcagtc cagaactacc aagttcctct cttgtccgtg     480
tacgttcaag cagctaatct tcacctcagc gtgcttcgag acgttagcgt gtttgggcaa     540
agatggggat tcgatgctgc aaccatcaat agccgttaca cgaccttac taggctgatt     600
ggaaactaca ccgactacgc tgttcgttgg tacaacactg gcttggagcg tgtctggggt     660
cctgattcta gagattgggt gagatacaac cagttcagga gagaattgac cctcacagtt     720
ttggacattg tgtctctctt cagcaactat gactccagac gttaccctat ccgtacagtg     780
tcccaactta ccagagaaat ctacactaac ccagttcttg agaacttcga cggtagcttc     840
cgtggtatgg cccagaggat cgaaagatcc atcaggagcc acacttgat ggacatcttg      900
aacagcataa ctatctacac cgatgtgcac agaggatact attactggtc tggacaccag     960
atcaccgcct ctccagttgg attctccgga cctgagtttg cttttcctct cttcggaaac    1020
gctggaaacg ccgctccaca acaacgtatc gttgctcaac taggacaggg tgtctacaga    1080
accttgtctt ccaccttgta cagaagaccc ttcaatatcg gtcctaacaa ccagcaactt    1140
tccgttcttg acggaacaga gttcgcctat ggaacctctt ctaacttgcc atccgctgtt    1200
tacagaaaga gcggaaccgt tgattccttg gacgtgatcc caccacagaa caacaatgtg    1260
ccacccaggg ctggattctc ccacaggctt agccacgtgt ccatgttccg ttccggattc    1320
agcaacagtt ccgtgagcat catcagagct cctatgttct cttggattca ccgttctgcc    1380
gagttcaaca catcatcgc atctgatagt attactcaaa tccctgccgt gaagggaaac    1440
ttccttttca atggaagcgt tatcagcgga ccaggattca ctggcggaga tcttgtgaga    1500
cttaacagct ctggcaacaa cattcagaat agaggctaca tcgaagttcc tatccacttc    1560
ccatccacat ctactagata cagagttagg gttagatacg cctctgtgac cccaatccac    1620
cttaacgtga actggggcaa ttcatctatc ttctccaaca ccgttccagc tactgctacc    1680
tcactcgata atcttcaatc cagcgatttt ggttacttcg aaagtgccaa cgcattcact    1740
tcttcattgg gcaacatcgt gggtgttagg aatttcagcg gtactgcagg agtgatcatt    1800
gacagattcg agttcattcc tgttactgcc actcttgagg ctgagtacaa tctttaa      1857
```

<210> SEQ ID NO 50
<211> LENGTH: 1857
<212> TYPE: DNA
<213> ORGANISM: Artificial Sequence
<220> FEATURE:

<223> OTHER INFORMATION: Mut-N29

<400> SEQUENCE: 50

```
atggacaaca acccaaacat caacgaatgc attccataca actgcttgag taacccagaa    60
gttgaagtac ttggtggaga acgcattgaa accggttaca ctcccatcga catctccttg   120
tccttgacac agtttctgct cagcgagttc gtgccaggag ctgggttcgt tctcggacta   180
gttgacatca tctggggtat ctttggtcca tctcaatggg atgcattcct ggtgcaaatt   240
gagcagttga tcaaccagag gatcgaagag ttcgccagga accaggccat ctctcgtttg   300
gaaggattga gcaatctcta ccaaatctat gcagagagct tcagagagtg ggaagccgat   360
cctactaacc cagctctccg cgtggaaatg cgtattcaat tcaacgacat gaacagcgcc   420
ttgaccacag ctatcccatt gttcgcagtc cagaactacc aagttcctct cttgtccgtg   480
tacgttcaag cagctaatct tcacctcagc gtgcttcgag acgttagcgt gtttgggcaa   540
agatggggat tcgatgctac caccatcaat agccgttaca cgaccttac taggctgatt    600
ggaaactaca ccgactacgc tgttcgttgg tacaacactg gcttggagcg tgtctggggt   660
cctgattcta gagattgggt gagatacaac cagttcagga gagaattgac cctcacagtt   720
ttggacattg tgtctctctt cagcaactat gactccagac gttaccctat ccgtacagtg   780
tcccaactta ccagagaaat ctacactaac ccagttcttg agaacttcga cggtagcttc   840
cgtggtatgg cccagaggat cgaaagatcc atcaggagcc acacttgat ggacatcttg    900
aacagcataa ctatctacac cgatgtgcac agaggatact attactggtc tggacaccag   960
atcaccgcct ctccagttgg attctccgga cctgagtttg cttttcctct ctatggaact  1020
atgggaaacg ccgctccaca caacgtatc gttgctcaac taggacaggg tgtctacaga   1080
accttgtctt ccaccttgta cagaagaccc ttcaatatcg gtcctaacaa ccagcaactt  1140
tccgttcttg acggaacaga gttcgcctat ggaacctctt ctaacttgcc atccgctgtt  1200
tacagaaaga gcggaaccgt tgattccttg gacgtgatcc caccacagga taacagcgtg  1260
ccacccaggg ctggattctc ccacaggctt agccacgtgt ccatgttccg ttccggattc  1320
agcaacagtt ccgtgagcat catcagagct cctatgttct cttggattca ccgttctgcc  1380
gagttcaaca acatcatcgc atctgatagt attactcaaa tccctgccgt gaagggaaac  1440
ttccttttca tggaagcgt tatcagcgga ccaggattca ctggcggaga tcttgtgaga   1500
cttaacagct ctggcaacaa cattcagaat agaggctaca tcgaagttcc tatccacttc  1560
ccatccacat ctactagata cagagttagg gttagatacg cctctgtgac cccaatccac  1620
cttaacgtga actggggcaa ttcatctatc ttctccaaca ccgttccagc tactgctacc  1680
tcactcgata tcttcaatc cagcgatttt ggttacttcg aaagtgccaa cgcattcact   1740
tcttcattgg gcaacatcgt gggtgttagg aatttcagcg gtactgcagg agtgatcatt  1800
gacagattcg agttcattcc tgttactgcc actcttgagg ctgagtacaa tctttaa     1857
```

<210> SEQ ID NO 51
<211> LENGTH: 1857
<212> TYPE: DNA
<213> ORGANISM: Artificial Sequence
<220> FEATURE:
<223> OTHER INFORMATION: Mut-N31

<400> SEQUENCE: 51

```
atggacaaca acccaaacat caacgaatgc attccataca actgcttgag taacccagaa    60
gttgaagtac ttggtggaga acgcattgaa accggttaca ctcccatcga catctccttg   120
```

```
tccttgacac agtttctgct cagcgagttc gtgccaggag ctgggttcgt tctcggacta      180
gttgacatca tctggggtat ctttggtcca tctcaatggg atgcattcct ggtgcaaatt      240
gagcagttga tcaaccagag gatcgaagag ttcgccagga accaggccat ctctcgtttg      300
gaaggattga gcaatctcta ccaaatctat gcagagagct tcagagcttg ggaagccgat      360
cctactaacc cagctctccg cgaggaaatg cgtattcaat tcaacgacat gaacagcgcc      420
ttgaccacag ctatcccatt gttcgcagtc cagaactacc aagttcctct cttgtccgtg      480
tacgttcaag cagctaatct tcacctcagc gtgcttcgag acgttagcgt gtttgggcaa      540
agatggggat tcgatgctac caccatcaat agccgttaca acgacttac taggctgatt      600 ggaaactaca ccgactacgc tgttcgttgg tacaacactg gcttggagcg tgtctggggt      660
cctgattcta gagattgggt gagatacaac cagttcagga gagaattgac cctcacagtt      720
ttggacattg tgtctctctt cagcaactat gactccagac gttaccctat ccgtacagtg      780
tcccaactta ccagagaaat ctacactaac ccagttcttg agaacttcga cggtagcttc      840
cgtggtatgg cccagaggat cgaaagatcc atcaggagcc cacacttgat ggacatcttg      900
aacagcataa ctatctacac cgatgtgcac agaggatact attactggtc tggacaccag      960
atcaccgcct ctccagttgg attctccgga cctgagtttg cttttcctct ctatggaact     1020
atgggaaacg ccgctccaca caacgtatc gttgctcaac taggacaggg tgtctacaga     1080
accttgtctt ccaccttgta cagaagaccc ttcaatatcg gtcctaacaa ccaggagctt     1140
ttcgttcttg acggaacaga gttcgcctat ggaacctctt ctaacttgcc atccgctgtt     1200
tacagaaaga gcggaaccgt tgattccttg gacgtgatcc caccacagaa caacaatgtg     1260
ccacccaggg ctggattctc ccacaggctt agccacgtgt ccatgttccg ttccggattc     1320
agcaacagtt ccgtgagcat catcagagct cctatgttct cttggattca ccgttctgcc     1380
gagttcaaca acatcatcgc atctgatagt attactcaaa tccctgccgt gaagggaaac     1440 ttcctttca atggaagcgt tatcagcgga ccaggattca ctggcggaga tcttgtgaga     1500
cttaacagct ctggcaacaa cattcagaat agaggctaca tcgaagttcc tatccacttc     1560
ccatccacat ctactagata cagagttagg gttagatacg cctctgtgac cccaatccac     1620
cttaacgtga actggggcaa ttcatctatc ttctccaaca ccgttccagc tactgctacc     1680
tcactcgata atcttcaatc cagcgatttt ggttacttcg aaagtgccaa cgcattcact     1740
tcttcattgg gcaacatcgt gggtgttagg aatttcagcg gtactgcagg agtgatcatt     1800
gacagattcg agttcattcc tgttactgcc actcttgagg ctgagtacaa tctttaa       1857
```

<210> SEQ ID NO 52
<211> LENGTH: 1857
<212> TYPE: DNA
<213> ORGANISM: Artificial Sequence
<220> FEATURE:
<223> OTHER INFORMATION: Mut-N32

<400> SEQUENCE: 52

```
atggacaaca acccaaacat caacgaatgc attccataca actgcttgag taacccagaa       60
gttgaagtac ttggtggaga acgcattgaa accggttaca ctcccatcga catctccttg      120
tccttgacac agtttctgct cagcgagttc gtgccaggag ctgggttcgt tctcggacta      180
gttgacatca tctggggtat ctttggtcca tctcaatggg atgcattcct ggtgcaaatt      240
gagcagttga tcaaccagag gatcgaagag ttcgccagga accaggccat ctctcgtttg      300
```

```
gaaggattga gcaatctcta ccaaatctat gcagagagct tcagagcttg ggaagccgat      360
cctactaacc cagctctccg cgtggaaatg cgtattcaat tcaacgacat gaacagcgcc      420
ttgaccacag ctatcccatt gttcgcagtc cagaactacc aagttcctct cttgtccgtg      480
tacgttcaag cagctaatct tcacctcagc gtgcttcgag acgttagcgt gtttgggcaa      540
agatggggat tcgatgctgc aaccatcaat agccgttaca acgaccttac taggctgatt      600
ggaaactaca ccgactacgc tgttcgttgg tacaacactg gcttggagcg tgtctggggt      660
cctgattcta gagattgggt gagatacaac cagttcagga gagaattgac cctcacagtt      720
ttggacattg tggctctctt cagcaactat gactccagac gttaccctat ccgtacagtg      780
tcccaactta ccagagaaat ctacactaac ccagttcttg agaacttcga cggtagcttc      840
cgtggtatgg cccagaggat cgaaagatcc atcaggagcc acacttgat ggacatcttg       900 aacagcataa ctatctacac cgatgtgcac agaggatact attactggtc tggacaccag      960
atcaccgcct ctccagttgg attctccgga cctgagtttg cttttcctct ctatggaact     1020
atgggaaacg ccgctccaca acaacgtatc gttgctcaac taggacaggg tgtctacaga     1080
accttgtctt ccaccttgta cagaagaccc ttcaatatcg gtcctaacaa ccagcaactt     1140
tccgttcttg acgaacaga gttcgcctat ggaacctctt ctaacttgcc atccgctgtt      1200
tacagaaaga gcggaaccgt tgattccttg gacgtgatcc caccacagaa caacaatgtg     1260
ccacccaggg ctgattctc ccacaggctt agccacgtgt ccatgttccg ttccggattc      1320
agcaacagtt ccgtgagcat catcagagct cctatgttct cttggattca ccgttctgcc     1380
gagttcaaca acatcatcgc atctgatagt attactcaaa tccctgccgt gaagggaaac     1440
ttccttttca atggaagcgt tatcagcgga ccaggattca ctggcggaga tcttgtgaga     1500
cttaacagct ctggcaacaa cattcagaat agaggctaca tcgaagttcc tatccacttc     1560
ccatccacat ctactagata cagagttagg gttagatacg cctctgtgac cccaatccac     1620
cttaacgtga actggggcaa ttcatctatc ttctccaaca ccgttccagc tactgctacc     1680
tcactcgata atcttcaatc cagcgatttt ggttacttcg aaagtgccaa cgcattcact     1740
tcttcattgg gcaacatcgt gggtgttagg aatttcagcg gtactgcagg agtgatcatt     1800
gacagattcg agttcattcc tgttactgcc actcttgagg ctgagtacaa tctttaa       1857
```

<210> SEQ ID NO 53
<211> LENGTH: 1857
<212> TYPE: DNA
<213> ORGANISM: Artificial Sequence
<220> FEATURE:
<223> OTHER INFORMATION: Mut-N33

<400> SEQUENCE: 53

```
atggacaaca acccaaacat caacgaatgc attccataca actgcttgag taacccagaa       60
gttgaagtac ttggtggaga acgcattgaa accggttaca ctcccatcga catctccttg      120
tccttgacac agtttctgct cagcgagttc gtgccaggag ctgggttcgt tctcggacta      180
gttgacatca tctggggtat ctttggtcca tctcaatggg atgcattcct ggtgcaaatt      240
gagcagttga tcaaccagag gatcgaagag ttcgccagga accaggccat ctctcgtttg      300
gaaggattga gcaatctcta ccaaatctat gcagagagct tcagagcttg ggaagccgat      360
cctactaacc cagctctccg cgaggaaatg cgtattcaat tcaacgacat gaacagcgcc      420
ttgaccacag ctatcccatt gttcgcagtc cagaactacc aagttcctct cttgtccgtg      480
tacgttcaag cagctaatct tcacctcagc gtgcttcgag acgttagcgt gtttgggcaa      540
```

```
agatggggat tcgatgctgc aaccatcaat agccgttaca acgaccttac taggctgatt       600
ggaaactaca ccgactacgc tgttcgttgg tacaacactg gcttggagcg tgtctggggt       660
cctgattcta gagattgggt gagatacaac cagttcagga gagaattgac cctcacagtt       720
ttggacattg tggctctctt cagcaactat gactccagac gttaccctat ccgtacagtg       780
tcccaactta ccagagaaat ctacactaac ccagttcttg agaacttcga cggtagcttc       840
cgtggtatgg cccagaggat cgaaagatcc atcaggagcc acacttgat ggacatcttg        900 aacagcataa ctatctacac cgatgtgcac agaggatact attactggtc tggacaccag       960
atcaccgcct ctccagttgg attctccgga cctgagtttg cttttcctct cttcggaaac      1020
gctggaaacg ccgctccaca acaacgtatc gttgctcaac taggacaggg tgtctacaga      1080
accttgtctt ccaccttgta cagaagaccc ttcaatatcg gtcctaacaa ccagcaactt      1140
tccgttcttg acggaacaga gttcgcctat ggaacctctt ctaacttgcc atccgctgtt      1200
tacagaaaga gcggaaccgt tgattccttg gacgtgatcc caccacagaa caacaatgtg      1260
ccacccaggg ctggattctc ccacaggctt agccacgtgt ccatgttccg ttccggattc      1320
agcaacagtt ccgtgagcat catcagagct cctatgttct cttggattca ccgttctgcc      1380
gagttcaaca acatcatcgc atctgatagt attactcaaa tccctgccgt gaagggaaac      1440
ttccttttca tggaagcgt tatcagcgga ccaggattca ctggcggaga tcttgtgaga       1500
cttaacagct ctggcaacaa cattcagaat agaggctaca tcgaagttcc tatccacttc      1560
ccatccacat ctactagata cagagttagg gttagatacg cctctgtgac cccaatccac      1620
cttaacgtga actggggcaa ttcatctatc ttctccaaca ccgttccagc tactgctacc      1680
tcactcgata tcttcaatc cagcgatttt ggttacttcg aaagtgccaa cgcattcact       1740
tcttcattgg gcaacatcgt gggtgttagg aatttcagcg gtactgcagg agtgatcatt      1800
gacagattcg agttcattcc tgttactgcc actcttgagg ctgagtacaa tctttaa        1857
```

<210> SEQ ID NO 54
<211> LENGTH: 1857
<212> TYPE: DNA
<213> ORGANISM: Artificial Sequence
<220> FEATURE:
<223> OTHER INFORMATION: Mut-N35

<400> SEQUENCE: 54

```
atggacaaca acccaaacat caacgaatgc attccataca actgcttgag taacccagaa        60
gttgaagtac ttggtggaga acgcattgaa accggttaca ctcccatcga catctccttg       120
tccttgacac agtttctgct cagcgagttc gtgccaggag ctgggttcgt tctcggacta       180
gttgacatca tctggggtat ctttggtcca tctcaatggg atgcattcct ggtgcaaatt       240
gagcagttga tcaaccagag gatcgaagag ttcgccagga accaggccat ctctcgtttg       300
gaaggattga gcaatctcta ccaaatctat gcagagagct tcagagagtg gaagccgat        360 cctactaacc cagctctccg cgaggaaatg cgtattcaat tcaacgacat gaacagcgcc       420
ttgaccacag ctatcccatt gttcgcagtc cagaactacc aagttcctct cttgtccgtg       480
tacgttcaag cagctaatct tcacctcagc gtgcttcgag acgttagcgt gtttgggcaa       540
agatggggat tcgatgctac caccatcaat agccgttaca acgaccttac taggctgatt       600
ggaaactaca ccgactacgc tgttcgttgg tacaacactg gcttggagcg tgtctggggt       660
cctgattcta gagattgggt gagatacaac cagttcagga gagaattgac cctcacagtt       720
```

```
ttggacattg tggctctctt cagcaactat gactccagac gttaccctat ccgtacagtg      780
tcccaactta ccagagaaat ctacactaac ccagttcttg agaacttcga cggtagcttc      840
cgtggtatgg cccagaggat cgaaagatcc atcaggagcc cacacttgat ggacatcttg      900
aacagcataa ctatctacac cgatgtgcac agaggatact attactggtc tggacaccag      960
atcaccgcct ctccagttgg attctccgga cctgagtttg cttttcctct cttcggaaac     1020
gctggaaacg ccgctccaca caacgtatc gttgctcaac taggacaggg tgtctacaga      1080
accttgtctt ccaccttgta cagaagaccc ttcaatatcg gtcctaacaa ccagcaactt     1140
tccgttcttg acggaacaga gttcgcctat ggaacctctt ctaacttgcc atccgctgtt     1200
tacagaaaga gcggaaccgt tgattccttg gacgtgatcc caccacagga taacagcgtg     1260
ccacccaggg ctggattctc ccacaggctt agccacgtgt ccatgttccg ttccggattc     1320
agcaacagtt ccgtgagcat catcagagct cctatgttct cttggattca ccgttctgcc     1380
gagttcaaca acatcatcgc atctgatagt attactcaaa tccctgccgt gaagggaaac     1440
ttccttttca atgaagcgt tatcagcgga ccaggattca ctggcggaga tcttgtgaga      1500
cttaacagct ctggcaacaa cattcagaat agaggctaca tcgaagttcc tatccacttc     1560
ccatccacat ctactagata cagagttagg gttagatacg cctctgtgac cccaatccac     1620
cttaacgtga actggggcaa ttcatctatc ttctccaaca ccgttccagc tactgctacc     1680
tcactcgata atcttcaatc cagcgatttt ggttacttcg aaagtgccaa cgcattcact     1740
tcttcattgg gcaacatcgt gggtgttagg aatttcagcg gtactgcagg agtgatcatt     1800
gacagattcg agttcattcc tgttactgcc actcttgagg ctgagtacaa tctttaa       1857
```

<210> SEQ ID NO 55
<211> LENGTH: 1857
<212> TYPE: DNA
<213> ORGANISM: Artificial Sequence
<220> FEATURE:
<223> OTHER INFORMATION: Mut-N37

<400> SEQUENCE: 55

```
atggacaaca acccaaacat caacgaatgc attccataca actgcttgag taacccagaa       60
gttgaagtac ttggtggaga acgcattgaa accggttaca ctcccatcga catctccttg      120
tccttgacac agtttctgct cagcgagttc gtgccaggag ctgggttcgt tctcggacta      180
gttgacatca tctggggtat cttttggtcca tctcaatggg atgcattcct ggtgcaaatt      240
gagcagttga tcaaccagag gatcgaagag ttcgccagga accaggccat ctctcgtttg      300
gaaggattga gcaatctcta ccaaatctat gcagagagct tcagagagtg ggaagccgat      360
cctactaacc cagctctccg cgtggaaatg cgtattcaat tcaacgacat gaacagcgcc      420
ttgaccacag ctatcccatt gttcgcagtc cagaactacc aagttcctct cttgtccgtg      480
tacgttcaag cagctaatct tcacctcagc gtgcttcgag acgttagcgt gtttgggcaa      540
agatggggat tcgatgctac caccatcaat agccgttaca acgaccttac taggctgatt      600
ggaaactaca ccgactacgc tgttcgttgg tacaacactg gcttggagcg tgtctggggt      660
cctgattcta gagattggat cagatacaac cagttcagga gagaattgac cctcacagtt      720
ttggacattg tgtctctctt cagcaactat gactccagac gttaccctat ccgtacagtg      780
tcccaactta ccagagaaat ctacactaac ccagttcttg agaacttcga cggtagcttc      840
cgtggtatgg cccagaggat cgaaagatcc atcaggagcc cacacttgat ggacatcttg      900
aacagcataa ctatctacac cgatgtgcac agaggatact attactggtc tggacaccag      960
```

```
atcaccgcct ctccagttgg attctccgga cctgagtttg cttttcctct ctatggaact   1020
atgggaaacg ccgctccaca acaacgtatc gttgctcaac taggacaggg tgtctacaga   1080
accttgtctt ccaccttgta cagaagaccc ttcaatatcg gtcctaacaa ccaggagctt   1140
ttcgttcttg acggaacaga gttcgcctat ggaacctctt ctaacttgcc atccgctgtt   1200
tacagaaaga gcggaaccgt tgattccttg gacgtgatcc caccacagga taacagcgtg   1260
ccacccaggg ctggattctc ccacaggctt agccacgtgt ccatgttccg ttccggattc   1320
agcaacagtt ccgtgagcat catcagagct cctatgttct cttggattca ccgttctgcc   1380
gagttcaaca acatcatcgc atctgatagt attactcaaa tccctgccgt gaagggaaac   1440
ttccttttca atggaagcgt tatcagcgga ccaggattca ctggcggaga tcttgtgaga   1500
cttaacagct ctggcaacaa cattcagaat agaggctaca tcgaagttcc tatccacttc   1560
ccatccacat ctactagata cagagttagg gttagatacg cctctgtgac cccaatccac   1620
cttaacgtga actggggcaa ttcatctatc ttctccaaca ccgttccagc tactgctacc   1680
tcactcgata atcttcaatc cagcgatttt ggttacttcg aaagtgccaa cgcattcact   1740
tcttcattgg gcaacatcgt gggtgttagg aatttcagcg gtactgcagg agtgatcatt   1800
gacagattcg agttcattcc tgttactgcc actcttgagg ctgagtacaa tcttttaa    1857
```

<210> SEQ ID NO 56  
<211> LENGTH: 1857  
<212> TYPE: DNA  
<213> ORGANISM: Artificial Sequence  
<220> FEATURE:  
<223> OTHER INFORMATION: Mut-N38

<400> SEQUENCE: 56

```
atggacaaca acccaaacat caacgaatgc attccataca actgcttgag taacccagaa    60
gttgaagtac ttggtggaga acgcattgaa accggttaca ctcccatcga catctccttg   120
tccttgacac agtttctgct cagcgagttc gtgccaggag ctgggttcgt tctcggacta   180
gttgacatca tctggggtat ctttggtcca tctcaatggg atgcattcct ggtgcaaatt   240
gagcagttga tcaaccagag gatcgaagag ttcgccagga accaggccat ctctcgtttg   300
gaaggattga gcaatctcta ccaaatctat gcagagagct tcagagcttg ggaagccgat   360
cctactaacc cagctctccg cgtggaaatg cgtattcaat tcaacgacat gaacagcgcc   420
ttgaccacag ctatcccatt gttcgcagtc cagaactacc aagttcctct cttgtccgtg   480
tacgttcaag cagctaatct tcacctcagc gtgcttcgag acgttagcgt gtttgggcaa   540
agatggggat cgatgctac caccatcaat agccgttaca acgacttac taggctgatt   600 ggaaactaca ccgactacgc tgttcgttgg tacaacactg gcttggagcg tgtctggggt   660
cctgattcta gagattggat cagatacaac cagttcagga gagaattgac cctcacagtt   720
ttggacattg tgtctctctt cagcaactat gactccagaa cctacccta ccgtacagtg   780 tcccaactta ccagagaaat ctacactaac ccagttcttg agaacttcga cggtagcttc   840
cgtggtatgg cccagaggat cgaaagatcc atcaggagcc acacttgat ggacatcttg   900 aacagcataa ctatctacac cgatgtgcac agaggatact attactggtc tggacaccag   960
atcaccgcct ctccagttgg attctccgga cctgagtttg cttttcctct ctatggaact  1020
atgggaaacg ccgctccaca acaacgtatc gttgctcaac taggacaggg tgtctacaga  1080
accttgtctt ccaccttgta cagaagaccc ttcaatatcg gtcctaacaa ccagcaactt  1140
```

-continued

| | |
|---|---|
| tccgttcttg acggaacaga gttcgcctat ggaacctctt ctaacttgcc atccgctgtt | 1200 |
| tacagaaaga gcggaaccgt tgattccttg gacgtgatcc caccacagga taacagcgtg | 1260 |
| ccacccaggg ctggattctc ccacaggctt agccacgtgt ccatgttccg ttccggattc | 1320 |
| agcaacagtt ccgtgagcat catcagagct cctatgttct cttggattca ccgttctgcc | 1380 |
| gagttcaaca acatcatcgc atctgatagt attactcaaa tccctgccgt gaagggaaac | 1440 |
| ttccttttca atgaagcgt tatcagcgga ccaggattca ctggcggaga tcttgtgaga | 1500 |
| cttaacagct ctggcaacaa cattcagaat agaggctaca tcgaagttcc tatccacttc | 1560 |
| ccatccacat ctactagata cagagttagg gttagatacg cctctgtgac cccaatccac | 1620 |
| cttaacgtga actggggcaa ttcatctatc ttctccaaca ccgttccagc tactgctacc | 1680 |
| tcactcgata tcttcaatc cagcgatttt ggttacttcg aaagtgccaa cgcattcact | 1740 |
| tcttcattgg gcaacatcgt gggtgttagg aatttcagcg gtactgcagg agtgatcatt | 1800 |
| gacagattcg agttcattcc tgttactgcc actcttgagg ctgagtacaa tctttaa | 1857 |

<210> SEQ ID NO 57
<211> LENGTH: 1857
<212> TYPE: DNA
<213> ORGANISM: Artificial Sequence
<220> FEATURE:
<223> OTHER INFORMATION: Mut-N39

<400> SEQUENCE: 57

| | |
|---|---|
| atggacaaca acccaaacat caacgaatgc attccataca actgcttgag taacccagaa | 60 |
| gttgaagtac ttggtggaga acgcattgaa accggttaca ctcccatcga catctccttg | 120 |
| tccttgacac agtttctgct cagcgagttc gtgccaggag ctgggttcgt tctcggacta | 180 |
| gttgacatca tctggggtat ctttggtcca tctcaatggg atgcattcct ggtgcaaatt | 240 |
| gagcagttga tcaaccagag gatcgaagag ttcgccagga accaggccat ctctcgtttg | 300 |
| gaaggattga gcaatctcta ccaaatctat gcagagagct tcagagagtg ggaagccgat | 360 |
| cctactaacc cagctctccg cgaggaaatg cgtattcaat tcaacgacat gaacagcgcc | 420 |
| ttgaccacag ctatcccatt gttcgcagtc cagaactacc aagttcctct cttgtccgtg | 480 |
| tacgttcaag cagctaatct tcacctcagc gtgcttcgag acgttagcgt gtttgggcaa | 540 |
| agatggggat cgatgctac caccatcaat agccgttaca cgaccttac taggctgatt | 600 |
| ggaaactaca ccgactacgc tgttcgttgg tacaacactg gcttggagcg tgtctggggt | 660 |
| cctgattcta gagattgggt gagatacaac cagttcagga gagaattgac cctcacagtt | 720 |
| ttggacattg tggctctctt cagcaactat gactccagac gttaccctat ccgtacagtg | 780 |
| tcccaactta ccagagaaat ctacactaac ccagttcttg agaacttcga cggtagcttc | 840 |
| cgtggtatgg cccagaggat cgaaagatcc atcaggagcc acacttgat ggacatcttg | 900 |
| aacagcataa ctatctacac cgatgtgcac agaggatact attactggtc tggacaccag | 960 |
| atcaccgcct ctccagttgg attctccgga cctgagtttg ctttcctct ctatggaact | 1020 |
| atgggaaacg ccgctccaca acaacgtatc gttgctcaac taggacaggg tgtctacaga | 1080 |
| accttgtctt ccaccttgta cagaagaccc ttcaatatcg gtcctaacaa ccagcaactt | 1140 |
| tccgttcttg acggaacaga gttcgcctat ggaacctctt ctaacttgcc atccgctgtt | 1200 |
| tacagaaaga gcggaaccgt tgattccttg gacgtgatcc caccacagga taacagcgtg | 1260 |
| ccacccaggg ctggattctc ccacaggctt agccacgtgt ccatgttccg ttccggattc | 1320 |
| agcaacagtt ccgtgagcat catcagagct cctatgttct cttggattca ccgttctgcc | 1380 |

```
gagttcaaca acatcatcgc atctgatagt attactcaaa tccctgccgt gaagggaaac    1440
ttccttttca atggaagcgt tatcagcgga ccaggattca ctggcggaga tcttgtgaga    1500
cttaacagct ctggcaacaa cattcagaat agaggctaca tcgaagttcc tatccacttc    1560
ccatccacat ctactagata cagagttagg gttagatacg cctctgtgac cccaatccac    1620
cttaacgtga actggggcaa ttcatctatc ttctccaaca ccgttccagc tactgctacc    1680
tcactcgata atcttcaatc cagcgatttt ggttacttcg aaagtgccaa cgcattcact    1740
tcttcattgg gcaacatcgt gggtgttagg aatttcagcg gtactgcagg agtgatcatt    1800
gacagattcg agttcattcc tgttactgcc actcttgagg ctgagtacaa tcttaa       1857
```

<210> SEQ ID NO 58
<211> LENGTH: 1857
<212> TYPE: DNA
<213> ORGANISM: Artificial Sequence
<220> FEATURE:
<223> OTHER INFORMATION: Mut-N40

<400> SEQUENCE: 58

```
atggacaaca acccaaacat caacgaatgc attccataca actgcttgag taacccagaa      60
gttgaagtac ttggtggaga acgcattgaa accggttaca ctcccatcga catctccttg     120
tccttgacac agtttctgct cagcgagttc gtgccaggag ctgggttcgt tctcggacta     180
gttgacatca tctggggtat ctttggtcca tctcaatggg atgcattcct ggtgcaaatt     240
gagcagttga tcaaccagag gatcgaagag ttcgccagga accaggccat ctctcgtttg     300
gaaggattga gcaatctcta ccaaatctat gcagagagct tcagagagtg ggaagccgat     360
cctactaacc cagctctccg cgaggaaatg cgtattcaat tcaacgacat gaacagcgcc     420
ttgaccacag ctatcccatt gttcgcagtc cagaactacc aagttcctct cttgtccgtg     480
tacgttcaag cagctaatct tcacctcagc gtgcttcgag acgttagcgt gtttgggcaa     540
agatggggat tcgatgctgc aaccatcaat agccgttaca acgaccttac taggctgatt     600
ggaaactaca ccgactacgc tgttcgttgg tacaacactg gcttggagcg tgtctggggt     660
cctgattcta gagattgggt gagatacaac cagttcagga gagaattgac cctcacagtt     720
ttggacattg tgtctctctt cagcaactat gactccagac gttaccctat ccgtacagtg     780
tcccaactta ccagagaaat ctacactaac ccagttcttg agaacttcga cggtagcttc     840
cgtggtatgg cccagaggat cgaaagatcc atcaggagcc acacttgat  ggacatcttg     900 aacagcataa ctatctacac cgatgtgcac agaggatact attactggtc tggacaccag     960
atcaccgcct ctccagttgg attctccgga cctgagtttg cttttcctct ctatggaact    1020
atgggaaacg ccgctccaca acaacgtatc gttgctcaac taggacaggg tgtctacaga    1080
accttgtctt ccaccttgta cagaagaccc ttcaatatcg gtcctaacaa ccaggagctt    1140
ttcgttcttg acggaacaga gttcgcctat ggaacctctt ctaacttgcc atccgctgtt    1200
tacagaaaga gcggaaccgt tgattccttg gacgtgatcc caccacagaa caacaatgtg    1260
ccacccaggg ctggattctc ccacaggctt agccacgtgt ccatgttccg ttccggattc    1320
agcaacagtt ccgtgagcat catcagagct cctatgttct cttggattca ccgttctgcc    1380
gagttcaaca acatcatcgc atctgatagt attactcaaa tccctgccgt gaagggaaac    1440
ttccttttca atggaagcgt tatcagcgga ccaggattca ctggcggaga tcttgtgaga    1500
cttaacagct ctggcaacaa cattcagaat agaggctaca tcgaagttcc tatccacttc    1560
```

```
ccatccacat ctactagata cagagttagg gttagatacg cctctgtgac cccaatccac    1620
cttaacgtga actggggcaa ttcatctatc ttctccaaca ccgttccagc tactgctacc    1680
tcactcgata atcttcaatc cagcgatttt ggttacttcg aaagtgccaa cgcattcact    1740
tcttcattgg gcaacatcgt gggtgttagg aatttcagcg gtactgcagg agtgatcatt    1800
gacagattcg agttcattcc tgttactgcc actcttgagg ctgagtacaa tctttaa      1857
```

<210> SEQ ID NO 59
<211> LENGTH: 1857
<212> TYPE: DNA
<213> ORGANISM: Artificial Sequence
<220> FEATURE:
<223> OTHER INFORMATION: Mut-N41

<400> SEQUENCE: 59

```
atggacaaca acccaaacat caacgaatgc attccataca actgcttgag taacccagaa     60
gttgaagtac ttggtggaga acgcattgaa accggttaca ctcccatcga catctccttg    120
tccttgacac agtttctgct cagcgagttc gtgccaggag ctgggttcgt tctcggacta    180
gttgacatca tctggggtat ctttggtcca tctcaatggg atgcattcct ggtgcaaatt    240
gagcagttga tcaaccagag gatcgaagag ttcgccagga accaggccat ctctcgtttg    300
gaaggattga gcaatctcta ccaaatctat gcagagagct tcagagcttg ggaagccgat    360
cctactaacc cagctctccg cgaggaaatg cgtattcaat tcaacgacat gaacagcgcc    420
ttgaccacag ctatcccatt gttcgcagtc cagaactacc aagttcctct cttgtccgtg    480
tacgttcaag cagctaatct tcacctcagc gtgcttcgag acgttagcgt gtttgggcaa    540
agatggggat cgatgctac caccatcaat agccgttaca acgacttac taggctgatt    600 ggaaactaca ccgactacgc tgttcgttgg tacaacactg gcttggagcg tgtctgggt    660 cctgattcta gagattgggt gagatacaac cagttcagga gagaattgac cctcacagtt    720
ttggacattg tgtctctctt cagcaactat gactccagac gttaccctat ccgtacagtg    780
tcccaactta ccagagaaat ctacactaac ccagttcttg agaacttcga cggtagcttc    840
cgtggtatgg cccagaggat cgaaagatcc atcaggagcc acacttgat ggacatcttg    900 aacagcataa ctatctacac cgatgtgcac agaggatact attactggtc tggacaccag    960
atcaccgcct ctccagttgg attctccgga cctgagtttg cttttcctct ctatggaact   1020
atgggaaacg ccgctccaca caacgtatc gttgctcaac taggacaggg tgtctacaga   1080
accttgtctt ccaccttgta cagaagaccc ttcaatatcg gtcctaacaa ccagcaactt   1140
tccgttcttg acggaacaga gttcgcctat ggaacctctt ctaacttgcc atccgctgtt   1200
tacagaaaga gcggaaccgt tgattccttg gacgtgatcc caccacagga taacagcgtg   1260
ccacccaggg ctggattctc ccacaggctt agccacgtgt ccatgttccg ttccggattc   1320
agcaacagtt ccgtgagcat catcagagct cctatgttct cttggattca ccgttctgcc   1380
gagttcaaca acatcatcgc atctgatagt attactcaaa tccctgccgt gaagggaaac   1440
ttccttttca atgaagcgt tatcagcgga ccaggattca ctggcggaga tcttgtgaga   1500
cttaacagct ctggcaacaa cattcagaat agaggctaca tcgaagttcc tatccacttc   1560
ccatccacat ctactagata cagagttagg gttagatacg cctctgtgac cccaatccac   1620
cttaacgtga actggggcaa ttcatctatc ttctccaaca ccgttccagc tactgctacc   1680
tcactcgata atcttcaatc cagcgatttt ggttacttcg aaagtgccaa cgcattcact   1740
tcttcattgg gcaacatcgt gggtgttagg aatttcagcg gtactgcagg agtgatcatt   1800
```

```
gacagattcg agttcattcc tgttactgcc actcttgagg ctgagtacaa tctttaa      1857
```

<210> SEQ ID NO 60
<211> LENGTH: 1857
<212> TYPE: DNA
<213> ORGANISM: Artificial Sequence
<220> FEATURE:
<223> OTHER INFORMATION: Mut-N44

<400> SEQUENCE: 60

```
atggacaaca acccaaacat caacgaatgc attccataca actgcttgag taacccagaa     60
gttgaagtac ttggtggaga acgcattgaa accggttaca ctcccatcga catctccttg    120
tccttgacac agtttctgct cagcgagttc gtgccaggag ctgggttcgt tctcggacta    180
gttgacatca tctggggtat ctttggtcca tctcaatggg atgcattcct ggtgcaaatt    240
gagcagttga tcaaccagag gatcgaagag ttcgccagga accaggccat ctctcgtttg    300
gaaggattga gcaatctcta ccaaatctat gcagagagct tcagagcttg ggaagccgat    360
cctactaacc cagctctccg cgaggaaatg cgtattcaat tcaacgacat gaacagcgcc    420
ttgaccacag ctatcccatt gttcgcagtc cagaactacc aagttcctct cttgtccgtg    480
tacgttcaag cagctaatct tcacctcagc gtgcttcgag acgttagcgt gtttgggcaa    540
agatgggaat tcgatgctac caccatcaat agccgttaca acgacttac taggctgatt     600
ggaaactaca ccgactacgc tgttcgttgg tacaacactg gcttggagcg tgtctggggt    660
cctgattcta gagattgggt gagatacaac cagttcagga gagaattgac cctcacagtt    720
ttggacattg tgtctctctt cagcaactat gactccagac gttaccctat ccgtacagtg    780
tcccaactta ccagagaaat ctacactaac ccagttcttg agaacttcga cggtagcttc    840
cgtggtatgg cccagaggat cgaaagatcc atcaggagcc acacttgat ggacatcttg      900
aacagcataa ctatctacac cgatgtgcac agaggatact attactggtc tggacaccag    960
atcaccgcct ctccagttgg attctccgga cctgagtttg cttttcctct ctatggaact   1020
atgggaaacg ccgctccaca acaacgtatc gttgctcaac taggacaggg tgtctacaga   1080
accttgtctt ccaccttgta cagaagaccc ttcaatatcg gtcctaacaa ccagcaactt   1140
tccgttcttg acggaacaga gttcgcctat ggaacctctt ctaacttgcc atccgctgtt   1200
tacagaaaga gcgaaccgt tgattccttg acgtgatcc caccacagga taacagcgtg      1260
ccacccaggg ctggattctc ccacaggctt agccacgtgt ccatgttccg ttccggattc   1320
agcaacagtt ccgtgagcat catcagagct cctatgttct cttggattca ccgttctgcc   1380
gagttcaaca acatcatcgc atctgatagt attactcaaa tccctgccgt gaagggaaac   1440
ttccttttca atgaagcgt tatcagcgga ccaggattca ctggcggaga tcttgtgaga    1500
cttaacagct ctggcaacaa cattcagaat agaggctaca tcgaagttcc tatccacttc   1560
ccatccacat ctactagata cagagttagg gttagatacg cctctgtgac cccaatccac   1620
cttaacgtga actggggcaa ttcatctatc ttctccaaca ccgttccagc tactgctacc   1680
tcactcgata tcttcaatc cagcgatttt ggttacttcg aaagtgccaa cgcattcact    1740
tcttcattgg gcaacatcgt gggtgttagg aatttcagcg gtactgcagg agtgatcatt   1800
gacagattcg agttcattcc tgttactgcc actcttgagg ctgagtacaa tctttaa      1857
```

<210> SEQ ID NO 61
<211> LENGTH: 1857
<212> TYPE: DNA

<213> ORGANISM: Artificial Sequence
<220> FEATURE:
<223> OTHER INFORMATION: Mut-N51

<400> SEQUENCE: 61

```
atggacaaca acccaaacat caacgaatgc attccataca actgcttgag taacccagaa        60
gttgaagtac ttggtggaga acgcattgaa accggttaca ctcccatcga catctccttg       120
tccttgacac agtttctgct cagcgagttc gtgccaggag ctgggttcgt tctcggacta       180
gttgacatca tctggggtat ctttggtcca tctcaatggg atgcattcct ggtgcaaatt       240
gagcagttga tcaaccagag gatcgaagag ttcgccagga accaggccat ctctcgtttg       300
gaaggattga gcaatctcta ccaaatctat gcagagagct tcagagcttg ggaagccgat       360
cctactaacc cagctctccg cgtggaaatg cgtattcaat tcaacgacat gaacagcgcc       420
ttgaccacag ctatcccatt gttcgcagtc cagaactacc aagttcctct cttgtccgtg       480
tacgttcaag cagctaatct tcacctcagc gtgcttcgag cgttagcgt gtttgggcaa        540
agatggggat tcgatgctac caccatcaat agccgttaca acgaccttac taggctgatt       600
ggaaactaca ccgactacgc tgttcgttgg tacaacactg gcttggagcg tgtctggggt       660
cctgattcta gagattggat cagatacaac cagttcagga gagaattgac cctcacagtt       720
ttggacattg tgtctctctt cccgaactat gactccagaa cctaccctat ccgtacagtg       780
tcccaactta ccagagaaat ctacactaac ccagttcttg agaacttcga cggtagcttc       840
cgtggttctg cccagggtat cgaaagatcc atcaggagcc acacttgat ggacatcttg        900
aacagcataa ctatctacac cgatgtgcac agaggatact attactggtc tggacaccag       960
atcaccgcct ctccagttgg attctccgga cctgagttta cctttcctct ctatggaact      1020
atgggaaacg ccgctccaca caacgtatc gttgctcaac taggacaggg tgtctacaga       1080
accttgtctt ccaccttgta cagaagaccc ttcaatatcg gtatcaacaa ccagcaactt      1140
tccgttcttg acgaacaga gttcgcctat ggaacctctt ctaacttgcc atccgctgtt       1200
tacagaaaga gcggaaccgt tgattccttg gacgtgatcc caccacagaa caacaatgtg      1260
ccacccaggg ctggattctc ccacaggctt agccacgtgt ccatgttccg ttccggattc      1320
agcaacagtt ccgtgagcat catcagagct cctatgttct cttggattca ccgttctgcc      1380
gagttcaaca acatcatcgc atctgatagt attactcaaa tccctgccgt gaagggaaac      1440
ttcctttca atggaagcgt tatcagcgga ccaggattca ctggcggaga tcttgtgaga       1500
cttaacagct ctggcaacaa cattcagaat agaggctaca tcgaagttcc tatccacttc      1560
ccatccacat ctactagata cagagttagg gttagatacg cctctgtgac cccaatccac      1620
cttaacgtga actggggcaa ttcatctatc ttctccaaca ccgttccagc tactgctacc      1680
tcactcgata atcttcaatc cagcgatttt ggttacttcg aaagtgccaa cgcattcact      1740
tcttcattgg gcaacatcgt gggtgttagg aatttcagcg gtactgcagg agtgatcatt      1800
gacagattcg agttcattcc tgttactgcc actcttgagg ctgagtacaa tctttaa        1857
```

<210> SEQ ID NO 62
<211> LENGTH: 1857
<212> TYPE: DNA
<213> ORGANISM: Artificial Sequence
<220> FEATURE:
<223> OTHER INFORMATION: Mut-N52

<400> SEQUENCE: 62

```
atggacaaca acccaaacat caacgaatgc attccataca actgcttgag taacccagaa        60
```

```
gttgaagtac ttggtggaga acgcattgaa accggttaca ctcccatcga catctccttg     120
tccttgacac agtttctgct cagcgagttc gtgccaggag ctgggttcgt tctcggacta     180
gttgacatca tctggggtat cttggtcca tctcaatggg atgcattcct ggtgcaaatt      240
gagcagttga tcaaccagag gatcgaagag ttcgccagga accaggccat ctctcgtttg     300
gaaggattga gcaatctcta ccaaatctat gcagagagct tcagagcttg ggaagccgat     360
cctactaacc cagctctccg cgtggaaatg cgtattcaat tcaacgacat gaacagcgcc     420
ttgaccacag ctatcccatt gttcgcagtc cagaactacc aagttcctct cttgtccgtg     480
tacgttcaag cagctaatct tcacctcagc gtgcttcgag acgttagcgt gtttgggcaa     540
agatggggat tcgatgctac caccatcaat agccgttaca acgacttac taggctgatt      600 ggaaactaca ccgactacgc tgttcgttgg tacaacactg gcttggagcg tgtctgggt     660 cctgattcta gagattggat cagatacaac cagttcagga gagaattgac cctcacagtt     720
ttggacattg tgtctctctt cccgaactat gactccagaa cctaccctat ccgtacagtg     780
tcccaactta ccagagaaat ctacactaac ccagttcttg agaacttcga cggtagcttc     840
cgtggtatgg cccagggtat cgaaagatcc atcaggagcc acacttgat ggacatcttg       900 aacagcataa ctatctacac cgatgtgcac agaggatact attactggtc tggacaccag     960
atcaccgcct ctccagttgg attctccgga cctgagtttta cctttcctct ctatggaact    1020
atgggaaacg ccgctccaca acaacgtatc gttgctcaac taggacaggg tgtctacaga     1080
accttgtctt ccaccttgta cagaagaccc ttcaatatcg gtattaacaa ccagcaactt     1140
tccgttcttg acggaacaga gttcgcctat ggaacctctt ctaacttgcc atccgctgtt     1200
tacagaaaga gcggaaccgt tgattccttg gacgtgatcc caccacagaa caacaatgtg     1260
ccacccaggg ctgattctc ccacaggctt agccacgtgt ccatgttccg ttccggattc       1320
agcaacagtt ccgtgagcat catcagagct cctatgttct cttggattca ccgttctgcc     1380
gagttcaaca acatcatcgc atctgatagt attactcaaa tccctgccgt gaaggaaac     1440 ttccttttca atgaagcgt tatcagcgga ccaggattca ctggcggaga tcttgtgaga      1500
cttaacagct ctggcaacaa cattcagaat agaggctaca tcgaagttcc tatccacttc     1560
ccatccacat ctactagata cagagttagg gttagatacg cctctgtgac cccaatccac     1620
cttaacgtga actgggcaa ttcatctatc ttctccaaca ccgttccagc tactgctacc       1680
tcactcgata tcttcaatc cagcgatttt ggttacttcg aaagtgccaa cgcattcact      1740
tcttcattgg gcaacatcgt gggtgttagg aatttcagcg gtactgcagg agtgatcatt     1800
gacagattcg agttcattcc tgttactgcc actcttgagg ctgagtacaa tctttaa        1857
```

<210> SEQ ID NO 63
<211> LENGTH: 1857
<212> TYPE: DNA
<213> ORGANISM: Artificial Sequence
<220> FEATURE:
<223> OTHER INFORMATION: Mut-N54

<400> SEQUENCE: 63

```
atggacaaca acccaaacat caacgaatgc attccataca actgcttgag taacccagaa      60
gttgaagtac ttggtggaga acgcattgaa accggttaca ctcccatcga catctccttg     120
tccttgacac agtttctgct cagcgagttc gtgccaggag ctgggttcgt tctcggacta     180
gttgacatca tctggggtat cttggtcca tctcaatggg atgcattcct ggtgcaaatt      240
```

| | |
|---|---|
| gagcagttga tcaaccagag atcgaagag ttcgccagga accaggccat ctctcgtttg | 300 |
| gaaggattga gcaatctcta ccaaatctat gcagagagct tcagagcttg ggaagccgat | 360 |
| cctactaacc cagctctccg cgtggaaatg cgtattcaat tcaacgacat gaacagcgcc | 420 |
| ttgaccacag ctatcccatt gttcgcagtc cagaactacc aagttcctct cttgtccgtg | 480 |
| tacgttcaag cagctaatct tcacctcagc gtgcttcgag acgttagcgt gtttgggcaa | 540 |
| agatggggat tcgatgctac caccatcaat agccgttaca acgacttac taggctgatt | 600 |
| ggaaactaca ccgactacgc tgttcgttgg tacaacactg gcttggagcg tgtctggggt | 660 |
| cctgattcta gagattggat cagatacaac cagttcagga gagaattgac cctcacagtt | 720 |
| ttggacattg tgtctctctt cccgaactat gactccagaa cctaccctat ccgtacagtg | 780 |
| tcccaactta ccagagaaat ctacactaac ccagttcttg agaacttcga cggtagcttc | 840 |
| cgtggttctg cccagggtat cgaaagatcc atcaggagcc acacttgat ggacatcttg | 900 |
| aacagcataa ctatctacac cgatgtgcac agaggatact attactgtc tggacaccag | 960 |
| atcaccgcct ctccagttgg attctccgga cctgagtttg cttttcctct ctatggaact | 1020 |
| atgggaaacg ccgctccaca acaacgtatc gttgctcaac taggacaggg tgtctacaga | 1080 |
| accttgtctt ccaccttgta cagaagaccc ttcaatatcg gtatcaacaa ccagcaactt | 1140 |
| tccgttcttg acggaacaga gttcgcctat ggaacctctt ctaacttgcc atccgctgtt | 1200 |
| tacagaaaga gcgaaccgt tgattccttg gacgtgatcc caccacagaa caacaatgtg | 1260 |
| ccacccaggg ctggattctc ccacaggctt agccacgtgt ccatgttccg ttccggattc | 1320 |
| agcaacagtt ccgtgagcat catcagagct cctatgttct cttggattca ccgttctgcc | 1380 |
| gagttcaaca acatcatcgc atctgatagt attactcaaa tccctgccgt gaagggaaac | 1440 |
| ttccttttca tggaagcgt tatcagcgga ccaggattca ctggcggaga tcttgtgaga | 1500 |
| cttaacagct ctggcaacaa cattcagaat agaggctaca tcgaagttcc tatccacttc | 1560 |
| ccatccacat ctactagata cagagttagg gttagatacg cctctgtgac cccaatccac | 1620 |
| cttaacgtga actggggcaa ttcatctatc ttctccaaca ccgttccagc tactgctacc | 1680 |
| tcactcgata atcttcaatc cagcgatttt ggttacttcg aaagtgccaa cgcattcact | 1740 |
| tcttcattgg gcaacatcgt gggtgttagg aatttcagcg gtactgcagg agtgatcatt | 1800 |
| gacagattcg agttcattcc tgttactgcc actcttgagg ctgagtacaa tctttaa | 1857 |

<210> SEQ ID NO 64
<211> LENGTH: 1857
<212> TYPE: DNA
<213> ORGANISM: Artificial Sequence
<220> FEATURE:
<223> OTHER INFORMATION: Mut-N55

<400> SEQUENCE: 64

| | |
|---|---|
| atggacaaca acccaaacat caacgaatgc attccataca actgcttgag taacccagaa | 60 |
| gttgaagtac ttggtggaga acgcattgaa accggttaca ctcccatcga catctccttg | 120 |
| tccttgacac agtttctgct cagcgagttc gtgccaggag ctgggttcgt tctcggacta | 180 |
| gttgacatca tctgggtat cttggtcca tctcaatggg atgcattcct ggtgcaaatt | 240 |
| gagcagttga tcaaccagag atcgaagag ttcgccagga accaggccat ctctcgtttg | 300 |
| gaaggattga gcaatctcta ccaaatctat gcagagagct tcagagcttg ggaagccgat | 360 |
| cctactaacc cagctctccg cgtggaaatg cgtattcaat tcaacgacat gaacagcgcc | 420 |
| ttgaccacag ctatcccatt gttcgcagtc cagaactacc aagttcctct cttgtccgtg | 480 |

```
tacgttcaag cagctaatct tcacctcagc gtgcttcgag acgttagcgt gtttgggcaa    540
agatggggat tcgatgctac caccatcaat agccgttaca acgacttac taggctgatt    600 ggaaactaca ccgactacgc tgttcgttgg tacaacactg gcttggagcg tgtctggggt    660
cctgattcta gagattggat cagatacaac cagttcagga gagaattgac cctcacagtt    720
ttggacattg tgtctctctt cccgaactat gactccagaa cctaccctat ccgtacagtg    780
tcccaactta ccagagaaat ctacactaac ccagttcttg agaacttcga cggtagcttc    840
cgtggttctg cccagggtat cgaaagatcc atcaggagcc cacacttgat ggacatcttg    900
aacagcataa ctatctacac cgatgtgcac agaggatact attactggtc tggacaccag    960
atcaccgcct ctccagttgg attctccgga cctgagttta cctttcctct ctatggaact   1020
atgggaaacg ccgctccaca acaacgtatc gttgctcaac taggacaggg tgtctacaga   1080
accttgtctt ccaccttgta cagaagaccc ttcaatatcg gtcctaacaa ccagcaactt   1140
tccgttcttg acggaacaga gttcgcctat ggaacctctt ctaacttgcc atccgctgtt   1200
tacagaaaga gcggaaccgt tgattccttg gacgtgatcc caccacagaa caacaatgtg   1260
ccacccaggg ctggattctc ccacaggctt agccacgtgt ccatgttccg ttccggattc   1320
agcaacagtt ccgtgagcat catcagagct cctatgttct cttggattca ccgttctgcc   1380
gagttcaaca acatcatcgc atctgatagt attactcaaa tccctgccgt gaagggaaac   1440 ttcctttttca atgaagcgt tatcagcgga ccaggattca ctggcggaga tcttgtgaga   1500
cttaacagct ctggcaacaa cattcagaat agaggctaca tcgaagttcc tatccacttc   1560
ccatccacat ctactagata cagagttagg gttagatacg cctctgtgac cccaatccac   1620
cttaacgtga actggggcaa ttcatctatc ttctccaaca ccgttccagc tactgctacc   1680
tcactcgata atcttcaatc cagcgatttt ggttacttcg aaagtgccaa cgcattcact   1740
tcttcattgg gcaacatcgt gggtgttagg aatttcagcg gtactgcagg agtgatcatt   1800
gacagattcg agttcattcc tgttactgcc actcttgagg ctgagtacaa tctttaa     1857
```

<210> SEQ ID NO 65
<211> LENGTH: 1857
<212> TYPE: DNA
<213> ORGANISM: Artificial Sequence
<220> FEATURE:
<223> OTHER INFORMATION: Mut-N57

<400> SEQUENCE: 65

```
atggacaaca acccaaacat caacgaatgc attccataca actgcttgag taacccagaa     60
gttgaagtac ttggtggaga acgcattgaa accggttaca ctcccatcga catctccttg    120
tccttgacac agtttctgct cagcgagttc gtgccaggag ctgggttcgt tctcggacta    180
gttgacatca tctggggtat ctttggtcca tctcaatggg atgcattcct ggtgcaaatt    240
gagcagttga tcaaccagag gatcgaagag ttcgccagga accaggccat ctctcgtttg    300
gaaggattga gcaatctcta ccaaatctat gcagagagct tcagagcttg ggaagccgat    360
cctactaacc cagctctccg cgtggaaatg cgtattcaat tcaacgacat gaacagcgcc    420
ttgaccacag ctatcccatt gttcgcagtc cagaactacc aagttcctct cttgtccgtg    480
tacgttcaag cagctaatct tcacctcagc gtgcttcgag acgttagcgt gtttgggcaa    540
agatggggat tcgatgctac caccatcaat agccgttaca acgacttac taggctgatt    600 ggaaactaca ccgactacgc tgttcgttgg tacaacactg gcttggagcg tgtctggggt    660
```

| | |
|---|---|
| cctgattcta gagattggat cagatacaac cagttcagga gagaattgac cctcacagtt | 720 |
| ttggacattg tgtctctctt cccgaactat gactccagaa cctaccctat ccgtacagtg | 780 |
| tcccaactta ccagagaaat ctacactaac ccagttcttg agaacttcga cggtagcttc | 840 |
| cgtggtatgg cccagggtat cgaaagatcc atcaggagcc cacacttgat ggacatcttg | 900 |
| aacagcataa ctatctacac cgatgtgcac agaggatact attactggtc tggacaccag | 960 |
| atcaccgcct ctccagttgg attctccgga cctgagtttg cttttcctct ctatggaact | 1020 |
| atgggaaacg ccgctccaca caacgtatcg gttgctcaac taggacaggg tgtctacaga | 1080 |
| accttgtctt ccaccttgta cagaagaccc ttcaatatcg gtatcaacaa ccagcaactt | 1140 |
| tccgttcttg acggaacaga gttcgcctat ggaacctctt ctaacttgcc atccgctgtt | 1200 |
| tacagaaaga gcggaaccgt tgattccttg acgtgatcc caccacagaa caacaatgtg | 1260 |
| ccacccaggg ctggattctc ccacaggctt agccacgtgt ccatgttccg ttccggattc | 1320 |
| agcaacagtt ccgtgagcat catcagagct cctatgttct cttggattca ccgttctgcc | 1380 |
| gagttcaaca acatcatcgc atctgatagt attactcaaa tccctgccgt gaagggaaac | 1440 |
| ttccttttca tggaagcgt tatcagcgga ccaggattca ctggcggaga tcttgtgaga | 1500 |
| cttaacagct ctggcaacaa cattcagaat agaggctaca tcgaagttcc tatccacttc | 1560 |
| ccatccacat ctactagata cagagttagg gttagatacg cctctgtgac cccaatccac | 1620 |
| cttaacgtga actggggcaa ttcatctatc ttctccaaca ccgttccagc tactgctacc | 1680 |
| tcactcgata atcttcaatc cagcgatttt ggttacttcg aaagtgccaa cgcattcact | 1740 |
| tcttcattgg gcaacatcgt gggtgttagg aatttcagcg gtactgcagg agtgatcatt | 1800 |
| gacagattcg agttcattcc tgttactgcc actcttgagg ctgagtacaa tctttaa | 1857 |

<210> SEQ ID NO 66
<211> LENGTH: 1857
<212> TYPE: DNA
<213> ORGANISM: Artificial Sequence
<220> FEATURE:
<223> OTHER INFORMATION: Mut-N58

<400> SEQUENCE: 66

| | |
|---|---|
| atggacaaca acccaaacat caacgaatgc attccataca actgcttgag taacccagaa | 60 |
| gttgaagtac ttggtggaga acgcattgaa accggttaca ctcccatcga catctccttg | 120 |
| tccttgacac agtttctgct cagcgagttc gtgccaggag ctgggttcgt tctcggacta | 180 |
| gttgacatca tctctggggtat cttt ggtcca tctcaatggg atgcattcct ggtgcaaatt | 240 |
| gagcagttga tcaaccagag gatcgaagag ttcgccagga accaggccat ctctcgtttg | 300 |
| gaaggattga gcaatctcta ccaaatctat gcagagagct tcagagcttg gaagccgat | 360 |
| cctactaacc cagctctccg cgtggaaatg cgtattcaat tcaacgacat gaacagcgcc | 420 |
| ttgaccacag ctatcccatt gttcgcagtc cagaactacc aagttcctct cttgtccgtg | 480 |
| tacgttcaag cagctaatct tcacctcagc gtgcttcgag acgttagcgt gtttgggcaa | 540 |
| agatggggat cgatgctac caccatcaat agccgttaca cgacccttac taggctgatt | 600 |
| ggaaactaca ccgactacgc tgttcgttgg tacaacactg gcttggagcg tgtctggggt | 660 |
| cctgattcta gagattggat cagatacaac cagttcagga gagaattgac cctcacagtt | 720 |
| ttggacattg tgtctctctt cccgaactat gactccagaa cctaccctat ccgtacagtg | 780 |
| tcccaactta ccagagaaat ctacactaac ccagttcttg agaacttcga cggtagcttc | 840 |
| cgtggtatgg cccagggtat cgaaagatcc atcaggagcc cacacttgat ggacatcttg | 900 |

| | |
|---|---|
| aacagcataa ctatctacac cgatgtgcac agaggatact attactggtc tggacaccag | 960 |
| atcaccgcct ctccagttgg attctccgga cctgagttta cctttcctct ctatggaact | 1020 |
| atgggaaacg ccgctccaca acaacgtatc gttgctcaac taggacaggg tgtctacaga | 1080 |
| accttgtctt ccaccttgta cagaagaccc ttcaatatcg gtcctaacaa ccagcaactt | 1140 |
| tccgttcttg acggaacaga gttcgcctat ggaacctctt ctaacttgcc atccgctgtt | 1200 |
| tacagaaaga gcggaaccgt tgattccttg acgtgatcc caccacagaa caacaatgtg | 1260 |
| ccacccaggg ctggattctc ccacaggctt agccacgtgt ccatgttccg ttccggattc | 1320 |
| agcaacagtt ccgtgagcat catcagagct cctatgttct cttggattca ccgttctgcc | 1380 |
| gagttcaaca acatcatcgc atctgatagt attactcaaa tccctgccgt gaagggaaac | 1440 |
| ttccttttca tggaagcgt tatcagcgga ccaggattca ctggcggaga tcttgtgaga | 1500 |
| cttaacagct ctggcaacaa cattcagaat agaggctaca tcgaagttcc tatccacttc | 1560 |
| ccatccacat ctactagata cagagttagg gttagatacg cctctgtgac cccaatccac | 1620 |
| cttaacgtga actggggcaa ttcatctatc ttctccaaca ccgttccagc tactgctacc | 1680 |
| tcactcgata tcttcaatc cagcgatttt ggttacttcg aaagtgccaa cgcattcact | 1740 |
| tcttcattgg gcaacatcgt gggtgttagg aatttcagcg gtactgcagg agtgatcatt | 1800 |
| gacagattcg agttcattcc tgttactgcc actcttgagg ctgagtacaa tctttaa | 1857 |

<210> SEQ ID NO 67
<211> LENGTH: 1857
<212> TYPE: DNA
<213> ORGANISM: Artificial Sequence
<220> FEATURE:
<223> OTHER INFORMATION: Mut-N61

<400> SEQUENCE: 67

| | |
|---|---|
| atggacaaca acccaaacat caacgaatgc attccataca actgcttgag taacccagaa | 60 |
| gttgaagtac ttggtggaga acgcattgaa accggttaca ctcccatcga catctccttg | 120 |
| tccttgacac agtttctgct cagcgagttc gtgccaggag ctgggttcgt tctcggacta | 180 |
| gttgacatca tctggggtat cttttggtcca tctcaatggg atgcattcct ggtgcaaatt | 240 |
| gagcagttga tcaaccagag gatcgaagag ttcgccagga accaggccat ctctcgtttg | 300 |
| gaaggattga gcaatctcta ccaaatctat gcagagagct tcagagcttg ggaagccgat | 360 |
| cctactaacc cagctctccg cgtggaaatg cgtattcaat tcaacgacat gaacagcgcc | 420 |
| ttgaccacag ctatcccatt gttcgcagtc cagaactacc aagttcctct cttgtccgtg | 480 |
| tacgttcaag cagctaatct tcacctcagc gtgcttcgag acgttagcgt gtttgggcaa | 540 |
| agatggggat cgatgctac caccatcaat agccgttaca acgaccttac taggctgatt | 600 |
| ggaaactaca ccgactacgc tgttcgttgg tacaacactg gcttggagcg tgtctggggt | 660 |
| cctgattcta gagattggat cagatacaac cagttcagga gagaattgac cctcacagtt | 720 |
| ttggacattg tgtctctctt cccgaactat gactccagaa cctaccctat ccgtacagtg | 780 |
| tcccaactta ccagagaaat ctacactaac ccagttcttg agaacttcga cggtagcttc | 840 |
| cgtggttctg cccagaggat cgaaagatcc atcaggagcc acacttgat ggacatcttg | 900 |
| aacagcataa ctatctacac cgatgtgcac agaggatact attactggtc tggacaccag | 960 |
| atcaccgcct ctccagttgg attctccgga cctgagttta cctttcctct ctatggaact | 1020 |
| atgggaaacg ccgctccaca acaacgtatc gttgctcaac taggacaggg tgtctacaga | 1080 |

| | | |
|---|---|---|
| accttgtctt ccaccttgta cagaagaccc ttcaatatcg gtcctaacaa ccagcaactt | 1140 | |
| tccgttcttg acggaacaga gttcgcctat ggaacctctt ctaacttgcc atccgctgtt | 1200 | |
| tacagaaaga gcggaaccgt tgattccttg acgtgatcc caccacagaa caacaatgtg | 1260 | |
| ccacccaggg ctggattctc ccacaggctt agccacgtgt ccatgttccg ttccggattc | 1320 | |
| agcaacagtt ccgtgagcat catcagagct cctatgttct cttggattca ccgttctgcc | 1380 | |
| gagttcaaca acatcatcgc atctgatagt attactcaaa tccctgccgt gaagggaaac | 1440 | |
| ttccttttca atggaagcgt tatcagcgga ccaggattca ctggcggaga tcttgtgaga | 1500 | |
| cttaacagct ctggcaacaa cattcagaat agaggctaca tcgaagttcc tatccacttc | 1560 | |
| ccatccacat ctactagata cagagttagg gttagatacg cctctgtgac cccaatccac | 1620 | |
| cttaacgtga actggggcaa ttcatctatc ttctccaaca ccgttccagc tactgctacc | 1680 | |
| tcactcgata atcttcaatc cagcgatttt ggttacttcg aaagtgccaa cgcattcact | 1740 | |
| tcttcattgg gcaacatcgt gggtgttagg aatttcagcg gtactgcagg agtgatcatt | 1800 | |
| gacagattcg agttcattcc tgttactgcc actcttgagg ctgagtacaa tctttaa | 1857 | |

<210> SEQ ID NO 68
<211> LENGTH: 1857
<212> TYPE: DNA
<213> ORGANISM: Artificial Sequence
<220> FEATURE:
<223> OTHER INFORMATION: Mut-N64

<400> SEQUENCE: 68

| | | |
|---|---|---|
| atggacaaca acccaaacat caacgaatgc attccataca actgcttgag taacccagaa | 60 | |
| gttgaagtac ttggtggaga acgcattgaa accggttaca ctcccatcga catctccttg | 120 | |
| tccttgacac agtttctgct cagcgagttc gtgccaggag ctgggttcgt tctcggacta | 180 | |
| gttgacatca tctggggtat ctttggtcca tctcaatggg atgcattcct ggtgcaaatt | 240 | |
| gagcagttga tcaaccagag gatcgaagag ttcgccagga accaggccat ctctcgtttg | 300 | |
| gaaggattga gcaatctcta ccaaatctat gcagagagct tcagagcttg ggaagccgat | 360 | |
| cctactaacc cagctctccg cgtggaaatg cgtattcaat tcaacgacat gaacagcgcc | 420 | |
| ttgaccacag ctatcccatt gttcgcagtc cagaactacc aagttcctct cttgtccgtg | 480 | |
| tacgttcaag cagctaatct tcacctcagc gtgcttcgag acgttagcgt gtttgggcaa | 540 | |
| agatggggat tcgatgctac caccatcaat agccgttaca acgaccttac taggctgatt | 600 | |
| ggaaactaca ccgactacgc tgttcgttgg tacaacactg gcttggagcg tgtctggggt | 660 | |
| cctgattcta gagattggat cagatacaac cagttcagga gagaattgac cctcacagtt | 720 | |
| ttggacattg tgtctctctt cccgaactat gactccagaa cctacccat ccgtacagtg | 780 | |
| tcccaactta ccagagaaat ctacactaac ccagttcttg agaacttcga cggtagcttc | 840 | |
| cgtggttctg cccagggtat cgaaagatcc atcaggagcc acacttgat ggacatcttg | 900 | |
| aacagcataa ctatctacac cgatgtgcac agaggatact attactggtc tggacaccag | 960 | |
| atcaccgcct ctccagttgg attctccgga cctgagtttg ctttccctct ctatggaact | 1020 | |
| atgggaaacg ccgctccaca acaacgtatc gttgctcaac taggacaggg tgtctacaga | 1080 | |
| accttgtctt ccaccttgta cagaagaccc ttcaatatcg gtcctaacaa ccagcaactt | 1140 | |
| tccgttcttg acggaacaga gttcgcctat ggaacctctt ctaacttgcc atccgctgtt | 1200 | |
| tacagaaaga gcggaaccgt tgattccttg acgtgatcc caccacagaa caacaatgtg | 1260 | |
| ccacccaggg ctggattctc ccacaggctt agccacgtgt ccatgttccg ttccggattc | 1320 | |

```
agcaacagtt ccgtgagcat catcagagct cctatgttct cttggattca ccgttctgcc   1380
gagttcaaca acatcatcgc atctgatagt attactcaaa tccctgccgt gaagggaaac   1440
ttccttttca atggaagcgt tatcagcgga ccaggattca ctggcggaga tcttgtgaga   1500
cttaacagct ctggcaacaa cattcagaat agaggctaca tcgaagttcc tatccacttc   1560
ccatccacat ctactagata cagagttagg gttagatacg cctctgtgac cccaatccac   1620
cttaacgtga actggggcaa ttcatctatc ttctccaaca ccgttccagc tactgctacc   1680
tcactcgata atcttcaatc cagcgatttt ggttacttcg aaagtgccaa cgcattcact   1740
tcttcattgg caacatcgt gggtgttagg aatttcagcg gtactgcagg agtgatcatt   1800
gacagattcg agttcattcc tgttactgcc actcttgagg ctgagtacaa tctttaa     1857
```

<210> SEQ ID NO 69
<211> LENGTH: 1857
<212> TYPE: DNA
<213> ORGANISM: Artificial Sequence
<220> FEATURE:
<223> OTHER INFORMATION: Mut-N68

<400> SEQUENCE: 69

```
atggacaaca acccaaacat caacgaatgc attccataca actgcttgag taacccagaa     60
gttgaagtac ttggtggaga acgcattgaa accggttaca ctcccatcga catctccttg    120
tccttgacac agtttctgct cagcgagttc gtgccaggag ctgggttcgt tctcggacta    180
gttgacatca tctggggtat ctttggtcca tctcaatggg atgcattcct ggtgcaaatt    240
gagcagttga tcaaccagag gatcgaagag ttcgccagga accaggccat ctctcgtttg    300
gaaggattga gcaatctcta ccaaatctat gcagagagct tcagagcttg ggaagccgat    360
cctactaacc cagctctccg cgtggaaatg cgtattcaat caacgacat gaacagcgcc     420 ttgaccacag ctatcccatt gttcgcagtc cagaactacc aagttcctct cttgtccgtg    480
tacgttcaag cagctaatct tcacctcagc gtgcttcgag acgttagcgt gtttgggcaa    540
agatggggat tcgatgctac caccatcaat agccgttaca acgacttac taggctgatt     600 ggaaactaca ccgactacgc tgttcgttgg tacaacactg gcttggagcg tgtctggggt    660
cctgattcta gagattggat cagatacaac cagttcagga gagaattgac cctcacagtt    720
ttggacattg tgtctctctt cccgaactat gactccagaa cctacccat ccgtacagtg     780 tcccaactta ccagagaaat ctacactaac ccagttcttg agaacttcga cggtagcttc    840
cgtggtatgg cccagaggat cgaaagatcc atcaggagcc acacttgat ggacatcttg      900 aacagcataa ctatctacac cgatgtgcac agaggatact attactggtc tggacaccag    960
atcaccgcct ctccagttgg attctccgga cctgagtttg cttttcctct ctatggaact   1020
atgggaaacg ccgctccaca acacgtatc gttgctcaac taggacaggg tgtctacaga    1080
accttgtctt ccaccttgta cagaagaccc ttcaatatcg gtcctaacaa ccagcaactt   1140
tccgttcttg acggaacaga gttcgcctat ggaacctctt ctaacttgcc atccgctgtt   1200
tacagaaaga gcggaaccgt tgattccttg acgtgatcc caccacagaa caacaatgtg    1260
ccacccaggg ctggattctc ccacaggctt agccacgtgt ccatgttccg ttccggattc   1320
agcaacagtt ccgtgagcat catcagagct cctatgttct cttggattca ccgttctgcc   1380
gagttcaaca acatcatcgc atctgatagt attactcaaa tccctgccgt gaagggaaac   1440
ttccttttca atggaagcgt tatcagcgga ccaggattca ctggcggaga tcttgtgaga   1500
```

| | |
|---|---|
| cttaacagct ctggcaacaa cattcagaat agaggctaca tcgaagttcc tatccacttc | 1560 |
| ccatccacat ctactagata cagagttagg gttagatacg cctctgtgac cccaatccac | 1620 |
| cttaacgtga actggggcaa ttcatctatc ttctccaaca ccgttccagc tactgctacc | 1680 |
| tcactcgata atcttcaatc cagcgatttt ggttacttcg aaagtgccaa cgcattcact | 1740 |
| tcttcattgg gcaacatcgt gggtgttagg aatttcagcg gtactgcagg agtgatcatt | 1800 |
| gacagattcg agttcattcc tgttactgcc actcttgagg ctgagtacaa tctttaa | 1857 |

<210> SEQ ID NO 70
<211> LENGTH: 1857
<212> TYPE: DNA
<213> ORGANISM: Artificial Sequence
<220> FEATURE:
<223> OTHER INFORMATION: Mut-N71

<400> SEQUENCE: 70

| | |
|---|---|
| atggacaaca acccaaacat caacgaatgc attccataca actgcttgag taacccagaa | 60 |
| gttgaagtac ttggtggaga acgcattgaa accggttaca ctcccatcga catctccttg | 120 |
| tccttgacac agtttctgct cagcgagttc gtgccaggag ctgggttcgt tctcggacta | 180 |
| gttgacatca tctggggtat cttttggtcca tctcaatggg atgcattcct ggtgcaaatt | 240 |
| gagcagttga tcaaccagag gatcgaagag ttcgccagga accaggccat ctctcgtttg | 300 |
| gaaggattga gcaatctcta ccaaatctat gcagagagct tcagagcttg ggaagccgat | 360 |
| cctactaacc cagctctccg cgtggaaatg cgtattcaat caacgacat gaacagcgcc | 420 |
| ttgaccacag ctatcccatt gttcgcagtc cagaactacc aagttcctct cttgtccgtg | 480 |
| tacgttcaag cagctaatct tcacctcagc gtgcttcgag acgttagcgt gtttgggcaa | 540 |
| agatggggat cgatgctac caccatcaat agccgttaca acgaccttac taggctgatt | 600 |
| ggaaactaca ccgactacgc tgttcgttgg tacaacactg gcttggagcg tgtctggggt | 660 |
| cctgattcta gagattggat cagatacaac cagttcagga gagaattgac cctcacagtt | 720 |
| ttggacattg tgtctctctt cccgaactat gactccagaa cctacccat ccgtacagtg | 780 |
| tcccaactta ccagagaaat ctacactaac ccagttcttg agaacttcga cggtagcttc | 840 |
| cgtggtatgg cccagggtat cgaaagatcc atcaggagcc cacacttgat ggacatcttg | 900 |
| aacagcataa ctatctacac cgatgtgcac agaggatact attactggtc tggacaccag | 960 |
| atcaccgcct ctccagttgg attctccgga cctgagtttg cttttcctct ctatggaact | 1020 |
| atgggaaacg ccgctccaca caacgtatc gttgctcaac taggacaggg tgtctacaga | 1080 |
| accttgtctt ccaccttgta cagaagaccc ttcaatatcg gtcctaacaa ccagcaactt | 1140 |
| tccgttcttg acggaacaga gttcgcctat ggaacctctt ctaacttgcc atccgctgtt | 1200 |
| tacagaaaga gcggaaccgt tgattccttg gacgtgatcc caccacagaa caacaatgtg | 1260 |
| ccacccaggg ctggattctc ccacaggctt agccacgtgt ccatgttccg ttccggattc | 1320 |
| agcaacagtt ccgtgagcat catcagagct cctatgttct cttggattca ccgttctgcc | 1380 |
| gagttcaaca acatcatcgc atctgatagt attactcaaa tccctgccgt gaagggaaac | 1440 |
| ttccttttca tggaagcgt tatcagcgga ccaggattca ctggcggaga tcttgtgaga | 1500 |
| cttaacagct ctggcaacaa cattcagaat agaggctaca tcgaagttcc tatccacttc | 1560 |
| ccatccacat ctactagata cagagttagg gttagatacg cctctgtgac cccaatccac | 1620 |
| cttaacgtga actggggcaa ttcatctatc ttctccaaca ccgttccagc tactgctacc | 1680 |
| tcactcgata atcttcaatc cagcgatttt ggttacttcg aaagtgccaa cgcattcact | 1740 |

```
tcttcattgg gcaacatcgt gggtgttagg aatttcagcg gtactgcagg agtgatcatt    1800
gacagattcg agttcattcc tgttactgcc actcttgagg ctgagtacaa tctttaa       1857

<210> SEQ ID NO 71
<211> LENGTH: 618
<212> TYPE: PRT
<213> ORGANISM: Bacillus thuringiensis

<400> SEQUENCE: 71

Met Glu Glu Asn Asn Gln Asn Gln Cys Ile Pro Tyr Asn Cys Leu Ser
1               5                   10                  15

Asn Pro Glu Glu Val Leu Leu Asp Gly Glu Arg Ile Ser Thr Gly Asn
            20                  25                  30

Ser Ser Ile Asp Ile Ser Leu Ser Leu Val Gln Phe Leu Val Ser Asn
        35                  40                  45

Phe Val Pro Gly Gly Gly Phe Leu Val Gly Leu Ile Asp Phe Val Trp
    50                  55                  60

Gly Ile Val Gly Pro Ser Gln Trp Asp Ala Phe Leu Val Gln Ile Glu
65                  70                  75                  80

Gln Leu Ile Asn Glu Arg Ile Ala Glu Phe Ala Arg Asn Ala Ala Ile
                85                  90                  95

Ala Asn Leu Glu Gly Leu Gly Asn Asn Phe Asn Ile Tyr Val Glu Ala
            100                 105                 110

Phe Lys Glu Trp Glu Glu Asp Pro Asn Asn Pro Glu Thr Arg Thr Arg
        115                 120                 125

Val Ile Asp Arg Phe Arg Ile Leu Asp Gly Leu Leu Glu Arg Asp Ile
    130                 135                 140

Pro Ser Phe Arg Ile Ser Gly Phe Glu Val Pro Leu Leu Ser Val Tyr
145                 150                 155                 160

Ala Gln Ala Ala Asn Leu His Leu Ala Ile Leu Arg Asp Ser Val Ile
                165                 170                 175

Phe Gly Glu Arg Trp Gly Leu Thr Thr Ile Asn Val Asn Glu Asn Tyr
            180                 185                 190

Asn Arg Leu Ile Arg His Ile Asp Glu Tyr Ala Asp His Cys Ala Asn
        195                 200                 205

Thr Tyr Asn Arg Gly Leu Asn Asn Leu Pro Lys Ser Thr Tyr Gln Asp
    210                 215                 220

Trp Ile Thr Tyr Asn Arg Leu Arg Arg Asp Leu Thr Leu Thr Val Leu
225                 230                 235                 240

Asp Ile Ala Ala Phe Phe Pro Asn Tyr Asp Asn Arg Arg Tyr Pro Ile
                245                 250                 255

Gln Pro Val Gly Gln Leu Thr Arg Glu Val Tyr Thr Asp Pro Leu Ile
            260                 265                 270

Asn Phe Asn Pro Gln Leu Gln Ser Val Ala Gln Leu Pro Thr Phe Asn
        275                 280                 285

Val Met Glu Ser Ser Arg Ile Arg Asn Pro His Leu Phe Asp Ile Leu
    290                 295                 300

Asn Asn Leu Thr Ile Phe Thr Asp Trp Phe Ser Val Gly Arg Asn Phe
305                 310                 315                 320

Tyr Trp Gly Gly His Arg Val Ile Ser Ser Leu Ile Gly Gly Gly Asn
                325                 330                 335

Ile Thr Ser Pro Ile Tyr Gly Arg Glu Ala Asn Gln Glu Pro Pro Arg
            340                 345                 350
```

```
Ser Phe Thr Phe Asn Gly Pro Val Phe Arg Thr Leu Ser Asn Pro Thr
            355                 360                 365
Leu Arg Leu Leu Gln Gln Pro Trp Pro Ala Pro Phe Asn Leu Arg
    370                 375                 380
Gly Val Glu Gly Val Glu Phe Ser Thr Pro Thr Asn Ser Phe Thr Tyr
385                 390                 395                 400
Arg Gly Arg Gly Thr Val Asp Ser Leu Thr Glu Leu Pro Pro Glu Asp
                405                 410                 415
Asn Ser Val Pro Pro Arg Glu Gly Tyr Ser His Arg Leu Cys His Ala
            420                 425                 430
Thr Phe Val Gln Arg Ser Gly Thr Pro Phe Leu Thr Thr Gly Val Val
        435                 440                 445
Phe Ser Trp Thr Asp Arg Ser Ala Thr Leu Thr Asn Thr Ile Asp Pro
    450                 455                 460
Glu Arg Ile Asn Gln Ile Pro Leu Val Lys Gly Phe Arg Val Trp Gly
465                 470                 475                 480
Gly Thr Ser Val Ile Thr Gly Pro Gly Phe Thr Gly Gly Asp Ile Leu
                485                 490                 495
Arg Arg Asn Thr Phe Gly Asp Phe Val Ser Leu Gln Val Asn Ile Asn
            500                 505                 510
Ser Pro Ile Thr Gln Arg Tyr Arg Leu Arg Phe Arg Tyr Ala Ser Ser
        515                 520                 525
Arg Asp Ala Arg Val Ile Val Leu Thr Gly Ala Ala Ser Thr Gly Val
    530                 535                 540
Gly Gly Gln Val Ser Val Asn Met Pro Leu Gln Lys Thr Met Glu Ile
545                 550                 555                 560
Gly Glu Asn Leu Thr Ser Arg Thr Phe Arg Tyr Thr Asp Phe Ser Asn
                565                 570                 575
Pro Phe Ser Phe Arg Ala Asn Pro Asp Ile Ile Gly Ile Ser Glu Gln
            580                 585                 590
Pro Leu Phe Gly Ala Gly Ser Ile Ser Ser Gly Glu Leu Tyr Ile Asp
        595                 600                 605
Lys Ile Glu Ile Ile Leu Ala Asp Ala Thr
    610                 615

<210> SEQ ID NO 72
<211> LENGTH: 1857
<212> TYPE: DNA
<213> ORGANISM: Artificial Sequence
<220> FEATURE:
<223> OTHER INFORMATION: cry1C

<400> SEQUENCE: 72
atggaggaaa ataatcaaaa tcaatgcata ccttacaatt gtttaagtaa tcctgaagaa      60
gtacttttgg atggagaacg gatatcaact ggtaattcat caattgatat atctctgtca     120
cttgttcagt ttctggtatc taactttgta ccaggggag gatttttagt tggattaata     180
gattttgtat ggggaatagt tggcccttct caatgggatg catttctagt acaaattgaa     240
caattaatta tgaaagaat agctgaattt gctaggaatg ctgctattgc taatttagaa     300
ggattaggaa acaattttaa tatatatgtg gaagcattta agaatgggga agaagatcct     360
aataatccag aaaccaggac cagagtaatt gatcgctttc gtatacttga tgggctactt     420
gaaagggaca ttccttcgtt tcgaattct ggatttgaag tacccctttt atccgtttat     480
gctcaagcag ccaatctgca tctagctata ttaagagatt ctgtaatttt tggagaaaga     540
```

```
tggggattga caacgataaa tgtcaatgaa aactataata gactaattag gcatattgat    600
gaatatgctg atcactgtgc gaatacgtat aatcggggat taaataattt accgaaatct    660
acgtatcaag attggataac atataatcga ttacggagag acttaacatt gactgtatta    720
gatatcgcag ctttctttcc aaactatgac aataggagat atccaattca gccagttggt    780
caactaacaa gggaagttta tacggaccca ttaattaatt ttaatccaca gttacagtct    840
gtagctcaat tacctacttt taacgttatg gagagcagcc gaattagaaa tcctcattta    900
tttgatatat tgaataatct tacaatcttt acggattggt ttagtgttgg acgcaatttt    960
tattggggag gacatcgagt aatatcaagc cttataggag gtggtaacat aacatctcct   1020
atatatggaa gagaggcaaa ccaggagcct ccaagatcct ttacttttaa tggaccggta   1080
tttaggactt tatcaaatcc tactttacga ttattacagc aaccttggcc agcgccacca   1140
tttaatttac gtggtgttga aggagtagaa ttttctacac ctacaaatag ctttacgtat   1200
cgaggaagag gtacggttga ttcattaact gaattaccgc ctgaggataa tagtgtgcca   1260
cctcgcgaag gatatagtca tcgtttatgt catgcaactt ttgttcaaag atctggaaca   1320 cctttttttaa caactggtgt agtatttttct tggaccgatc gtagtgcaac tcttacaaat   1380
acaattgatc cagagagaat taatcaaata cctttagtga aaggatttag agtttggggg   1440
ggcacctctg tcattacagg accaggattt acaggagggg atatccttcg aagaaatacc   1500
tttggtgatt ttgtatctct acaagtcaat attaattctc caattaccca agataccgt    1560 ttaagatttc gttacgcttc cagtagggat gcccgagtta tagtattaac aggagcggca   1620
tccacaggag tgggaggcca agttagtgta aatatgcctc ttcagaaaac tatggaaata   1680
ggggagaact taacatcaag aacatttaga tataccgatt ttagtaatcc tttttcattt   1740
agagctaatc cagatataat tgggataagt gaacaacctc tatttggtgc aggttctatt   1800
agtagcggtg aactttatat agataaaatt gaaattattc tagcagatgc aacataa     1857

<210> SEQ ID NO 73
<211> LENGTH: 28
<212> TYPE: DNA
<213> ORGANISM: Artificial Sequence
<220> FEATURE:
<223> OTHER INFORMATION: Primer for E116A

<400> SEQUENCE: 73
gcagagagct tcagagcttg ggaagccg                                           28

<210> SEQ ID NO 74
<211> LENGTH: 20
<212> TYPE: DNA
<213> ORGANISM: Artificial Sequence
<220> FEATURE:
<223> OTHER INFORMATION: Primer for E128V

<400> SEQUENCE: 74
cccagctctc cgcgtggaaa                                                    20

<210> SEQ ID NO 75
<211> LENGTH: 28
<212> TYPE: DNA
<213> ORGANISM: Artificial Sequence
<220> FEATURE:
<223> OTHER INFORMATION: Primer for G183E

<400> SEQUENCE: 75
gggcaaagat gggaattcga tgctgcaa                                           28
```

<210> SEQ ID NO 76
<211> LENGTH: 31
<212> TYPE: DNA
<213> ORGANISM: Artificial Sequence
<220> FEATURE:
<223> OTHER INFORMATION: Primer for A187T

<400> SEQUENCE: 76
ggggattcga tgctaccacc atcaatagcc g                       31

<210> SEQ ID NO 77
<211> LENGTH: 38
<212> TYPE: DNA
<213> ORGANISM: Artificial Sequence
<220> FEATURE:
<223> OTHER INFORMATION: Primer for V227I

<400> SEQUENCE: 77
ctgattctag agattggatc agatacaacc agttcagg                38

<210> SEQ ID NO 78
<211> LENGTH: 32
<212> TYPE: DNA
<213> ORGANISM: Artificial Sequence
<220> FEATURE:
<223> OTHER INFORMATION: Primer for A245S

<400> SEQUENCE: 78
cagttttgga cattgtgtct ctcttcccga ac                      32

<210> SEQ ID NO 79
<211> LENGTH: 33
<212> TYPE: DNA
<213> ORGANISM: Artificial Sequence
<220> FEATURE:
<223> OTHER INFORMATION: Primer for P248S

<400> SEQUENCE: 79
attgtggctc tcttcagcaa ctatgactcc aga                     33

<210> SEQ ID NO 80
<211> LENGTH: 36
<212> TYPE: DNA
<213> ORGANISM: Artificial Sequence
<220> FEATURE:
<223> OTHER INFORMATION: Primer for R254T

<400> SEQUENCE: 80
cccgaactat gactccagaa cctaccctat ccgtac                  36

<210> SEQ ID NO 81
<211> LENGTH: 27
<212> TYPE: DNA
<213> ORGANISM: Artificial Sequence
<220> FEATURE:
<223> OTHER INFORMATION: Primer for S283M

<400> SEQUENCE: 81
gcttccgtgg tatggcccag ggtatcg                            27

<210> SEQ ID NO 82
<211> LENGTH: 30
<212> TYPE: DNA
<213> ORGANISM: Artificial Sequence
<220> FEATURE:

<223> OTHER INFORMATION: Primer for S283M&G286R

<400> SEQUENCE: 82
ccgtggtatg gcccagagga tcgaaagatc            30

<210> SEQ ID NO 83
<211> LENGTH: 30
<212> TYPE: DNA
<213> ORGANISM: Artificial Sequence
<220> FEATURE:
<223> OTHER INFORMATION: Primer for G286R

<400> SEQUENCE: 83
cgtggttctg cccagaggat cgaaagatcc            30

<210> SEQ ID NO 84
<211> LENGTH: 44
<212> TYPE: DNA
<213> ORGANISM: Artificial Sequence
<220> FEATURE:
<223> OTHER INFORMATION: Primer for A309V

<400> SEQUENCE: 84
gcataactat ctacaccgat gtgcacagag gatactatta ctgg            44

<210> SEQ ID NO 85
<211> LENGTH: 31
<212> TYPE: DNA
<213> ORGANISM: Artificial Sequence
<220> FEATURE:
<223> OTHER INFORMATION: Primer for M322T

<400> SEQUENCE: 85
ctggacacca gatcaccgcc tctccagttg g            31

<210> SEQ ID NO 86
<211> LENGTH: 31
<212> TYPE: DNA
<213> ORGANISM: Artificial Sequence
<220> FEATURE:
<223> OTHER INFORMATION: Primer for T334A

<400> SEQUENCE: 86
ccggacctga gtttgctttt cctctctatg g            31

<210> SEQ ID NO 87
<211> LENGTH: 43
<212> TYPE: DNA
<213> ORGANISM: Artificial Sequence
<220> FEATURE:
<223> OTHER INFORMATION: Primer for Y338F

<400> SEQUENCE: 87
gtttaccttt cctctcttcg gaaacgctgg aaacgccgct cca            43

<210> SEQ ID NO 88
<211> LENGTH: 31
<212> TYPE: DNA
<213> ORGANISM: Artificial Sequence
<220> FEATURE:
<223> OTHER INFORMATION: Primer for I375P

<400> SEQUENCE: 88
cccttcaata tcggtcctaa caaccagcaa c            31

<210> SEQ ID NO 89
<211> LENGTH: 38
<212> TYPE: DNA
<213> ORGANISM: Artificial Sequence
<220> FEATURE:
<223> OTHER INFORMATION: Primer for Q379E

<400> SEQUENCE: 89
ggtatcaaca accaggaact ttccgttctt gacggaac                                38

<210> SEQ ID NO 90
<211> LENGTH: 38
<212> TYPE: DNA
<213> ORGANISM: Artificial Sequence
<220> FEATURE:
<223> OTHER INFORMATION: Primer for S381F

<400> SEQUENCE: 90
ggtatcaaca accagcaact tttcgttctt gacggaac                                38

<210> SEQ ID NO 91
<211> LENGTH: 31
<212> TYPE: DNA
<213> ORGANISM: Artificial Sequence
<220> FEATURE:
<223> OTHER INFORMATION: Primer for E412V

<400> SEQUENCE: 91
cgttgattcc ttggacgtga tcccaccaca g                                       31

<210> SEQ ID NO 92
<211> LENGTH: 35
<212> TYPE: DNA
<213> ORGANISM: Artificial Sequence
<220> FEATURE:
<223> OTHER INFORMATION: Primer for N417D

<400> SEQUENCE: 92
gatcccacca caggataaca gcgtgccacc caggc                                   35

<210> SEQ ID NO 93
<211> LENGTH: 27
<212> TYPE: DNA
<213> ORGANISM: Artificial Sequence
<220> FEATURE:
<223> OTHER INFORMATION: Primer for Q424A

<400> SEQUENCE: 93
gtgccaccca gggctggatt ctcccac                                            27

<210> SEQ ID NO 94
<211> LENGTH: 17
<212> TYPE: DNA
<213> ORGANISM: Artificial Sequence
<220> FEATURE:
<223> OTHER INFORMATION: Sequencing primer

<400> SEQUENCE: 94
accgactacg ctgttcg                                                       17

<210> SEQ ID NO 95
<211> LENGTH: 17
<212> TYPE: DNA
<213> ORGANISM: Artificial Sequence
<220> FEATURE:
<223> OTHER INFORMATION: Sequencing primer

```
<400> SEQUENCE: 95
aatgttgttg ccagagc                                                      17

<210> SEQ ID NO 96
<211> LENGTH: 27
<212> TYPE: DNA
<213> ORGANISM: Artificial Sequence
<220> FEATURE:
<223> OTHER INFORMATION: Sequencing primer

<400> SEQUENCE: 96
aaactcgaga tggacaacaa cccaaac                                           27

<210> SEQ ID NO 97
<211> LENGTH: 30
<212> TYPE: DNA
<213> ORGANISM: Artificial Sequence
<220> FEATURE:
<223> OTHER INFORMATION: Sequencing primer

<400> SEQUENCE: 97
tttgaattct taaagattgt actcagcctc                                        30

<210> SEQ ID NO 98
<211> LENGTH: 17
<212> TYPE: DNA
<213> ORGANISM: Artificial Sequence
<220> FEATURE:
<223> OTHER INFORMATION: Sequencing primer

<400> SEQUENCE: 98
ggtcacagag gcgtatc                                                      17
```

MUTANT BACILLUS THURINGIENSIS PROTEINS AND GENES ENCODING THE SAME WITH IMPROVED INSECTICIDAL ACTIVITY AND USE THEREOF

CROSS-REFERENCE TO RELATED APPLICATIONS

The present application is a continuation in part application of International Patent Application PCT/KR2014/000657, filed Jan. 23, 2014, which claims the benefit of Korean Patent Application No. 10-2013-0032329 and 10-2014-0004841, filed Mar. 26, 2013 and Jan. 15, 2014, respectively, in the Korean Intellectual Property Office, the disclosure of which are incorporated herein.

STATEMENT OF GOVERNMENT SUPPORT

The invention was made with government support under grant number PJ011135022015 "Cooperative Research Program for Agriculture Science & Technology Development" awarded by Rural Development Administration, Republic of Korea.

STATEMENT OF SEQUENCE LISTING

The Sequence Listing submitted in text format (.txt) filed on Sep. 17, 2015, named "SequenceListing.txt", created on Sep. 8, 2015 (268 KB), is incorporated herein by reference.

BACKGROUND OF INVENTION

Field of the Invention

The present disclosure generally relates to modified insecticidal Bacillus thuringiensis proteins and genes coding for the same with improved insecticidal activity.

Description of the Related Art

Order lepidoptera includes butterflies and moths. At present there are estimated 200,000 species of lepidoptera worldwide, which accounts for about 10% of the total described species of the animal kingdom. It is one of the most widespread and widely recognizable insect orders. In Korea, about 3,200 species have been found and account for about 40% of the crop pests. Lepidoptera pests contribute a major share to the crop loss. Larvae of these pests are very voracious polyphagous particularly at the younger instars causing a drastic damage to the crop foliage and produce.

For the last five decades, these pests have been mostly controlled by chemical and synthetic pesticides. But the indiscriminate use of the chemicals has raised serious health and environmental safety concerns. This has led to a paradigm shift in the pest control to the biopesticides.

Among biopesticides, Bacillus thuringiensis (BT) and its endotoxins genes have been widely studied and developed for the pest control.

Bacillus thuringiensis is a gram positive bacterium that produces proteinaceous crystalline inclusions during sporulation. These crystal proteins are often highly toxic to various insects such as Lepidoptera, Coleoptera and Diptera.

Insecticidal BT crystal proteins can differ extensively in their structures and insecticidal activities. These proteins are encoded by genes typically located on large plasmid, greater than 30 MDa in size. Thus a number of BT toxin genes have been isolated and characterized.

Traditional commercial BT biopesticide products are purified BT strains isolated from natural sources or genetically modified strains which are disclosed in U.S. Pat. Nos. 5,080,897 and 4,935,353.

Also disclosed are various transgenic crops genetically modified to express cry1-type endotoxin for Cottons (Perlak et al., Biotechnol. 8:939-943, 1990), Rice (Fujimoto et al., Biotechnol. 11:1151-1155, 1993), Corns (Bourguet et al., Proc. Biol. Sci. 267:117-122, 2000), Tobaccos (Strizhov et al., Proc. Natl. Acad. Sci. U.S.A. 24:15012-15017, 1996), Tomatos (Perlak et al., Proc. Natl. Acad. Sci. U.S.A. 88:3324-3328, 1991), Beans (Stewart et al., Plant Physiol. 112:121-129, 1996), and Alphafas (Strizhov et al., Proc. Natl. Acad. Sci. U.S.A. 24:15012-15017, 1996).

Although Bt products have significant advantages as biological control agents, the conventional use of Bt insecticides have been faced with some limitations such as a narrow host spectrum, a short shelf life and the development of pest insect resistance.

Korean Patent No. 280380 relates to an endotoxin protein from BT NT0423 strain and insecticidal composition comprising the same. Korean Patent No. 432140 relates to an endotoxin protein from K-1 strain and insecticidal composition comprising the same. Korean Patent No. 436026 relates to a BT KFRI-2 strain having pesticidal activity against lepidoptera and diptera insects and insecticidal composition comprising the same. Korean Patent No. 599414 relates to a BT K-3 strain expressing novel endotoxin and insecticidal composition comprising the same. Also disclosed is a method for introducing two genes from BT by gene stacking to transgenic rice (Yang et al., Pest Manag. Sci. 67:414-422, 2011) and a transgenic mustard expressing cry1A and cry1C (Cao J et al., Plant Cell Rep. 27:479-487, 2008)

None are disclosed in the prior arts regarding endotoxins having broader host range while maintaining or showing superior insecticidal activity against Order lepidoptera.

Thus there exist needs to develop strategies that will delay or counteract the resistance at the molecular level by developing novel endotoxin genes.

SUMMARY OF THE INVENTION

In one aspect, there are provided isolated mutant cry1Ac proteins engineered from cry1Ac protein, the mutant protein having the amino acid sequence selected from the group consisting of SEQ ID NOs: 2 to 35.

Also provided are isolated nucleic acid molecules encoding the present mutant proteins. In one embodiment, the nucleic acid molecules are represented by the sequence selected from the group consisting of SEQ ID NOs: 37 to 70.

Also provided are vectors comprising the nucleic acid molecule as disclosed herein.

Also provided are cells transformed with the present vectors.

Also provided are transgenic plant cells, plants or plant parts comprising transformed with the present, and wherein the plant part is a seed, a boll, a leaf, a flower, a stem, a root, or any portion thereof; or the plant part is a non-regenerable portion of the seed, boll, leaf, flower, stem or root.

Also provided are compositions for inhibiting the growth of Lepidopteran pest comprising at least one mutant protein according to the present disclosure.

Also provided are methods of controlling Lepidopteran pests comprising contacting the pests with an insecticidally effective amount of the composition according to the present disclosure.

In other aspect, there are provided methods of controlling the growth of Lepidopteran pest comprising exposing the pest to the transgenic plant cell, plant or plant part, wherein the plant cell, plant or plant part thereof expresses a Lepidopterous inhibitory amount of the mutant cry1Ac protein as disclosed herein.

The present proteins, compositions and methods can be effectively used for controlling the growth of Lepidopterous pest including, without being limited to, for example, *Ostrinia furnacalis, Ostrinia nubilalis, Chilo suppressalis, Cnaphalocrocis medinalis, Naranga aenescens, Mamestra brassicae, Spodoptera litura, Spodoptera exigua, Spodoptera furgiperda, Helicoverpa armigera, Helicoverpa assulta, Helicoverpa zea, Cucullia fraternal, Pseudaletia separata, Acronicta rumicis, Amphipyra monolitha, Anadevidia peponis, Acanthoplusia agnata, Maruca testulalis, Matsumuraeses phaseoli, Agrotis segetum, Pieris rapae, Plutella xylostella, Endoclyta excrescens, Nepticulidae, Adelidae, Bucculatrigidae, Gracillariidae, Acrolepiopsis sapporensis, Glyphipterigidae, Arctia caja, Bombyx mori, Brahmaea certhia, Dendrolimus spectabilis, Hypantria cunea* or *Lymantria dispar*.

The foregoing summary is illustrative only and is not intended to be in any way limiting. Additional aspects and/or advantages of the invention will be set forth in part in the description which follows and, in part, will be obvious from the description, or may be learned by practice of the invention.

BRIEF DESCRIPTION OF THE DRAWINGS

These and/or other aspects and advantages of the invention will become apparent and more readily appreciated from the following description of the embodiments, taken in conjunction with the accompanying drawings of which:

FIGS. 1A and 1B are diagrams showing the mutated residues in each of 34 mutant Cry1Ac proteins according to the present disclosure, in which ellipse represents mutated amino acid sequences and rectangle represents unchanged amino acid sequences. Amino acid residues are represented by a single letter code.

DETAILED DESCRIPTION OF THE EMBODIMENTS

Figure 1A:
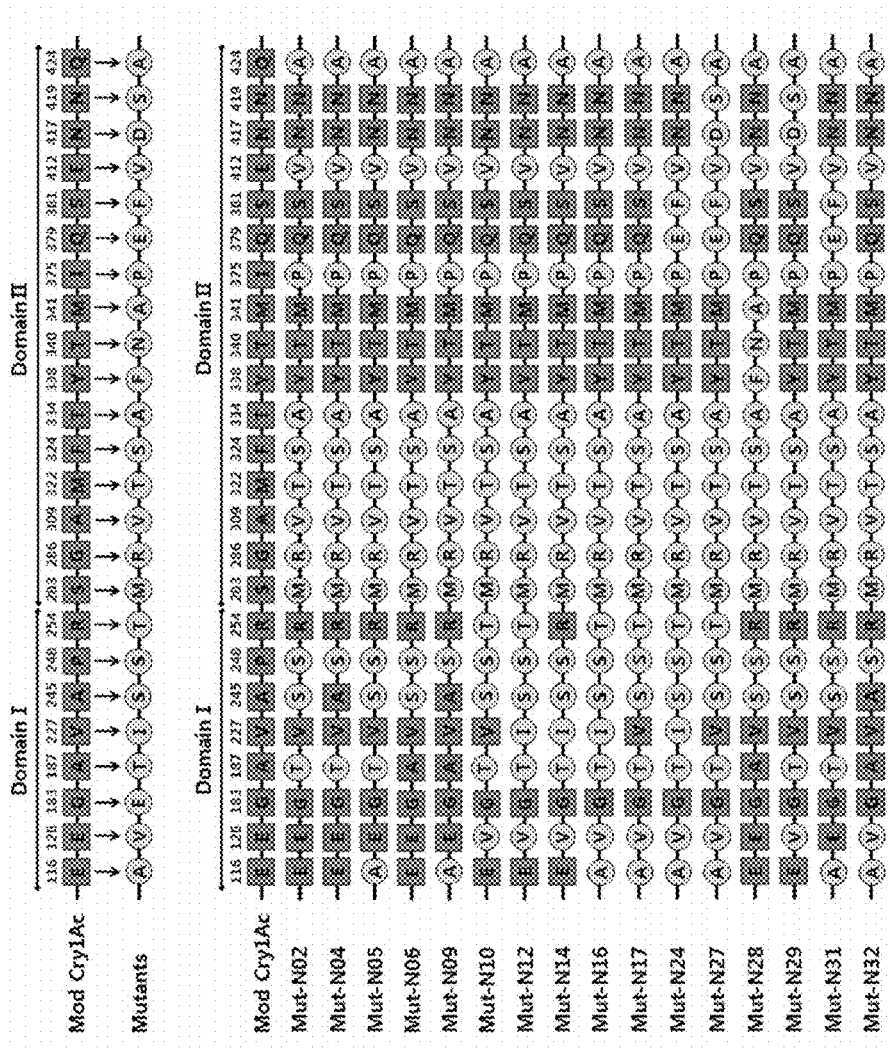

In the present disclosure, mutant cry1Ac proteins engineered from a wild type progenitor protein Cry1Ac are described. The mutant Cry1Ac of the present disclosure are distinguished from the previous proteins such as Cry1Ac, or ones as disclosed in Korean Patent Nos. 280380, 432140, 436026 and 599414. For example, in Table 2 of the present disclosure, mutant Cry1Ac according the one embodiment of the present disclosure was found to have 6.6 times greater insecticidal activity against *Plutella xylostella*, and 1.5~4.3 times against *Ostrinia furnacalis* compared to Cry1Ac. Further the present mutant Cry1Ac was found to have an insecticidal activity against *Spodoptera exigua* against which Cry1Ac does not have any activity. The present mutant Cry1Ac proteins surprisingly and unexpectedly exhibit high levels of toxic activity against Lepidopteran pest species.

In addition the present proteins exhibit broader host range toxic properties within the order Lepidoptera compared to the progenitor protein. As shown in Table 2 of the present disclosure, Cry1A and Cry1C did not have any insecticidal activity against *Spodoptera exigua*, and *Ostrinia furnacalis* and *Plutella xylostella*, respectively. In contrast, the present Cry1A proteins have been found to have a strong insecticidal activity against all the three species. This indicates the host range exerted by the present protein which is broader than the previous proteins.

More than 70 mutants having more than one amino acid substitution across 24 amino acid residues located in domain I and II of Cry1A protein were generated and the mutants having a particular combination of substitution that exert a broad Lepidopteran species host range as well as an increased Lepidopteran species inhibitory activity when compared to those of the baseline or progenitor proteins. The present mutants have been developed based on Cry1A type, which is insecticidal against lepidopteran pest. Thus the present mutant proteins can be efficiently used for controlling the various pests belong to Order lepidoptera.

The Lepidopteran species are intended to mean insects that feed on various plants and plant tissues and/or to include caterpillars or neonates with chewing mouthparts that are suitable for feeding on various parts of a plant. Most caterpillars are defoliators or miners of succulent plant tissues. Such insects include *Ostrinia furnacalis, Ostrinia nubilalis, Chilo suppressalis, Cnaphalocrocis medinalis, Naranga aenescens, Mamestra brassicae, Spodoptera litura, Spodoptera exigua, Spodoptera furgiperda, Helicoverpa armigera, Helicoverpa assulta, Helicoverpa zea, Cucullia fraternal, Pseudaletia separata, Acronicta rumicis, Amphipyra monolitha, Anadevidia peponis, Acanthoplusia agnata, Maruca testulalis, Matsumuraeses phaseoli, Agrotis segetum, Pieris rapae, Plutella xylostella, Endoclyta excrescens, Nepticulidae, Adelidae, Bucculatricidae, Gracillariidae, Acrolepiopsis sapporensis, Glyphipterigidae, Arctia caja, Bombyx mori, Brahmaea certhia, Dendrolimus spectabilis, Hypantria cunea* or *Lymantria dispar*.

The present mutant Cry1Ac proteins contain more than one following substitution mutations compared to the progenitor protein (SEQ ID NO: 1) at 24 amino acid residues in domain I and II: E116A, E128V, G183E, A187T, V227I, A245S, P248S, R254T, S283M, G286R, A309V, M322T, F324S, T334A, Y338F, T340N, M341A, I375P, Q379E, S381F, E412V, N417D, N419S and Q424A in domain I and II of progenitor protein, in which amino acids are represented a single letter code and numbers represents amino acid residues based on SEQ ID NO: 1. The present mutants include proteins set forth as SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34 and SEQ ID NO: 35, and insect inhibitory fragments thereof.

Also provided are insect inhibitory compositions which comprise the above described mutant proteins. Such compositions may further comprise at least one additional insect inhibitory agent different from the present mutant proteins included in the composition. The insect inhibitory agent is selected from any number of insect inhibitory agents including an insect inhibitory protein, an insect inhibitory dsRNA molecule, and one or more chemical agents useful in controlling insect pests. Known pesticides within these categories may be found in The Pesticide Manual, 11th Ed., C. D. S. Tomlin, Ed., British Crop Protection Council, Farnham, Surry, UK (1997). The chemical insecticides that are useful in the present disclosure can be of any grade or purity that passes in the trade as such insecticide. One of ordinary skill in the related art can readily identify or select the additional insecticide that can be used with the present mutant protein(s).

As used herein, the phrase "Lepidopteran inhibitory amount" refers to an amount of a protein of the present disclosure alone or with other agents targeting the applicable Lepidopteran species for control, which results in any measurable inhibition of target insects belonging to the order Lepidoptera related to viability, growth, development, reproduction, feeding behavior, mating behavior, and or any measurable decrease in the adverse effects caused by Lepidopteran insects feeding on a plant.

As used herein in the context of a mutant Cry1Ac protein of the present disclosure, an "enhanced Lepidopteran inhibitory activity refers to any measurable increase in the inhibition of Lepidopteran viability, growth, development, reproduction, feeding behavior, mating behavior and/or any measurable decrease in the adverse effects caused by Lepidopteran feeding on a composition containing that the present mutant protein(s) relative to the corresponding inhibitory activity observed with the progenitor protein (SEQ ID NO: 1) and/or Cry 1C (SEQ ID NO: 71).

In one embodiment, Cry1Ac mutants as disclosed herein can exhibit about 2 to about 7 fold greater inhibitory activity against *P. xylostella, S. exigua* and *O. furnacalis* over Cry1Ac and Cry1C.

In one embodiment, Cry1Ac mutants as disclosed herein can exhibit an enhanced target pest inhibitory spectrum over Cry 1Ac and Cry1C.

Also provided are recombinant polynucleotides encoding the present mutant Cry1Ac proteins. In one embodiment, the present protein can be expressed from recombinant DNA constructs in which a polynucleotide molecule with the open reading frame encoding the present protein is operably linked to elements such as a promoter and any other regulatory element required for expression in the system for which the construct is intended. For example, plant-functional promoters can be operably linked to an applicable present mutant Cry1Ac gene to enable expression of the protein in plants. Other useful elements that can be operably linked to the present mutant coding sequences include, but are not limited to, enhancers, introns, leaders, encoded protein immobilization tags (HIS-tag), encoded sub-cellular translocation peptides (i.e. plastid transit peptides, signal peptides), encoded polypeptide sites for post-translational modifying enzymes, ribosomal binding sites, and segments designed for use as RNAi triggers for suppression of one or more genes either in plants or in a particular target pest species.

Exemplary recombinant polynucleotide molecules provided herein include, but are not limited to, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, and SEQ ID NO:70, each of which encode the respective proteins each having the amino acid sequence as set forth in SEQ ID NOs: 2 to 35. Because of the redundancy of the genetic code, the codons of a recombinant polynucleotide molecule encoding the present may be substituted for synonymous codons; and are within the scope of the present disclosure. Therefore recombinant polynucleotides encoding any of the mutants Cry1Ac disclosed herein are also provided.

Also provided are vectors which comprising polynucleotide molecule encoding the present mutant. The vectors include a plasmid, baculovirus, artificial chromosome, virion, cosmid, phagemid, phage, or viral vector. Such vectors can be used to achieve stable or transient expression of a mutant encoding sequence in a host cell; and subsequent expression to polypeptides.

Also provided herewith are transgenic or transformed bacteria, transgenic plant cells, transgenic plants, and transgenic plant parts that contain any a recombinant polynucleotide of the present disclosure that expresses any one or more mutant gene. The term "bacterial cell" can include, but are not limited to, an *Agrobacterium*, a *Bacillus*, an *Escherichia*, a *Salmonella*, a *Pseudomonas*, or a *Rhizobium* cell. The term "plant cell" or "plant" include an alfalfa, banana, barley, bean, beet, broccoli, cabbage, brassica, brinjal, carrot, cassava, castor, cauliflower, celery, chickpea, Chinese cabbage, celery, citrus, coconut, coffee, corn, clover, cotton, a cucurbit, cucumber, Douglas fir, eggplant, eucalyptus, flax, garlic, grape, guar, hops, leek, legumes, lettuce, Loblolly pine, millets, melons, nectarine, nut, oat, okra, olive, onion, ornamental, palm, pasture grass, papaya, pea, peach, peanut, pepper, pigeonpea, pine, potato, poplar, pumpkin, Radiata pine, radish, rapeseed, rice, rootstocks, rye, safflower, shrub, sorghum, Southern pine, soybean, spinach, squash, strawberry, sugar beet, sugarcane, sunflower, sweet corn, sweet gum, sweet potato, switchgrass, tea, tobacco, tomato, triticale, turf grass, watermelon, and wheat plant cell or plant.

In certain embodiments, transgenic plants and transgenic plant parts regenerated from a transgenic plant cell are provided; transgenic plants can be obtained from a transgenic seed; transgenic plant parts can be obtained by cutting, snapping, grinding or otherwise disassociating the part from the plant; the plant part can be a seed, a boll, a leaf, a flower, a stem, a root, or any portion thereof; and a transgenic plant part provided herein is a non-regenerable portion of a transgenic plant part. As used in this context, a "non-regenerable" portion of a transgenic plant part is a portion that cannot be induced to form a whole plant or that cannot be induced to form a whole plant that is capable of sexual and/or asexual reproduction. A non-regenerable portion of a plant part is a portion of a transgenic pollen, ovule, seed, boll, leaf, flower, stem, or root.

Also provided herein are methods of making transgenic plants that contain insect inhibitory amounts of the present mutant. Such plants can be made by introducing a recombinant polynucleotide that encodes any of the present mutant proteins provided herein into a plant cell, and selecting a plant derived from said plant cell that expresses a Lepidopteran inhibitory amount of the present mutants. Plants can be derived from the plant cells by regeneration, seed, pollen, or meristem transformation techniques.

Also provided are transgenic plants and host cells that express expresses a Lepidopteran inhibitory amount of the present mutant to control Lepidopteran infestation. Any of the aforementioned plant species can be used for protecting a plant from Lepidopteran infestation provided herein as long as the plant is transformed with a polynucleotide construct of the present disclosure designed to express the present mutant.

Lepidopteran infestations of crop plants are controlled by providing the crop plants with a recombinant polynucleotide sequence encoding one or more of the present mutant. Such transgenic crops produce or are treated to contain a Lepidopteran inhibitory amounts of an applicable present mutant, and such crops are treated with sufficient mutant protein(s) by (i) applying any composition comprising or encoding the present mutant to the plant or a seed that gives rise to the plant; and/or (ii) transforming the plant or a plant cell that gives rise to the seed and ultimately, the plant, with a polynucleotide encoding an mutant of the present disclosure. The plant may be a transiently or stably transformed transgenic plant comprising a transgene that expresses Lepidopteran inhibitory amount of a mutant of the present disclosure. The plant may be a non-transgenic plant to which a composition comprising a mutant of the present disclosure has been applied. In such methods, the plant is a dicot plant, and more specifically may be a cotton, soybean or alfalfa plant. The Lepidopteran insects include adults, nymphs, neonates, larva, such as set forth above.

The present disclosure is further explained in more detail with reference to the following examples. These examples, however, should not be interpreted as limiting the scope of the present invention in any manner.

EXAMPLES

Materials and Methods

1. Construction of Mutant Cry1Ac Gene
1-1. Template and Primers Used for Mutagenesis The mod-cry1Ac gene which was used a template for various mutants as disclosed herein and has a crop-preferring codon usage, was kindly provided by Dr. Beom-Seok Park (National Institute of Agricultural Biotechnology, RDA, Korea). For the mutation of mod-cry1Ac, the alignment of the amino acid sequence of the Mod-Cry1Ac (SEQ ID NO: 1) and other Cry1-type proteins was performed using MegAlign (DNASTAR Inc., USA) and 24 amino acid residues were selected in domain I and II. For the mutagenesis, 21 primers based on the codon usage in pooled sequences of Chinese cabbage genes were designed to change 24 amino acid residues located in domain I and domain II (Table. 1). Primers were designed to be between 25 and 45 bases in length with a melting temperature (Tm) over 75° C., which was calculated using the QuickChange® Tm calculator (available online at http://www.stratagene.com). The primers designed are represented by SEQ ID Nos: 73 to 93.

TABLE 1

Nucleotide sequences of primers used for construction of the present mutant cry1Ac genes.

| | Primer | Primer sequence<sup>a</sup> (5'→3') | Mutated residues | SEQ ID NOs |
|---|---|---|---|---|
| Domain I | E116 A | GCAGAGAGCTTCAG AGCTTGGGAAGCCG | E116A | 73 |
| | E128 V | CCCAGCTCTCCGCG TGGAAA | E128V | 74 |
| | G183 E | GGGCAAAGATGGGA ATTCGATGCTGCAA | G183E | 75 |
| | A187 T | GGGGATTCGATGCT ACCACCATCAATAG CCG | A187T | 76 |
| | V227 I | CTGATTCTAGAGAT TGGATCAGATACAA CCAGTTCAGG | V227I | 77 |
| | A245 S | CAGTTTTGGACATT GTGTCTCTCTTCCC GAAC | A245S | 78 |
| | P248 S | ATTGTGGCTCTCTT CAGCAACTATGACT CCAGA | P248S | 79 |
| | R254 T | CCCGAACTATGACT CCAGAACCTACCCT ATCCGTAC | R254T | 80 |
| Domain II | S283 M | GCTTCCGTGGTATG GCCCAGGGTATCG | S283M | 81 |
| | S283 M & G286 R | CCGTGGTATGGCCC AGAGGATCGAAAGA TC | S283M, G286R | 82 |
| | G286 R | CGTGGTTCTGCCCA GAGGATCGAAAGAT CC | G286R | 83 |
| | A309 V | GCATAACTATCTAC ACCGATGTGCACAG AGGATACTATTACT GGT | A309V | 84 |
| | M322 T | CTGGACACCAGATC ACCGCCTCTCCAGT TGG | M322T, F324S | 85 |
| | T334 A | CCGGACCTGAGTTT GCTTTTCCTCTCTA TGG | T334A | 86 |
| | Y338 F | GTTTACCTTTCCTC TCTTCGGAAACGCT GGAAACGCCGCTCCA | Y338F, T340N, M341A | 87 |

TABLE 1-continued

Nucleotide sequences of primers used for construction of the present mutant cry1Ac genes.

| Primer | Primer sequence[a] (5'→3') | Mutated residues | SEQ ID NOs |
|---|---|---|---|
| I375 P | CCCTTCAATATCGG TCCTAACAACCAGC AAC | I375P | 88 |
| Q379 E | GGTATCAACAACCA GGAACTTTCCGTTC TTGACGGAAC | Q379E | 89 |
| S381 F | GGTATCAACAACCA GCAACTTTTCGTTC TTGACGGAAC | S381F | 90 |
| E412 V | CGTTGATTCCTTGG ACGTGATCCCACCA CAG | E412V | 91 |
| N417 D | GATCCCACCACAGG ATAACAGCGTGCCA CCCAGGC | N417D, N419S | 92 |
| Q424 A | GTGCCACCCAGGGC TGGATTCTCCCAC | Q424A | 93 |

[a]Underlined sequences indicate mutagenesis site.

1-2 Multi Site-Directed Mutagenesis

A total of 71 mutated mod-cry1Ac genes was constructed using the primers as in 1-1 alone or in combination and using QuickChange® multisite-directed mutagenesis method (Stratagene, USA) according to the manufacturer's instruction. Briefly, template DNA was replicated with three to five mutagenic primers using enzyme blend including QuickChange® DNA polymerase (Stratagene, USA) according to the following cycle parameters; step 1, 95° C., 1 min; step 2, 95° C., 1 min; step 3, 55° C., 1 min; step 4, 65° C., 17 min (every successive cycle repeats steps 2 to 4, 34 times); step 5, 4° C., unlimited. All DNA amplifications were performed with a DNA Thermal Cycler (BIO-RAD, USA). The disintegration of methylated or hemimethylated template DNA was performed with DpnI (New England Biolab, USA). Mutated single stranded-DNA was then transformed into XL-10 Gold Ultracompetent cells (Stratagene, USA). Each mutant was confirmed by DNA sequencing analysis using specific primers, Mod-cry1Ac-F 5'-ACCGACTACGCTGT-TCG-3') (SEQ ID NO: 94) and Mod-cry1Ac-R (5'-AATGT-TGTTGCCAGAGC-3') (SEQ ID NO: 95). The mod-cry1Ac gene and mutated genes (Mod-Mut-NO2 and Mod-Mut-No. 5) were used as a template for the next round of mutagenesis.

1-3 Construction of Recombinant Baculovirus Expressing Mutant Cry1Ac Proteins

The mutant genes synthesized in 1-2 were expressed as a fusion protein with polyhedrin using a baculovirus expression system. For the construction of baculovirus transfer vectors expressing the wild type mod-cry1Ac gene, mod-cry1Ac gene as in 1-1 was amplified by PCR using the following primers, Mod1Ac-ATG-F containing XhoI-F at 5'-end (5'-AAACTCGAGATGGACAACAACCCAAAC-3') (SEQ ID NO: 96) and Mod1Ac-TAA-R containing EcoRI site at 5'-end (5'-TTTGAATTCTTAAAGATTG-TACTCAGCCTC-3') (SEQ ID NO: 97). Then each of the PCR-amplified mod-cry1Ac gene fragment was digested with XhoI and EcoRI, and inserted into pOBI vector (Kim et al., Biol. Control 27:222-227, 2008) digested with the same restriction endonucleases to obtain pOB-Mod-Cry1Ac. In order to construct the baculovirus transfer vector expressing mutant cry1Ac genes as in 1-2, each mutant Cry1Ac gene was digested with XbaI and BglII to yield 821 bp containing a mutant region(s) used as a cassette fragment, and each cassette fragment was introduced into pOB-Mod-Cry1Ac digested with the same restriction endonucleases to obtain vectors containing each mutated Mod-cry1Ac gene. Each mutant gene in the constructed pOB-Mut-cry1Ac was verified by DNA sequencing using specific primers, Mut-seq-F (5'-ACCGACTACGCTGTTCG-3') (SEQ ID NO: 94) and Mut-seq-R (5'-GGTCACAGAGGCGTATC-3') (SEQ ID NO: 98). Mutant Cry1Ac proteins were expressed using the baculovirus expression system with a defective viral genome, bApGOZA (Je Y H, et al., Baculovirus expression vectors that incorporate the foreign protein into viral occlusion bodies. *Biotechniques* 34:81-87 (2003)). The bApGOZA DNA (500 ng) and each transfer vector DNA (2 μg) were cotransfected into Sf9 cells using 20 μl of Cellfectin® II™ reagent (Invitrogen Co., USA) according to the manufacturer's instruction. At 5 days post-transfection, the supernatant containing recombinant viruses was harvested and used as inoculum for the proliferation of recombinant virus.

1-4. Analysis of Fusion Proteins Constructed on SDS-PAGE

To analyze the fusion proteins constructed in 1-3, Sf9 cells infected with the recombinant viruses of 1-3 were lysed with cell-lysis buffer (50 mM Tris-HCl, pH 8.0; 0.4% SDS; 10 mM EDTA; 5% 2-Mercaptoethanol), sonicated (Duty cycle, 30; Output Control, 3) for 120 s and centrifuged at 15,000 rpm for 10 min. The resulting pellet was washed with 0.5% SDS and with 0.1% Tween® 20 solution, and then run on a 12% (w/v) SDS-PAGE. To prepare mutant proteins as an active form, the fusion proteins isolated as above were treated with alkaline lysis buffer (0.1 M $Na_2CO_3$, 0.01 M EDTA, 0.17 M NaCl, pH 10.5) at 37° C. for 1 h, and treated with trypsin at 37° C. for 2 h.

2. Bioassays of the Mutants Cry1Ac

The insecticidal activities of the recombinant polyhedra containing mutant Cry1Ac proteins as prepared in 1-4 were determined against the larvae of *Plutella xylostella, Spodoptera exigua*, and *Ostrinia furnacalis*. For the quantification of mutant Cry1Ac proteins occluded in the recombinant polyhedra, the activated proteins were subjected to a 12% SDS-PAGE run, and the amounts were determined by the 1D-gel analysis system (Kodak Co., USA). To evaluate the insecticidal activities against *P. xylostella* and *S. exigua*, each of Chinese cabbage leaf discs (1.5×1.5 $cm^2$) was treated with recombinant polyhedra corresponding to 5 ng or 300 ng, respectively, of the activated mutant protein as prepared above, which was then fed to each of the thirty larvae of *P. xylostella* (3rd instar) or *S. exigua* (2nd-instar). The mortality was scored at 3 days for *P. xylostella* or 5 days for *S. exigua* after the feeding. To determine the insecticidal activity against *O. furnaclis*, the recombinant polyhedra were treated on a small slice of artificial diet (2.0×2.0 $cm^2$) and thirty neonates were laid on each slice. Each *O. furnaclis* neonate was treated with a concentration of 50 ng of the activated mutant protein and their mortality was scored at 6 days after the inoculation.

To determine the median lethal dose ($LD_{50}$), serial dilutions of the recombinant polyhedra were treated on Chinese cabbage leaf discs (1.5×1.5 $cm^2$) and thirty larvae of *P. xylostella* (3rd instar) or *S. exigua* (2nd-instar) were introduced to each leaf surface, respectively. For *O. furnaclis*, serial dilutions of the recombinant polyhedra were treated on a small slice of artificial diet (2.0×2.0 $cm^2$) and thirty neonates were laid on each artificial diet. The mortality was checked for 2 days for *P. xylostella*, 5 days for *S. exigua*, and 6 days for *O. furnacali* with 24 h interval. The $LD_{50}$ was calculated by a Probit analysis (Russell R M, et al., a new computer program for probit analysis. Bull Entomol Soc Am 23:209-213 (1977)) using SPSS statistics 21 (IBM., USA). All assays were performed in triplicates at 25° C. in 60~70% humidity with a 16 h:8 h light-dark cycle.

Example 1

Construction and Expression of Mutant Cry1Ac Genes

Figure 1B:
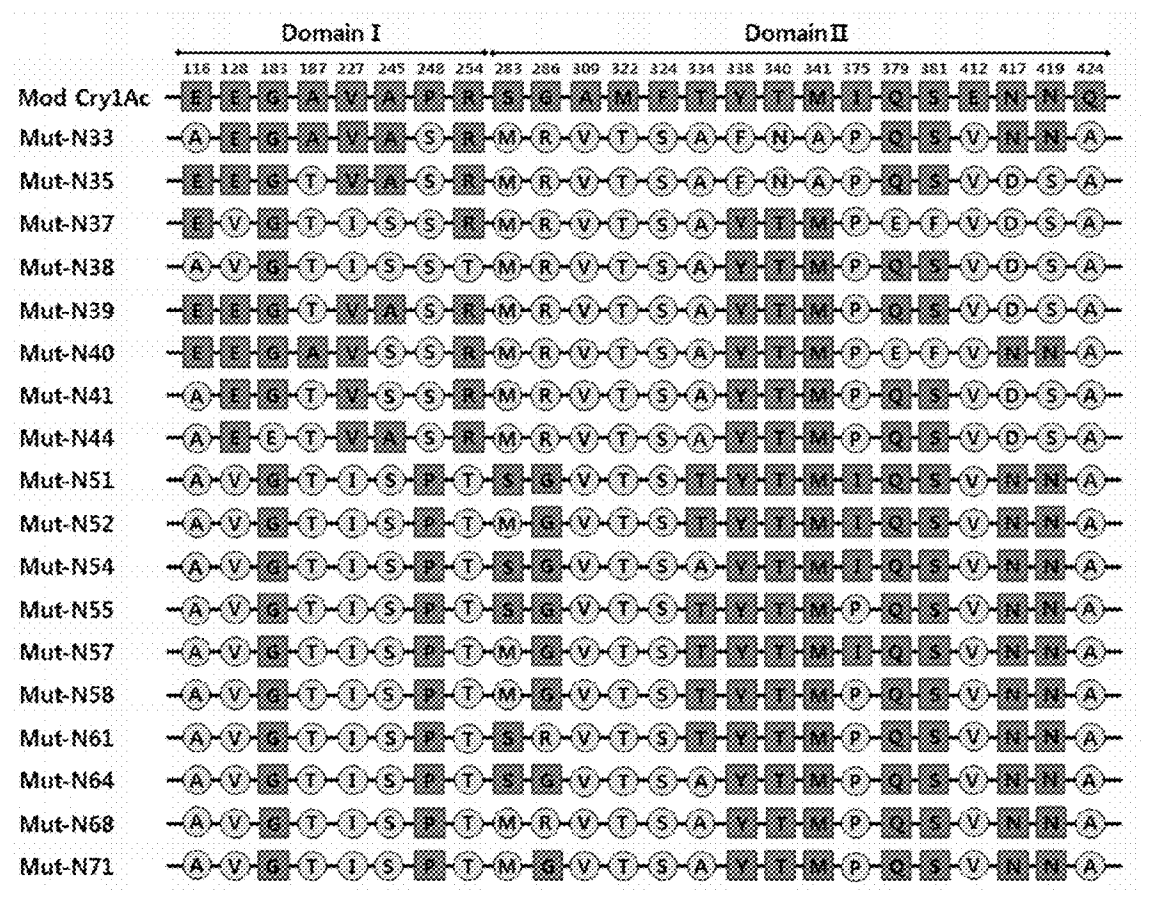
Figure 2A:
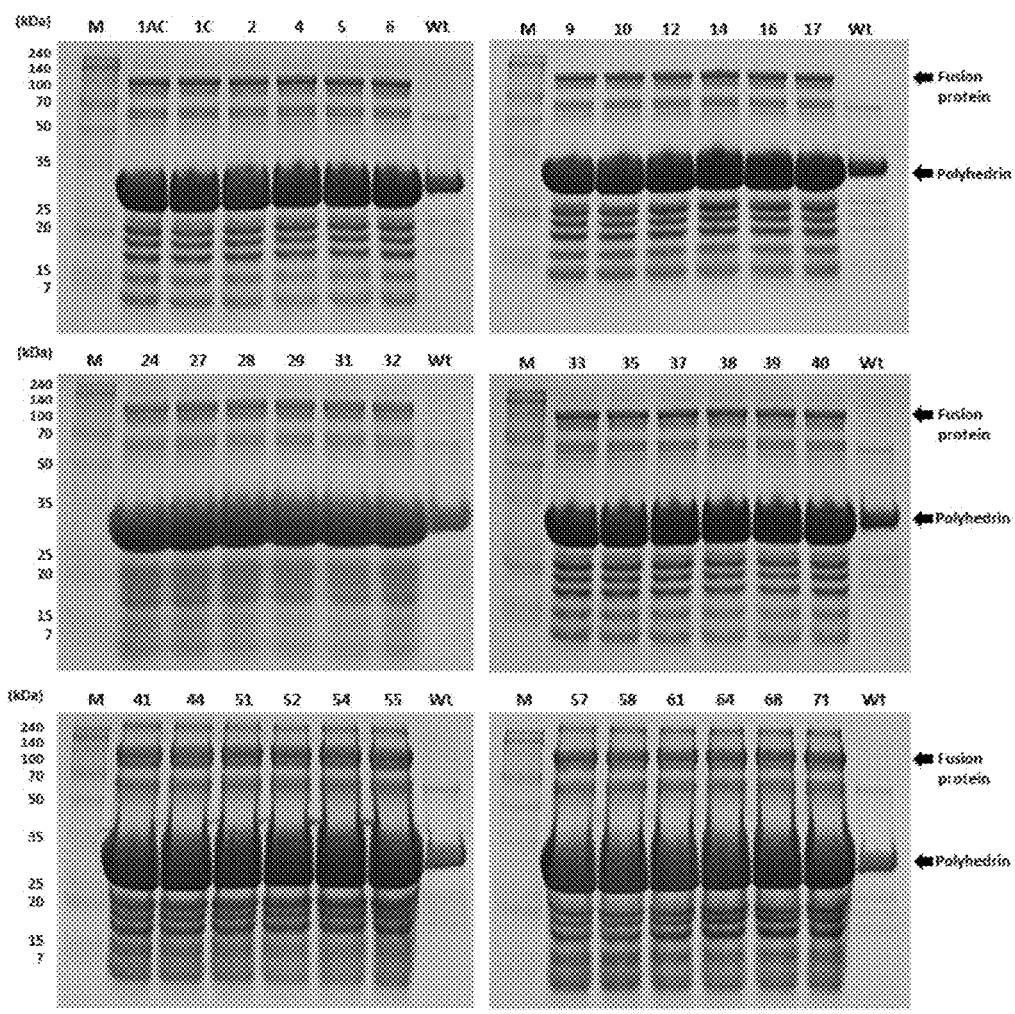
FIG. 2A is SDS-PAGE analysis results of the mutant Cry1Ac proteins fused with polyhedron. Lanes: M, protein molecular weight marker; 1Ac, Cry1Ac; 1C, Cry1C; 2~17, Mut-N02~Mut-N71; Wt, wild-type AcMNPV; C, Mod-Cry1Ac.
Figure 2B:
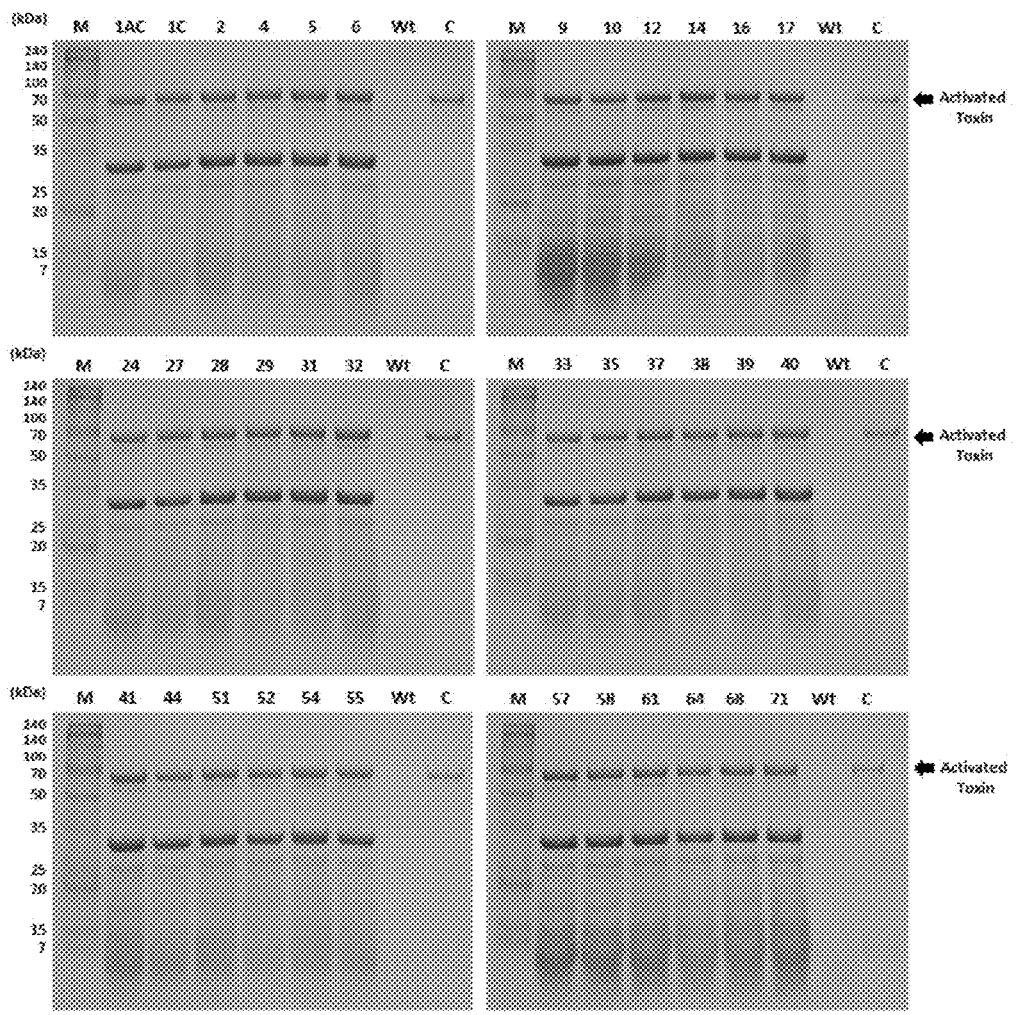
FIG. 2B is SDS-PAGE analysis results of the mutant Cry1Ac proteins fused with polyhedron which was activated by trypsin. Lanes: M, protein molecular weight marker; 1Ac, Cry1Ac; 1C, Cry1C; 2~17, Mut-N02~Mut-N71; Wt, wild-type AcMNPV; C, Mod-Cry1Ac.

Through many rounds of multisite-directed mutagenesis using the primers as in Table 1, a total of 71 mutants were obtained and among these 34 various mutant cry1Ac genes which were stably expressed were selected as shown in FIGS. 2A and 2B and the mutants were named as Mut-NX (the capital letter 'X' represents the clone number), respectively. The mutated residues for each clone were confirmed by DNA sequencing analysis. Each mutant was identified to have various mutated residues across 24 amino acid sequences (FIG. 1).

The 34 mutant cry1Ac genes were expressed using the baculovirus expression vector system. The internal genome structure of the recombinant viruses harboring each mutant cry1Ac gene was confirmed by PCR analysis using specific primer sets (data not shown). Also, RT-PCR analysis showed that the polyhedrin-mutant cry1Ac fusion genes were successfully transcribed in Sf9 cells infected with the recombinant viruses (data not shown).

In SDS-PAGE analysis of the recombinant polyhedra, recombinant viruses showed approximately 95 kDa fusion protein bands while the wild-type *Autographa californica* nucleopolyhedrovirus (AcMNPV) resulted in an approximately 30 kDa polyhedrin protein bands (FIG. 2A). To confirm whether the recombinant polyhedra is cleaved into the active toxin by proteolytic enzymes, the fusion proteins were treated with trypsin which is one of the major proteolytic enzymes present in the insect midgut. The activated mutant Cry1Ac proteins were successfully produced with an approximately 65 kDa in size as activated forms (FIG. 2B).

Example 2

Insecticidal Activity of the Present Mutant Cry1Ac Proteins

Figure 3A:
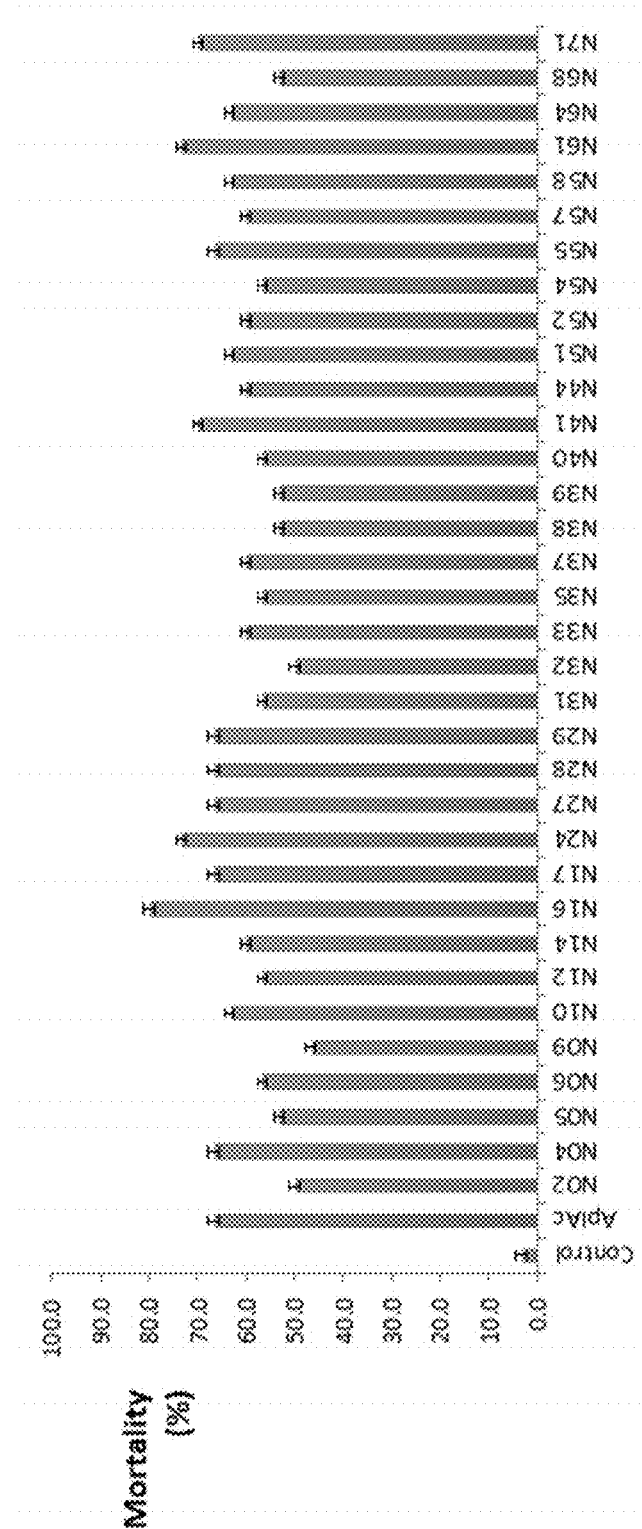
FIG. 3A is a result of Insecticidal activities of each of 34 mutant Cry1Ac proteins against *P. xylostella*, in which 3rd instar larvae were fed with 5 ng of each of the activated mutants/larva and their mortality was scored at 3 days after the feeding.
Figure 3B:
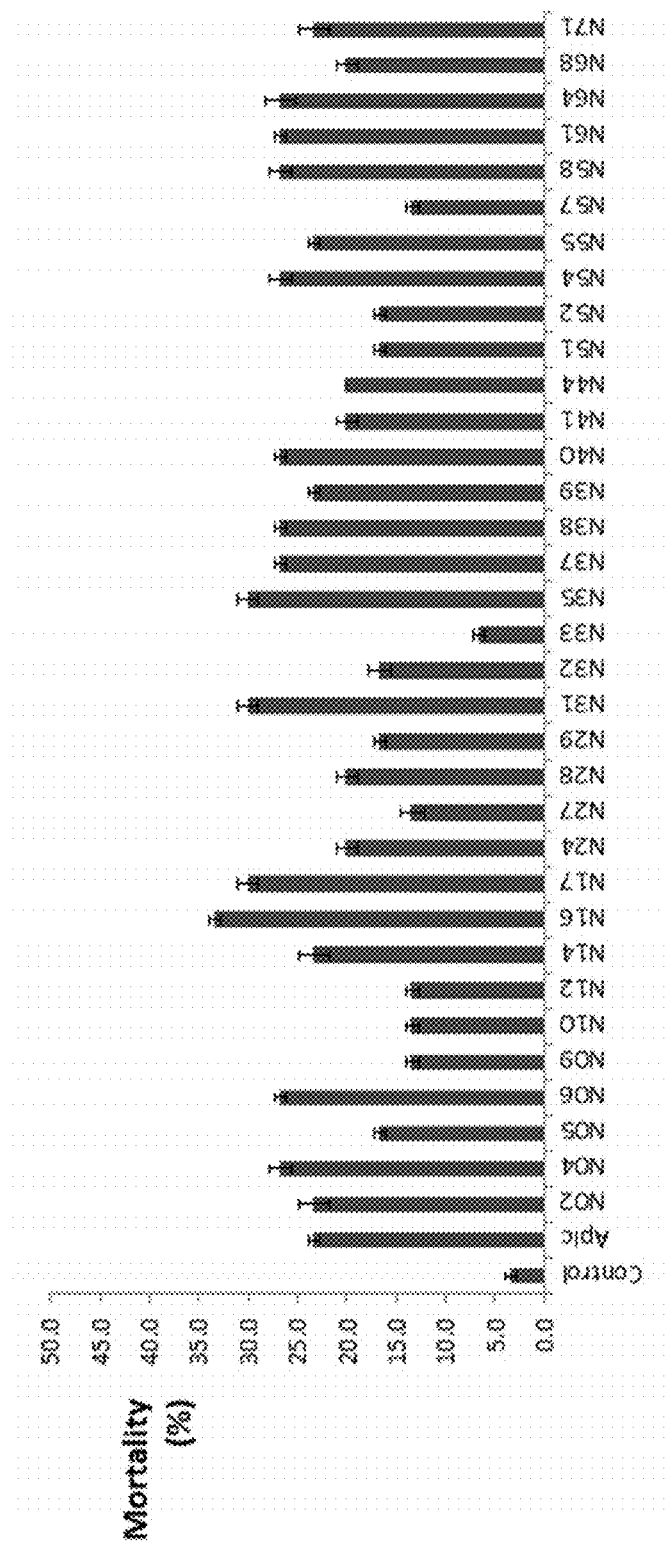
FIG. 3B is a result of Insecticidal activities of each of 34 mutant Cry1Ac proteins against *S. exigua*, in which 2nd instar larvae were fed with 500 ng of each of the activated mutants/larva and their mortality was scored at 5 days after the feeding.
Figure 3C:
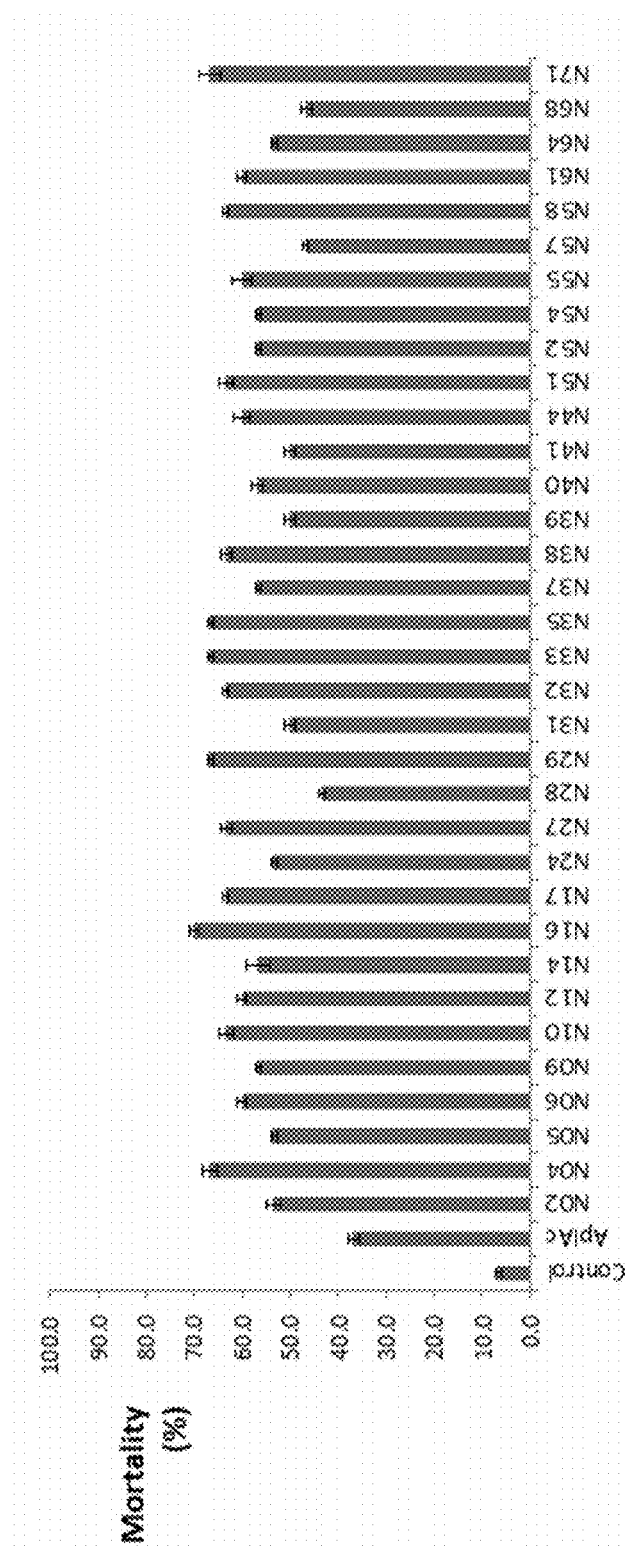
FIG. 3C is a result of insecticidal activities of each of 34 mutant Cry1Ac proteins against *O. furnacalis*, in which neonates were fed with 50 ng of each of the activated mutants/larva and their mortality was scored at 6 days after the feeding.
Figure 4:
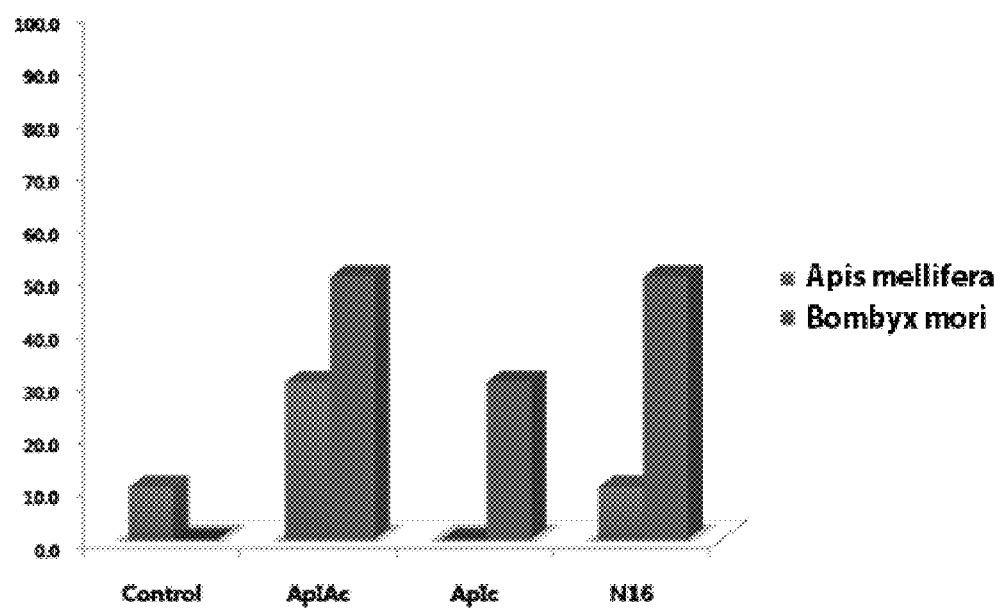
FIG. 4 is a result of testing safety of the Mut-Cry1Ac proteins against adult of *Apis mellifera* and 3rd instar larvae of *Bombyx mori*. Each insect were treated with 500 ng of each toxins (Cry1Ac, Cry1C or Mut-Cry1Ac No. 16) and their mortality was scored 5 days after inoculation.

To evaluate the insecticidal activity of the mutant Cry1Ac proteins as disclosed herein, bioassays were performed against *P. xylostella*, *S. exigua*, and *O. furnacalis*. Bioassays have revealed that the mutant Cry1Ac proteins have high levels of insecticidal activities compared to those of Cry1Ac or Cry1C (FIG. 3). Among these Mut-N04, Mut-N06, and Mut-N16 proteins which yielded the highest insecticidal activities were selected for quantitative bioassays (Table 2). $LD_{50}$ values of these mutant Cry1Ac proteins were about 5.6 to 6.6 times lower against *P. xylostella* and 1.5 to 4.3 times lower against *O. furnacalis* than that of Mod-Cry1Ac. In the bioassay against *S. exigua*, $LD_{50}$ values of these mutant Cry1Ac proteins were similar to that of Cry1C while Mod-cry1Ac showed very low insecticidal activity.

TABLE 2

Insecticidal activities of the present mutant Cry1Ac proteins against various lepidopteran pests.

| | *P. xylostella*[a] | | *S. exigua*[b] | | *O. furnacalis*[c] | |
|---|---|---|---|---|---|---|
| | $LD_{50}$ (ng/larva) | 95% Fiducial limits | $LD_{50}$ (ng/larva) | 95% Fiducial limits | $LD_{50}$ (ng/larva) | 95% Fiducial limits |
| Cry1Ac | 5.21 | 1.09-12.16 | >800.0[d] | ND[e] | 67.8 | 50.0-95.6 |
| Cry1C | >50.00[d] | ND[e] | 226.9 | 70.6-322.9 | >100.0[d] | ND[e] |
| Mut-N04 | 0.86 | 0.35-1.81 | 341.0 | 181.5-168.4 | 38.8 | 16.7-100.8 |
| Mut-N06 | 0.93 | 0.33-2.16 | 321.3 | 182.9-432.4 | 44.1 | 15.0-197.6 |
| Mut-N16 | 0.79 | 0.36-1.57 | 283.7 | 65.5-423.5 | 15.9 | 5.8-29.3 |

[a]The mortality against third instar larvae of *P. xylostella* was scored at 2 days after inoculation.
[b]The mortality against second instar larvae of *S. exigua* was scored at 5 days after inoculation.
[c]The mortality against neonate of *O. furnacalis* was scored at 6 days after inoculation.
[d]The mortality was below 50% even at maximum dose tested.
[e]ND, not determined.

Unless defined otherwise, all technical and scientific terms and any acronyms used herein have the same meanings as commonly understood by one of ordinary skill in the art in the field of the invention. Although any methods and materials similar or equivalent to those described herein can be used in the practice of the present invention, the preferred methods, devices, and materials are described herein.

What is claimed is:

1. A nucleic acid molecule consisting of the nucleic acid sequence set forth in SEQ ID Nos: 37 to 70.

2. A vector comprising the nucleic acid molecule according to claim 1.

3. A cell transformed with the vector according to claim 2.

4. A transgenic plant cell, plant or plant part comprising the nucleic acid molecule of claim 1, wherein the plant part is a seed, a boll, a leaf, a flower, a stem, a root, or any portion thereof; or the plant part is a non-regenerable portion of the seed, boll, leaf, flower, stem or root.

5. A transgenic plant cell, plant or plant part comprising the vector of claim 2, wherein the plant part is a seed, a boll, a leaf, a flower, a stem, a root, or any portion thereof; or the plant part is a non-regenerable portion of the seed, boll, leaf, flower, stem or root.

6. A method of controlling the growth of Lepidopteran pest comprising exposing the pest to the transgenic plant cell, plant or plant part of claim 4, wherein the plant cell, plant or plant part thereof expresses a Lepidopterous inhibitory amount of the mutant cry1Ac protein.

7. The method of claim 5, wherein the Lepidopterous pest is *Ostrinia furnacalis, Ostrinia nubilalis, Chilo suppressalis, Cnaphalocrocis medinalis, Naranga aenescens, Mamestra brassicae, Spodoptera litura, Spodoptera exigua, Spodoptera furgiperda, Helicoverpa armigera, Helicoverpa assulta, Helicoverpa zea, Cucullia fraternal, Pseudaletia separata, Acronicta rumicis, Amphipyra monolitha, Anadevidia peponis, Acanthoplusia agnata, Maruca testulalis, Matsumuraeses phaseoli, Agrotis segetum, Pieris rapae, Plutella xylostella, Endoclyta excrescens, Nepticulidae, Adelidae, Bucculatrigidae, Gracillariidae, Acrolepiopsis sapporensis, Glyphipterigidae, Arctia caja, Bombyx mori, Brahmaea certhia, Dendrolimus spectabilis, Hypantria cunea* or *Lymantria dispar.*

* * * * *